(12) United States Patent
Kuriyama et al.

(10) Patent No.: US 6,500,646 B1
(45) Date of Patent: Dec. 31, 2002

(54) CELL MEMBRANE-DIRECTED DRUGS

(75) Inventors: Shinichi Kuriyama, Tokyo (JP); Takashi Hasegawa, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/331,793

(22) PCT Filed: Jan. 5, 1998

(86) PCT No.: PCT/JP98/00002

§ 371 (c)(1),
(2), (4) Date: Jun. 25, 1999

(87) PCT Pub. No.: WO98/29453

PCT Pub. Date: Jul. 9, 1998

(30) Foreign Application Priority Data

Dec. 27, 1996 (JP) ............................................. 8-359053

(51) Int. Cl.[7] ...................... C07K 19/00; C07K 14/745; A61K 47/48
(52) U.S. Cl. .................... 435/69.7; 435/69.7; 435/69.6; 435/6; 435/320.1; 435/325; 435/252.3; 530/324; 530/350; 530/380; 530/383; 530/384; 424/9.321; 424/450; 514/12; 514/2; 514/44
(58) Field of Search .............................. 435/320.1, 69.6, 435/69.7, 252.3, 6; 530/325, 350, 380, 384, 383, 324; 424/450, 9.32; 514/2, 12, 44

(56) References Cited

U.S. PATENT DOCUMENTS 4,795,806 A * 1/1989 Brown et al. ................ 530/383
5,225,537 A * 7/1993 Foster ......................... 530/380

FOREIGN PATENT DOCUMENTS

| EP | 253455 A | * | 1/1988 | |
|---|---|---|---|---|
| EP | 383599 A | * | 8/1990 | |
| EP | 0253455 A1 | * | 1/1998 | ........... C12N/15/00 |
| JP | 9-20677 | | 1/1997 | |
| WO | 88 05053 A | * | 7/1988 | |
| WO | 88 09343 A | * | 12/1988 | |
| WO | 91 02002 A | * | 3/1991 | |
| WO | WO92/03149 | | 3/1992 | |
| WO | WO94/01138 | | 1/1994 | |
| WO | 93 17122 A | * | 9/1996 | |

OTHER PUBLICATIONS

Gary E. Gilbert et al., Biochemistry, 34 1995, pp. 3022–3031.*

Wen Duanzhi et al., Biochemistry, 26 1987, pp. 4350–4357.*

K. Nakayama et al., Nippon Yakurigaku Zasshi, 88, 1986, pp. 195–203.*

Foster et al., Blood, vol. 75, No. 10 (1990) pp. 1999–2004.

* cited by examiner

*Primary Examiner*—Christopher S. F. Low
*Assistant Examiner*—Chih-Min Kam
(74) *Attorney, Agent, or Firm*—Birch, Stewart, Kolasch & Birch, LLP.

(57) ABSTRACT

Drugs in which peptides having affinity specific for phospholipids, preferably those which are contained in the constituents of lipid bilayers forming the surface layers of cells and of which the proportion in the outer part of each lipid bilayer increases when the cell is not normal, for example, in the case where it is damaged, denatured or activated, and biologically active substances bind to each other, deoxyribonucleic acid (DNA) which codes for the amino acid sequence of the drug in the case where the biologically active substance is a peptide, and processes for producing such drugs. The drugs and novel peptides are useful as preventives and therapeutics of diseases involving coagulopathy, inflammations and immune response.

2 Claims, 22 Drawing Sheets

S1 : TTGTCGACAT GCTTGGGGTC CTGGTCCTT

S2 : ATAAGCTTCC GCTGCTGAGG CCACTGTGC

S3 : TTCTGCAGCT CGAGCCCGTG GACCCGTGC TTC

S4 : GCATTCGCAG CACTCTTCGC ATGG

S5 : AAAATGCATT CGAGTTGCAG CATGCCATTG GGAATGG

S6 : AAAATGCATT CGCTCTTTTT TCAGAATGGC AAAGTAAAGG

S7 : TTGAAGCTTA TGAGGAGCCT CGGGGCCCTG CTCTTGCTG

S8 : GCTCTAGAAT GAGGAGCCTC GGGGCCCTGC TCTTGCTGCT GAGCGCCTGC CTGGCGGTGA
     GCGCTGCTGT GCTACCCCAA GAAGAGGAAG

S9 : AAAGTGCAGA GAGTACTGCG GTGTCCCTGG TGATGGTGAT GAGGAGCTGC TGCGCTTCTC
     CAACAGTTGC AGCATGCCAT TGGGAATGG

FIG.1

A1 : TTGGATCCCA CAGTGGCCTC AGCAGCGGA

A2 : ATGTCGACAC ACTCGCCGTC CACCAGGTC

A3 : AGAATTCGGA TCCTCAGAGT CTCTGCGGCG TCCGCTC

A4 : GATAGTTAAT TCAGGAGGCT TC

A5 : AAAAGAATTC TCGAGTCAGT AGAGGTCCTG TGCCTCGCAG CCCAGAACC

A6 : CGCGGATCCT CAGTTGGAGA AGCGCAGCAG CTCCTCATC

A7 : ATAAGAATGC GGCCGCTCAG TTGGAGAAGC GCAGCAGCTC CTC

A8 : TTTGCGGCCG CTCAGTAGAG GTCCTGTGCC TCGC

FIG.2

F1 : CATTCGACTC GCTACCTTCG AACTCGAG

F2 : AATTCTCGAG TTCGAAGGTA GCGAGTCGAA TGCA

F3 : CGAATTCACC CCCAGAGTTG GGTGCACCAG ATTGCCCTGA GGATGGAGGT TCTGGGCTGC
GAGGCACAGG ACCTCTACTG AGGTACCG

F4 : AATTCGGTAC CTCAGTAGAG GTCCTGTGCC TCGCAGCCCA GAACCTCCAT CCTCAGGGCA
ATCTGGTGCA CCCAACTCTG GGGGTGAATT

F5 : CGCATTCACC CCCAGAGTTG GGTGCACCAG ATTGCCCTGA GGCTGCGCTA CCTTCGAAGC
TTG

F6 : AATTCAAGCT TCGAAGGTAG CGCAGCCTCA GGGCAATCTG GTGCACCCAA CTCTGGGGGT
GAATG

F7 : CGAATTCACC CCCAGAGTTG GGTGCACCAG ATTGCCCTGA GGATGGAGGT TCTGGGCTGC
GAGGCACAGG ACCTCTACTG AGGTACCG

F8 : AATTCGGTAC CTCAGTAGAG GTCCTGTGCC TCGCAGCCCA GAACCTCCAT CCTCAGGGCA
ATCTGGTGCA CCCAACTCTG GGGGTGAATT

F9 : CGAATTCACC CCCAGAGTTG GGTGCACCAG ATTGCCCTGA GGTGAGGTAC CG

F10 : AATTCGGTAC CTCACCTCAG GGCAATCTGG TGCACCCAAC TCTGGGGGTG AATT

FIG.4

F11 : CATTCGTGAG

F12 : AATTCTCACG AATGCA

F13 : AATTCAGCGC TGTGCAGAGA GTACTGCGGT GTCCCTGCAT GCGCATTCAG GACCTGGTAC
      CGCGGCCGCA

F14 : AGCTTGCGGC CGCGGTACCA GGTCCTGAAT GCGCATGCAG GGACACCGCA GTACTCTCTG
      CACAGCGCTG

F15 : GCTGCTGTGC TACCCCAAGA AGAGGAAGGA GATGGGGCGG CCTGCAATCT CCCCATAGTC
      CGGGGCC

F16 : CCGGACTATG GGGAGATTGC AGGCCGCCCC ATCTCCTTCC TCTTCTTGGG CTAGCACAGC
      AGC

F17 : TGAGGAAGGA ATACTTGACA GTTTGAGTTG CAGCATGCAA AATTCGAAAA AAGGTACCA

F18 : AGCTTGGTAC CTTTTTTCGA ATTTTGCATG CTGCAACTCA AACTGTCAAG TATTCCTTCC

F19 : CGAATCCACC CCCAGAGTTG GGTGCACCAG ATTGCCCTGA GGATGGAGGT TCTGGGCTGC
      GAGGCACAGG ACCTCTACTG AAGCTTGGTA C

F20 : CAAGCTTCAG TAGAGGTCCT GTGCCTCGCA GCCCAGAACC TCCATCCTCA GGGCAATCTG
      GTGCACCCAA CTCTGGGGGT GGATT

FIG.5

SEQUENCE LISTING

```
<160> NUMBER OF SEQ ID NOS:  67

<210> SEQ ID NO 1
<211> LENGTH: 130
<212> TYPE: PRT
<213> ORGANISM: Homo Sapiens

<400> SEQUENCE: 1

Ser Cys Ser Met Pro Leu Gly Met Glu Ser Lys Ala Ile Ser Asp Ala
```

```
                   1               5                    10                    15
               Gln Ile Thr Ala Ser Ser Tyr Phe Thr Asn Met Phe Ala Thr Trp Ser
                              20                   25                   30

Pro Ser Lys Ala Arg Leu His Leu Gln Gly Arg Ser Asn Ala Trp Arg
                         35                   40                   45

Pro Gln Val Asn Asn Pro Lys Glu Trp Leu Gln Val Asp Phe Gln Lys
                         50                   55                   60

Thr Met Lys Val Thr Gly Val Thr Thr Gln Gly Val Lys Ser Leu Leu
               65                   70                   75                   80

Thr Ser Met Tyr Val Lys Glu Phe Leu Ile Ser Ser Ser Gln Asp Gly
                                   85                   90                   95

His Gln Trp Thr Leu Phe Phe Gln Asn Gly Lys Val Lys Val Phe Gln
                              100                  105                  110

Gly Asn Gln Asp Ser Phe Thr Pro Val Val Asn Ser Leu Asp Pro Pro
                              115                  120                  125

Leu Leu
                   130

<210> SEQ ID NO 2
<211> LENGTH: 18
<212> TYPE: PRT
<213> ORGANISM: Homo Sapiens
<220> FEATURE:
<221> NAME/KEY: UNSURE
<222> LOCATION: (1)..(1)
<223> OTHER INFORMATION: Xaa = Thr or Leu

<400> SEQUENCE: 2

Xaa Arg Tyr Leu Arg Ile His Pro Gln Ser Trp Val His Gln Ile Ala
1               5                   10                  15

Leu Arg

<210> SEQ ID NO 3
<211> LENGTH: 12
<212> TYPE: PRT
<213> ORGANISM: Homo Sapiens

<400> SEQUENCE: 3

Met Glu Val Leu Gly Cys Glu Ala Gln Asp Leu Tyr
1               5                   10

<210> SEQ ID NO 4
<211> LENGTH: 497
<212> TYPE: PRT
<213> ORGANISM: Homo Sapiens

<400> SEQUENCE: 4

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
                    35                  40                  45

Ala Ala Asp Val Ile Ser Leu Leu Leu Asn Gly Asp Gly Gly Val Gly
                50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95
```

-continued

```
Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
            195                 200                 205

Pro Pro Gly Ala Val Gln Gly His Trp Ala Arg Glu Ala Pro Gly Ala
    210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
                260                 265                 270

Leu Cys Glu His Phe Cys Val Pro Asn Pro Asp Gln Pro Gly Ser Tyr
            275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350

Arg Ala Asn Cys Glu Tyr Gln Cys Gln Pro Leu Asn Gln Thr Ser Tyr
            355                 360                 365

Leu Cys Val Cys Ala Glu Gly Phe Ala Pro Ile Pro His Glu Pro His
    370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Glu Cys Glu Asn Gly Gly Phe
            420                 425                 430

Cys Ser Gly Val Cys His Asn Leu Pro Gly Thr Phe Glu Cys Ile Cys
    435                 440                 445

Gly Pro Asp Ser Ala Leu Val Arg His Ile Gly Thr Asp Cys Asp Ser
    450                 455                 460

Gly Lys Val Asp Gly Gly Asp Ser Gly Ser Gly Glu Pro Pro Pro Ser
465                 470                 475                 480

Pro Thr Pro Gly Ser Thr Leu Thr Pro Pro Ala Val Gly Leu Val His
                485                 490                 495

Ser
```

```
<210> SEQ ID NO 5
<211> LENGTH: 30
<212> TYPE: PRT
<213> ORGANISM: Synthetic

<400> SEQUENCE: 5

Thr Arg Tyr Leu Arg Ile His Pro Gln Ser Trp Val His Gln Ile Ala
1               5                   10                  15

Leu Arg Met Glu Val Leu Gly Cys Glu Ala Gln Asp Leu Tyr
            20                  25                  30

<210> SEQ ID NO 6
<211> LENGTH: 48
<212> TYPE: PRT
<213> ORGANISM: Synthetic

<400> SEQUENCE: 6

Thr Arg Tyr Leu Arg Ile His Pro Gln Ser Trp Val His Gln Ile Ala
1               5                   10                  15

Leu Arg Leu Arg Tyr Leu Arg Ile His Pro Gln Ser Trp Val His Gln
            20                  25                  30

Ile Ala Leu Arg Met Glu Val Leu Gly Cys Glu Ala Gln Asp Leu Tyr
        35                  40                  45

<210> SEQ ID NO 7
<211> LENGTH: 66
<212> TYPE: PRT
<213> ORGANISM: Synthetic

<400> SEQUENCE: 7

Thr Arg Tyr Leu Arg Ile His Pro Gln Ser Trp Val His Gln Ile Ala
1               5                   10                  15

Leu Arg Leu Arg Tyr Leu Arg Ile His Pro Gln Ser Trp Val His Gln
            20                  25                  30

Ile Ala Leu Arg Leu Arg Tyr Leu Arg Ile His Pro Gln Ser Trp Val
        35                  40                  45

His Gln Ile Ala Leu Arg Met Glu Val Leu Gly Cys Glu Ala Gln Asp
    50                  55                  60

Leu Tyr
65

<210> SEQ ID NO 8
<211> LENGTH: 60
<212> TYPE: PRT
<213> ORGANISM: Homo Sapiens

<400> SEQUENCE: 8

Leu Phe Phe Gln Asn Gly Lys Val Lys Val Phe Gln Gly Asn Gln Asp
1               5                   10                  15

Ser Phe Thr Pro Val Val Asn Ser Leu Asp Pro Leu Leu Thr Arg
            20                  25                  30

Tyr Leu Arg Ile His Pro Gln Ser Trp Val His Gln Ile Ala Leu Arg
        35                  40                  45

Met Glu Val Leu Gly Cys Glu Ala Gln Asp Leu Tyr
    50                  55                  60

<210> SEQ ID NO 9
<211> LENGTH: 160
<212> TYPE: PRT
<213> ORGANISM: Homo Sapiens
```

```
<400> SEQUENCE: 9

Ser Cys Ser Met Pro Leu Gly Met Glu Ser Lys Ala Ile Ser Asp Ala
1               5                   10                  15

Gln Ile Thr Ala Ser Ser Tyr Phe Thr Asn Met Phe Ala Thr Trp Ser
            20                  25                  30

Pro Ser Lys Ala Arg Leu His Leu Gln Gly Arg Ser Asn Ala Trp Arg
        35                  40                  45

Pro Gln Val Asn Asn Pro Lys Glu Trp Leu Gln Val Asp Phe Gln Lys
    50                  55                  60

Thr Met Lys Val Thr Gly Val Thr Thr Gln Gly Val Lys Ser Leu Leu
65                  70                  75                  80

Thr Ser Met Tyr Val Lys Glu Phe Leu Ile Ser Ser Gln Asp Gly
                85                  90                  95

His Gln Trp Thr Leu Phe Phe Gln Asn Gly Lys Val Lys Val Phe Gln
            100                 105                 110

Gly Asn Gln Asp Ser Phe Thr Pro Val Val Asn Ser Leu Asp Pro Pro
        115                 120                 125

Leu Leu Thr Arg Tyr Leu Arg Ile His Pro Gln Ser Trp Val His Gln
    130                 135                 140

Ile Ala Leu Arg Met Glu Val Leu Gly Cys Glu Ala Gln Asp Leu Tyr
145                 150                 155                 160

<210> SEQ ID NO 10
<211> LENGTH: 30
<212> TYPE: PRT
<213> ORGANISM: Homo Sapiens

<400> SEQUENCE: 10

Leu Phe Phe Gln Asn Gly Lys Val Lys Val Phe Gln Gly Asn Gln Asp
1               5                   10                  15

Ser Phe Thr Pro Val Val Asn Ser Leu Asp Pro Pro Leu Leu
            20                  25                  30

<210> SEQ ID NO 11
<211> LENGTH: 390
<212> TYPE: DNA
<213> ORGANISM: Homo Sapiens

<400> SEQUENCE: 11
agttgcagca tgccattggg aatggagagt aaagcaatat cagatgcaca gattactgct      60
tcatcctact ttaccaatat gtttgccacc tggtctcctt caaaagctcg acttcacctc    120
caagggagga gtaatgcctg agacctcag gtgaataatc caaagagtg gctgcaagtg     180 gacttccaga agacaatgaa agtcacagga gtaactactc agggagtaaa atctctgctt    240
accagcatgt atgtgaagga gttcctcatc tccagcagtc aagatggcca tcagtggact    300 ctctttttc agaatggcaa agtaaaggtt tttcagggaa atcaagactc cttcacacct    360
gtggtgaact ctctagaccc accgttactg                                     390

<210> SEQ ID NO 12
<211> LENGTH: 90
<212> TYPE: DNA
<213> ORGANISM: Homo Sapiens

<400> SEQUENCE: 12
ctcttttttc agaatggcaa agtaaaggtt tttcagggaa atcaagactc cttcacacct     60
gtggtgaact ctctagaccc accgttactg                                      90
```

<210> SEQ ID NO 13
<211> LENGTH: 54
<212> TYPE: DNA
<213> ORGANISM: Homo Sapiens

<400> SEQUENCE: 13
actcgctacc ttcgmattca cccccagagt tgggtgcacc agattgccct gagg          54

<210> SEQ ID NO 14
<211> LENGTH: 54
<212> TYPE: DNA
<213> ORGANISM: Homo Sapiens

<400> SEQUENCE: 14
ctgcgctacc ttcgmattca cccccagagt tgggtgcacc agattgccct gagg          54

<210> SEQ ID NO 15
<211> LENGTH: 36
<212> TYPE: DNA
<213> ORGANISM: Homo Sapiens

<400> SEQUENCE: 15
atggaggttc tgggctgcga ggcacaggac ctctac                              36

<210> SEQ ID NO 16
<211> LENGTH: 90
<212> TYPE: DNA
<213> ORGANISM: Synthetic

<400> SEQUENCE: 16
actcgctacc ttcgaattca cccccagagt tgggtgcacc agattgccct gaggatggag    60
gttctgggct gcgaggcaca ggacctctac                                     90

<210> SEQ ID NO 17
<211> LENGTH: 144
<212> TYPE: DNA
<213> ORGANISM: Synthetic

<400> SEQUENCE: 17
actcgctacc ttcgcattca cccccagagt tgggtgcacc agattgccct gaggctgcgc    60
taccttcgaa ttcacccccca gagttgggtg caccagattg ccctgaggat ggaggttctg   120
ggctgcgagg cacaggacct ctac                                           144

<210> SEQ ID NO 18
<211> LENGTH: 198
<212> TYPE: DNA
<213> ORGANISM: Synthetic

<400> SEQUENCE: 18
actcgctacc ttcgcattca cccccagagt tgggtgcacc agattgccct gaggctgcgc    60
taccttcgca ttcaccccca gagttgggtg caccagattg ccctgaggct gcgctacctt    120
cgaattcacc ccagagttgg gtgcaccag attgccctga ggatggaggt tctgggctgc    180
gaggcacagg acctctac                                                  198

<210> SEQ ID NO 19
<211> LENGTH: 180
<212> TYPE: DNA
<213> ORGANISM: Homo Sapiens

```
<400> SEQUENCE: 19
ctcttttttc agaatggcaa agtaaaggtt tttcagggaa atcaagactc cttcacacct      60
gtggtgaact ctctagaccc accgttactg actcgctacc ttcgaattca cccccagagt     120
tgggtgcacc agattgccct gaggatggag gttctgggct gcgaggcaca ggacctctac     180

<210> SEQ ID NO 20
<211> LENGTH: 480
<212> TYPE: DNA
<213> ORGANISM: Homo Sapiens

<400> SEQUENCE: 20
agttgcagca tgccattggg aatggagagt aaagcaatat cagatgcaca gattactgct      60
tcatcctact ttaccaatat gtttgccacc tggtctcctt caaaagctcg acttcacctc     120
caagggagga gtaatgcctg agacctcag gtgaataatc caaagagtg gctgcaagtg      180 gacttccaga agacaatgaa agtcacagga gtaactactc agggagtaaa atctctgctt     240
accagcatgt atgtgaagga gttcctcatc tccagcagtc aagatggcca tcagtggact     300
ctcttttttc agaatggcaa agtaaaggtt tttcagggaa atcaagactc cttcacacct     360
gtggtgaact ctctagaccc accgttactg actcgctacc ttcgaattca cccccagagt     420
tgggtgcacc agattgccct gaggatggag gttctgggct gcgaggcaca ggacctctac     480

<210> SEQ ID NO 21
<211> LENGTH: 1491
<212> TYPE: DNA
<213> ORGANISM: Homo Sapiens

<400> SEQUENCE: 21
gctcccgcag agccgcagcc gggtggcagc cagtgcgtcg agcacgactg cttcgcgctc      60
tacccgggcc ccgcgacctt cctcaatgcc agtcagatct gcgacggact gcggggccac     120
ctaatgacag tgcgctcctc ggtggctgcc gatgtcattt ccttgctact gaacggcgac     180
ggcggcgttg gccgccggcg cctctggatc ggcctgcagc tgccacccgg ctgcggcgac     240
cccaagcgcc tcgggcccct gcgcggcttc cagtgggtta cgggagacaa caacaccagc     300
tatagcaggt gggcacggct cgacctcaat ggggctcccc tctgcggccc gttgtgcgtc     360
gctgtctccg ctgctgaggc cactgtgccc agcgagccga tctgggagga gcagcagtgc     420
gaagtgaagg ccgatggctt cctctgcgag ttccacttcc cagccacctg caggccactg     480
gctgtggagc ccggcgccgc ggctgccgcc gtctcgatca cctacggcac cccgttcgcg     540
gcccgcggag cggacttcca ggcgctgccg gtgggcagct ccgccgcggt ggctccctc      600 ggcttacagc taatgtgcac cgcgccgccc ggagcggtcc aggggcactg ggccagggag     660
gcgccgggcg cttgggactg cagcgtggag aacggcggct cgagcacgc gtgcaatgcg     720 atccctgggg ctccccgctg ccagtgccca gccggcgccg ccctgcaggc agacgggcgc     780
tcctgcaccg catccgcgac gcagtcctgc aacgacctct gcgagcactt ctgcgttccc     840
aaccccgacc agccgggctc ctactcgtgc atgtgcgaga ccggctaccg gctggcggcc     900
gaccaacacc ggtgcgagga cgtggatgac tgcatactgg agcccagtcc gtgtccgcag     960
cgctgtgtca acacacaggg tggcttcgag tgccactgct accctaacta cgacctggtg    1020
gacggcgagt gtgtcgagcc cgtggacccg tgcttcagag ccaactgcga gtaccagtgc    1080 cagccctga accaaactag ctacctctgc gtctgcgccc agggcttcgc gcccattccc    1140
cacgagccgc acaggtgcca gatgttttgc aaccagactg cctgtccagc cgactgcgac    1200
```

-continued

```
cccaacaccc aggctagctg tgagtgccct gaaggctaca tcctggacga cggtttcatc    1260
tgcacggaca tcgacgagtg cgaaaacggc ggcttctgct ccggggtgtg ccacaacctc    1320
cccggtacct tcgagtgcat ctgcgggccc gactcggccc ttgtccgcca cattggcacc    1380
gactgtgact ccggcaaggt ggacggtggc gacagcggct ctggcgagcc ccgcccagc     1440 ccgacgcccg gctccacctt gactcctccg gccgtgggc tcgtgcattc g              1491
```

<210> SEQ ID NO 22
<211> LENGTH: 36
<212> TYPE: PRT
<213> ORGANISM: Synthetic

<400> SEQUENCE: 22

Thr Arg Tyr Leu Arg Ile His Pro Gln Ser Trp Val His Gln Ile Ala
1               5                   10                  15

Leu Arg Leu Arg Tyr Leu Arg Ile His Pro Gln Ser Trp Val His Gln
            20                  25                  30

Ile Ala Leu Arg
        35

<210> SEQ ID NO 23
<211> LENGTH: 68
<212> TYPE: PRT
<213> ORGANISM: Homo Sapiens

<400> SEQUENCE: 23

Ala Ala Cys Asn Leu Pro Ile Val Arg Gly Pro Cys Arg Ala Phe Ile
1               5                   10                  15

Gln Leu Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro Gly Asp Gly Asp Glu Glu Leu Leu
    50                  55                  60

Arg Phe Ser Asn
65

<210> SEQ ID NO 24
<211> LENGTH: 147
<212> TYPE: PRT
<213> ORGANISM: Homo Sapiens

<400> SEQUENCE: 24

Ala Val Leu Pro Gln Glu Glu Gly Ser Gly Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

```
Gly Gly Cys Gln Gly Asn Gly Asn Lys Phe Tyr Ser Glu Lys Glu Cys
            115                 120                 125

Arg Glu Tyr Cys Gly Val Pro Gly Asp Gly Asp Glu Glu Leu Leu Arg
        130                 135                 140

Phe Ser Asn
145

<210> SEQ ID NO 25
<211> LENGTH: 279
<212> TYPE: PRT
<213> ORGANISM: Homo Sapiens

<400> SEQUENCE: 25

Cys Glu Glu Pro Pro Thr Phe Glu Ala Met Glu Leu Ile Gly Lys Pro
1               5                   10                  15

Lys Pro Tyr Tyr Glu Ile Gly Glu Arg Val Asp Tyr Lys Cys Lys Lys
            20                  25                  30

Gly Tyr Phe Tyr Ile Pro Pro Leu Ala Thr His Thr Ile Cys Asp Arg
        35                  40                  45

Asn His Thr Trp Leu Pro Val Ser Asp Asp Ala Cys Tyr Arg Glu Thr
    50                  55                  60

Cys Pro Tyr Ile Arg Asp Pro Leu Asn Gly Gln Ala Val Pro Ala Asn
65                  70                  75                  80

Gly Thr Tyr Glu Phe Gly Tyr Gln Met His Phe Ile Cys Asn Glu Gly
                85                  90                  95

Tyr Tyr Leu Ile Gly Glu Glu Ile Leu Tyr Cys Glu Leu Lys Gly Ser
            100                 105                 110

Val Ala Ile Trp Ser Gly Lys Pro Pro Ile Cys Glu Lys Val Leu Cys
        115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
        195                 200                 205

Gly Lys Lys Phe Tyr Tyr Lys Ala Thr Val Met Phe Glu Cys Asp Lys
    210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Gly Pro Arg Pro Thr
                245                 250                 255

Tyr Lys Pro Pro Val Ser Asn Tyr Pro Gly Tyr Pro Lys Pro Glu Glu
            260                 265                 270

Gly Ile Leu Asp Ser Leu Asp
        275

<210> SEQ ID NO 26
<211> LENGTH: 108
<212> TYPE: DNA
<213> ORGANISM: Synthetic

<400> SEQUENCE: 26
```

-continued

```
actcgctacc ttcgcattca cccccagagt tgggtgcacc agattgccct gaggctgcgc    60
taccttcgaa ttcaccccca gagttgggtg caccagattg ccctgagg              108
```

<210> SEQ ID NO 27
<211> LENGTH: 204
<212> TYPE: DNA
<213> ORGANISM: Homo Sapiens

<400> SEQUENCE: 27

```
gcggcctgca atctccccat agtccggggc ccctgccgag ccttcatcca gctctgggca    60
tttgatgctg tcaaggggaa gtgcgtcctc ttcccctacg ggggctgcca gggcaacggg   120
aacaagttct actcagagaa ggagtgcaga gagtactgcg gtgtccctgg tgatggtgat   180
gaggagctgc tgcgcttctc caac                                          204
```

<210> SEQ ID NO 28
<211> LENGTH: 441
<212> TYPE: DNA
<213> ORGANISM: Homo Sapiens

<400> SEQUENCE: 28

```
gctgtgctac cccaagaaga ggaaggatca gggggtgggc aactggtaac tgaagtcacc    60
aagaaagaag attcctgcca gctgggctac tcggccggtc cctgcatggg aatgaccagc   120
aggtatttct ataatggtac atccatggcc tgtgagactt tccagtacgg cggctgcatg   180
ggcaacggta caacttcgt cacagaaaag gagtgtctgc agacctgccg aactgtggcg   240
gcctgcaatc tccccatagt ccggggcccc tgccgagcct tcatccagct ctgggcattt   300
gatgctgtca aggggaagtg cgtcctcttc ccctacgggg gctgccaggg caacgggaac   360
aagttctact cagagaagga gtgcagagag tactgcggtg tccctggtga tggtgatgag   420
gagctgctgc gcttctccaa c                                             441
```

<210> SEQ ID NO 29
<211> LENGTH: 837
<212> TYPE: DNA
<213> ORGANISM: Homo Sapiens

<400> SEQUENCE: 29

```
tgtgaggagc caccaacatt tgaagctatg gagctcattg gtaaaccaaa accctactat    60
gagattggtg aacgagtaga ttataagtgt aaaaaggat acttctatat acctcctctt   120
gccacccata ctatttgtga tcggaatcat acatggctac ctgtctcaga tgacgcctgt   180
tatagagaaa catgtccata tacgggat cctttaaatg ccaagcagt ccctgcaaat   240 gggacttacg agtttggtta tcagatgcac tttatttgta atgagggtta ttacttaatt   300
ggtgaagaaa ttctatattg tgaacttaaa ggatcagtag caatttggag cggtaagccc   360
ccaatatgtg aaaaggtttt gtgtacacca cctccaaaaa taaaaaatgg aaaacacacc   420
tttagtgaag tagaagtatt tgagtatctt gatgcagtaa cttatagttg tgatcctgca   480
cctggaccag atccattttc acttattgga gagagcacga tttattgtgg tgacaattca   540
gtgtggagtc gtgctgctcc agagtgtaaa gtggtcaaat gtcgatttcc agtagtcgaa   600
aatggaaaac agatatcagg atttggaaaa aattttact acaaagcaac agttatgttt   660
gaatgcgata agggttttta cctcgatggc agcgacacaa ttgtctgtga cagtaacagt   720
acttgggatc ccccagttcc aaagtgtctt aaaggtccta ggcctactta caagcctcca   780
```

-continued gtctcaaatt atccaggata tcctaaacct gaggaaggaa tacttgacag tttggat            837

<210> SEQ ID NO 30
<211> LENGTH: 29
<212> TYPE: DNA
<213> ORGANISM: Synthetic DNA Primers

<400> SEQUENCE: 30
ttgtcgacat gcttggggtc ctggtcctt            29

<210> SEQ ID NO 31
<211> LENGTH: 29
<212> TYPE: DNA
<213> ORGANISM: Synthetic DNA Primers

<400> SEQUENCE: 31
ataagcttcc gctgctgagg ccactgtgc            29

<210> SEQ ID NO 32
<211> LENGTH: 33
<212> TYPE: DNA
<213> ORGANISM: Synthetic DNA Primers

<400> SEQUENCE: 32
ttctgcagct cgagccccgt ggacccgtgc ttc            33

<210> SEQ ID NO 33
<211> LENGTH: 24
<212> TYPE: DNA
<213> ORGANISM: Synthetic DNA Primers

<400> SEQUENCE: 33
gcattcgcag cactcttgcg atgg            24

<210> SEQ ID NO 34
<211> LENGTH: 37
<212> TYPE: DNA
<213> ORGANISM: Synthetic DNA Primers

<400> SEQUENCE: 34
aaaatgcatt cgagttgcag catgccattg ggaatgg            37

<210> SEQ ID NO 35
<211> LENGTH: 40
<212> TYPE: DNA
<213> ORGANISM: Synthetic DNA Primers

<400> SEQUENCE: 35
aaaatgcatt cgctcttttt tcagaatggc aaagtaaagg            40

<210> SEQ ID NO 36
<211> LENGTH: 39
<212> TYPE: DNA
<213> ORGANISM: Synthetic DNA Primers

<400> SEQUENCE: 36
ttgaagctta tgaggagcct cggggccctg ctcttgctg            39

<210> SEQ ID NO 37
<211> LENGTH: 90
<212> TYPE: DNA
<213> ORGANISM: Synthetic DNA Primers

<400> SEQUENCE: 37

```
gctctagaat gaggagcctc ggggccctgc tcttgctgct gagcgcctgc ctggcggtga      60
gcgctgctgt gctaccccaa gaagaggaag                                      90

<210> SEQ ID NO 38
<211> LENGTH: 89
<212> TYPE: DNA
<213> ORGANISM: Synthetic DNA Primers

<400> SEQUENCE: 38
aaagtgcaga gagtactgcg gtgtccctgg tgatggtgat gaggagctgc tgcgcttctc      60
caacagttgc agcatgccat tgggaatgg                                       89

<210> SEQ ID NO 39
<211> LENGTH: 28
<212> TYPE: DNA
<213> ORGANISM: Synthetic DNA Primers

<400> SEQUENCE: 39
ttggtcccac agtggcctca gcagcgga                                        28

<210> SEQ ID NO 40
<211> LENGTH: 29
<212> TYPE: DNA
<213> ORGANISM: Synthetic DNA Primers

<400> SEQUENCE: 40
atgtcgacac actcgccgtc caccaggtc                                       29

<210> SEQ ID NO 41
<211> LENGTH: 37
<212> TYPE: DNA
<213> ORGANISM: Synthetic DNA Primers

<400> SEQUENCE: 41
agaattcgga tcctcagagt ctctgcggcg tccgctc                              37

<210> SEQ ID NO 42
<211> LENGTH: 22
<212> TYPE: DNA
<213> ORGANISM: Synthetic DNA Primers

<400> SEQUENCE: 42
gatagttaat tcaggaggct tc                                              22

<210> SEQ ID NO 43
<211> LENGTH: 49
<212> TYPE: DNA
<213> ORGANISM: Synthetic DNA Primers

<400> SEQUENCE: 43
aaaagaattc tcgagtcagt agaggtcctg tgcctcgcag cccagaacc                 49

<210> SEQ ID NO 44
<211> LENGTH: 39
<212> TYPE: DNA
<213> ORGANISM: Synthetic DNA Primers

<400> SEQUENCE: 44
cgcggatcct cagttggaga agcgcagcag ctcctcatc                            39

<210> SEQ ID NO 45
```

```
<211> LENGTH: 43
<212> TYPE: DNA
<213> ORGANISM: Synthetic DNA Primers

<400> SEQUENCE: 45
ataagaatgc ggccgctcag ttggagaagc gcagcagctc ctc                     43

<210> SEQ ID NO 46
<211> LENGTH: 34
<212> TYPE: DNA
<213> ORGANISM: Synthetic DNA Primers

<400> SEQUENCE: 46
tttgcggccg ctcagtagag gtcctgtgcc tcgc                               34

<210> SEQ ID NO 47
<211> LENGTH: 28
<212> TYPE: DNA
<213> ORGANISM: Synthetic DNA Primers

<400> SEQUENCE: 47
cattcgactc gctaccttcg aactcgag                                      28

<210> SEQ ID NO 48
<211> LENGTH: 34
<212> TYPE: DNA
<213> ORGANISM: Synthetic DNA Primers

<400> SEQUENCE: 48
aattctcgag ttcgaaggta gcgagtcgaa tgca                               34

<210> SEQ ID NO 49
<211> LENGTH: 88
<212> TYPE: DNA
<213> ORGANISM: Synthetic DNA Primers

<400> SEQUENCE: 49
cgaattcacc cccagagttg ggtgcaccag attgccctga ggatggaggt tctgggctgc   60
gaggcacagg acctctactg aggtaccg                                      88

<210> SEQ ID NO 50
<211> LENGTH: 90
<212> TYPE: DNA
<213> ORGANISM: Synthetic DNA Primers

<400> SEQUENCE: 50
aattcggtac ctcagtagag gtcctgtgcc tcgcagccca gaacctccat cctcagggca   60
atctggtgca cccaactctg ggggtgaatt                                    90

<210> SEQ ID NO 51
<211> LENGTH: 63
<212> TYPE: DNA
<213> ORGANISM: Synthetic DNA Primers

<400> SEQUENCE: 51
cgcattcacc cccagagttg ggtgcaccag attgccctga ggctgcgcta ccttcgaagc   60
ttg                                                                 63

<210> SEQ ID NO 52
<211> LENGTH: 65
<212> TYPE: DNA
<213> ORGANISM: Synthetic DNA Primers
```

<400> SEQUENCE: 52
aattcaagct tcgaaggtag cgcagcctca gggcaatctg gtgcacccaa ctctgggggt    60
gaatg    65

<210> SEQ ID NO 53
<211> LENGTH: 88
<212> TYPE: DNA
<213> ORGANISM: Synthetic DNA Primers

<400> SEQUENCE: 53
cgaattcacc cccagagttg ggtgcaccag attgccctga ggatggaggt tctgggctgc    60
gaggcacagg acctctactg aggtaccg    88

<210> SEQ ID NO 54
<211> LENGTH: 90
<212> TYPE: DNA
<213> ORGANISM: Synthetic DNA Primers

<400> SEQUENCE: 54
aattcggtac ctcagtagag gtcctgtgcc tcgcagccca gaacctccat cctcagggca    60
atctggtgca cccaactctg ggggtgaatt    90

<210> SEQ ID NO 55
<211> LENGTH: 52
<212> TYPE: DNA
<213> ORGANISM: Synthetic DNA Primers

<400> SEQUENCE: 55
cgaattcacc cccagagttg ggtgcaccag attgccctga ggtgaggtac cg    52

<210> SEQ ID NO 56
<211> LENGTH: 49
<212> TYPE: DNA
<213> ORGANISM: Synthetic DNA Primers

<400> SEQUENCE: 56
aattcggtac ctcagggcaa tctggtgcac ccaactctgg gggtgaatt    49

<210> SEQ ID NO 57
<211> LENGTH: 10
<212> TYPE: DNA
<213> ORGANISM: Synthetic DNA Primers

<400> SEQUENCE: 57
cattcgtgag    10

<210> SEQ ID NO 58
<211> LENGTH: 16
<212> TYPE: DNA
<213> ORGANISM: Synthetic DNA Primers

<400> SEQUENCE: 58
aattctcacg aatgca    16

<210> SEQ ID NO 59
<211> LENGTH: 70
<212> TYPE: DNA
<213> ORGANISM: Synthetic DNA Primers

<400> SEQUENCE: 59
aattcagcgc tgtgcagaga gtactgcggt gtccctgcat gcgcattcag gacctggtac    60
cgcggccgca                                                           70

<210> SEQ ID NO 60
<211> LENGTH: 70
<212> TYPE: DNA
<213> ORGANISM: Synthetic DNA Primers

<400> SEQUENCE: 60
agcttgcggc cgcggtacca ggtcctgaat gcgcatgcag ggacaccgca gtactctctg    60
cacagcgctg                                                           70

<210> SEQ ID NO 61
<211> LENGTH: 67
<212> TYPE: DNA
<213> ORGANISM: Synthetic DNA Primers

<400> SEQUENCE: 61
gctgctgtgc taccccaaga agaggaagga gatggggcgg cctgcaatct ccccatagtc    60
cggggcc                                                              67

<210> SEQ ID NO 62
<211> LENGTH: 63
<212> TYPE: DNA
<213> ORGANISM: Synthetic DNA Primers

<400> SEQUENCE: 62
ccggactatg gggagattgc aggccgcccc atctccttcc tcttctttggg gtagcacagc   60 agc                                                                  63

<210> SEQ ID NO 63
<211> LENGTH: 59
<212> TYPE: DNA
<213> ORGANISM: Synthetic DNA Primers

<400> SEQUENCE: 63
tgaggaagga atacttgaca gtttgagttg cagcatgcaa aattcgaaaa aagtacca      59

<210> SEQ ID NO 64
<211> LENGTH: 60
<212> TYPE: DNA
<213> ORGANISM: Synthetic Synthetic DNA Primers

<400> SEQUENCE: 64
agcttggtac cttttttcga attttgcatg ctgcaactca aactgtcaag tattccttcc    60

<210> SEQ ID NO 65
<211> LENGTH: 91
<212> TYPE: DNA
<213> ORGANISM: Synthetic DNA Primers

<400> SEQUENCE: 65
cgaatccacc cccagagttg ggtgcaccag attgccctga ggatggaggt tctgggctgc    60
gaggcacagg acctctactg aagcttggta c                                   91

<210> SEQ ID NO 66
<211> LENGTH: 85
<212> TYPE: DNA
<213> ORGANISM: Synthetic DNA Primers

<400> SEQUENCE: 66

```
caagcttcag tagaggtcct gtgcctcgca gcccagaacc tccatcctca gggcaatctg      60
gtgcacccaa ctctgggggt ggatt                                            85

<210> SEQ ID NO 67
<211> LENGTH: 11
<212> TYPE: PRT
<213> ORGANISM: Homo Sapiens

<400> SEQUENCE: 67

Ala Val Leu Pro Gln Glu Glu Glu Gly Asp Gly
1               5                   10
```

CELL MEMBRANE-DIRECTED DRUGS

This application is the national phase under 35 U.S.C. §371 of prior PCT International Application No. PCT98/00002 which has an International filing date of Jan. 5, 1998 which designated the United States of America.

TECHNICAL FIELD

This invention relates to drugs in which peptides having affinity specific for phospholipids, preferably those which are contained in the constituents of lipid bilayers forming the surface layers of cells and of which the proportion in the outer part of each lipid bilayer increases when the cell is not normal, for example, in the case where it is damaged, denatured or activated, and biologically active substances bind to each other, deoxyribonucleic acid (DNA) which codes for the amino acid sequence of the drug in the case where the biologically active substance is a peptide, and processes for producing such drugs.

The invention also relates to a novel peptide having affinity specific for a phospholipid, preferably one which is contained in the constituents of lipid bilayers forming the surface layers of cells and of which the proportion in the outer part of each lipid bilayer increases when the cell is not normal, for example, in the case where it is damaged, denatured or activated, more preferably phosphatidylserine or phosphatidylethanolamine, further preferably phosphatidylserine, and DNA coding for the peptide.

The drugs and novel peptides of the invention are useful as preventives and therapeutics of diseases involving coagulopathy, inflammations and immune response.

BACKGROUND ART

Active studies are conducted today in connection with the creation of new drugs of high utility and as one of such studies an attempt is known that is directed to enhance the proportion in which a drug administered in vivo is delivered to the site for effective action while reducing the amount in which it becomes ineffective. This is an attempt at delivery of the drug in a site-specific manner, or an attempt of the so-called "targeting". A representative method of targeting is one that utilizes an antigen-antibody reaction. A method that may be mentioned as an example of this approach is one in which an F(ab')$_2$ fragment of a tumor cell specific antibody (21B2) is bound to liposomes containing adriamycin (ADM) to prepare immunoliposomes such that ADM is delivered on tumor cells [I. Uyama et al., Jpn. J. Cancer Res., Vol. 85, 434 (1994)]. Another representative method of targeting is one that utilizes the interaction between a polypeptide-composed receptor and its ligand. A method that may be mentioned as an example of this approach is one in which an RGD polypeptide sequence having an ability to bind to a GPIIb/GPIIIa receptor is attached to the C terminus of phospholipase A$_2$ (PLA$_2$), whereby the PLA$_2$ is delivered on the membrane surface of platelets (A.C.A.P.A. Bekkers et al., Thrombosis and Haemostasis, Vol. 74, 1138 (1995)). Other examples that have so far been reported include one in which a peptide having affinity for heparin present on the surface of cells is bound to superoxide dismutase (SOD) or complement regulatory proteins such that the SOD is delivered on the cell surface (M. Inoue et al., J. Biol. Chem., Vol. 266, 16409 (1991)) or the complement regulatory proteins is delivered on the cell surface (International Patent Publication WO/96/34965).

Peptides are known which themselves have no biological activity but which have selective affinity to the target site, whereby the binding of a biologically active substances to the target site of action is inhibited through a competitive reaction. An example of such peptides is a polypeptide that binds to a receptor on the surface of cells selectively, thereby inhibiting a ligand from binding to the receptor. An example of such polypeptides is a polypeptide fragment derived from the antigen recognizing site (or complementary determining region: CDR) of an anti-TNFα monoclonal antibody, which inhibits TNFα from binding to a receptor [E. Doring et al., Molecular Immunology, Vol. 31, 1059 (1994)]. Another example is a polypeptide which, by selective binding to a phospholipid, phosphatidylserine, inhibits a factor involved in the progress of a blood coagulation from binding to the phospholipid and which is composed of 30 amino acids at the terminus of the C2 region of a human factor VIII (International Patent Publication WO/90/15615) or 12 amino acids derived from the CDR of a phosphatidylserine recognizing antibody (Japanese Patent Public Disclosure KOKAI No. 92992/1993).

Another example that concerns the creation of new drugs of high utility is an attempt at imparting a new biologically active function to an already biologically active peptide by genetic engineering techniques. As regards TM which is known to suppress a blood clotting reaction, reports have been made of a TM derivative which has a fibrinolytic enzyme such as a tissue plasminogen activator (tPA) bound to a TM peptide (Japanese Patent Domestic Announcement KOHYO 505554/1992) and a TM derivative which has a specified amino acid sequence bound to the C terminus of a TM peptide so as to impart its action in enhancing the activity of antithrombin III and suppressing platelet aggregation (Japanese Patent Public Disclosure KOKAI No. 279497/1994).

DISCLOSURE OF INVENTION

There are known many drugs today that must be used in limited doses because of the side effects they have. For example, heparin and antithrombin III are used as anticoagulants but the use of these substances must occasionally be limited since they have side effects such as the tendency to cause bleeding.

When administering drugs, it is generally required to administer more than a certain dose in order to attain a specified efficacy and side effects to the patient are sometimes a serious problem. In addition, it is by no means rare that administering high doses of drugs will eventually often increase the economic burden on the part of the patient. Therefore, it is desired to develop drugs that have high enough activity to exhibit satisfactory efficacy in low doses such that the side effects from drug administration can be reduced and which can be used more extensively without increasing the economic burden on the patient.

Under the circumstances, the present inventors conducted intensive studies with a view to attaining the stated object. As a result, they found that a drug having affinity for a specified phospholipid that was created by binding a biologically active substance to a substance having affinity for the specified phospholipid had an improved ability to localize on the specified phospholipid, thereby achieving a marked enhancement of its action and efficacy. The inventors further found that this marked enhancement of the action and efficacy of the drug was dependent on the specified phospholipid, which led to the accomplishment of the present invention.

Thus, a first aspect of the present invention is a drug that contains both a substance having affinity for a phospholipid and a biologically active substance. The drug is preferably one having a novel substance that possesses both a portion having affinity for a desired phospholipid and a portion having biologically activity; since the drug is obtained as a different form than it inherently occurs in nature, it is a drug having a chimeric substance or a substance produced by fusion of different proteins. Herein, said affinity for a phospholipid or said portion having affinity for a phospholipid preferably originates from the substance having affinity for a phospholipid, whereas the biological activity or the portion having biological activity preferably originates from the biologically active substance. Specifically, the drug is one that contains both a substance having affinity for a specified phospholipid, preferably phosphatidylserine or phosphatidylethanolamine, more preferably phosphatidylserine, and a biologically active substance. Herein, the substance having affinity for a specified phospholipid is preferably a peptide or a peptide-containing substance. Said peptide has a sequence represented by the following general formula; preferably, it is composed of said sequence. It should be noted that all of the sequences to be described in this specification permit substitution, deletion, addition, insertion and so forth in part of their constituent elements unless their characteristics are impaired. Specifically, if the sequence is an amino acid sequence, one or more amino acids may be substituted, deleted, added, inserted or otherwise modified without impairing the activity of the sequence.

$$(A1)_{n_1}-(A2)_{n_2}-(A3)_{n_3}$$

(provided that in the general formula set forth above, A1 represents the amino acid sequence denoted by SEQ ID NO:1 or 10; A2 and A3 represent the amino acid sequences denoted by SEQ ID NOS:2 and 3, respectively; $n_1$, $n_2$ and $n_3$ which represent the repeating numbers of A1, A2 and A3, respectively, are 0–5, 1–5 and 0–5 respectively; preferably, $n_1$ is 0 or 1, $n_2$ is 1, 2 or 3, and $n_3$ is 0 or 1).

More preferably, the substance having affinity for a phospholipid has at least either of the following sequences:

$(A1)_1-(A2)_1-(A3)_1$ (SEQ ID NO:8 or 9)
$(A2)_1-(A3)_1$ (SEQ ID NO:5)
$(A2)_2-(A3)_1$ (SEQ ID NO:6)
$(A2)_3-(A3)_1$ (SEQ ID NO:7)
$(A2)_2$ (SEQ ID NO:22)

The drug according to the first aspect of the present invention preferably contains a peptide as the biologically active substance; specifically, at least one member selected from the group consisting of a factor involved in a blood coagulation system, a factor involved in a fibrinolytic system, a factor involved in an immune response reaction, a factor suppressing cytopathy, a factor inhibiting the activity of proteases and modified versions thereof, more preferably, at least one member selected from the group consisting of a factor suppressing a blood coagulation, a factor enhancing a fibrinolytic system, a factor suppressing a complement activating reaction, a factor suppressing the cytopathy due to active oxygen, a factor inhibiting the activity of proteases and modified versions thereof, further preferably at least one member selected from the group consisting of TM, the second region of UTI, MCP, UTI and modified versions thereof, particularly preferably a peptide having the amino acid sequence denoted by SEQ ID NO:4 or either of SEQ ID NOS: 23–25.

In a mode of containing both the biologically active substance and the substance having affinity for a specified phospholipid, the drug according to the first aspect of the invention preferably contains a linkage via a peptide bond, more preferably a linkage in which the N terminal amino acid of the substance having affinity for a phospholipid and the C terminal amino acid of the biologically active substance or, alternatively, the C terminal amino acid of the substance having affinity for a phospholipid and the N terminal amino acid of the biologically active substance are associated by a peptide bond, further preferably, a mode in which the N terminal amino acid of the substance having affinity for a phospholipid and the C terminal amino acid of the biologically active substance are associated by a peptide bond.

In its second aspect, the present invention provides a peptide having the amino acid sequence represented by the following general formula:

$$(A2)_{n_2}-(A3)_{n_3}$$

provided that A2 and A3 are the amino acid sequences denoted by SEQ ID NOS:2 and 3, respectively; $n_2$ which is the repeating number of A2 is 2 or 3; $n_3$ which is the repeating sequence of A3 is 0 or 1.

More preferably, the amino acid sequence of said peptide has either of the following sequences:

$(A2)_2-(A3)_1$ (SEQ ID NO:6)
$(A2)_3-(A3)_1$ (SEQ ID NO:7)
$(A2)_2$ (SEQ ID NO:22)

According to its third aspect, the present invention provides DNA coding for the amino acid sequence of the drug according to the first aspect of the present invention or the peptide portion of said drug.

According to its fourth aspect, the present invention provides DNA coding for the amino acid sequence of the peptide according to the second aspect of the invention.

According to its fifth aspect, the present invention provides a process for producing the drug according to the first aspect of the invention.

BRIEF DESCRIPTION OF THE DRAWINGS

FIG. 1 (SEQ ID NOS: 30–38 corresponds respectively to S1–S9) is a diagram showing the DNA primers used in PCR for yielding the DNA of the present invention.

FIG. 2 (SEQ ID NOS: 39–46 corresponds respectively to A1—A8) is a diagram showing the DNA primers used in PCR for yielding the DNA of the present invention.

FIG. 4 (SEQ ID NOS: 47–56 corresponds respectively to F1–F10) is a diagram showing synthetic DNAs used in constructing a vector expressing soluble human TM having affinity for phosphatidylserine, a vector expressing the second region of human UTI having affinity for phosphatidylserine, a vector expressing human UTI having affinity for phosphatidylserine and a vector expressing soluble human MCP having affinity for phosphatidylserine according to the present invention.

FIG. 5 (SEQ ID NOS: 57–66 corresponds respectively to F11–F20) is a diagram showing other synthetic DNAs also used in constructing a vector expressing soluble TM having affinity for phosphatidylserine, a vector expressing the second region of human UTI having affinity for phosphatidylserine, a vector expressing human UTI having affinity for phosphatidylserine and a vector expressing soluble human MCP having affinity for phosphatidylserine according to the present invention.

BEST MODE FOR CARRYING OUT THE INVENTION

Figure 3:
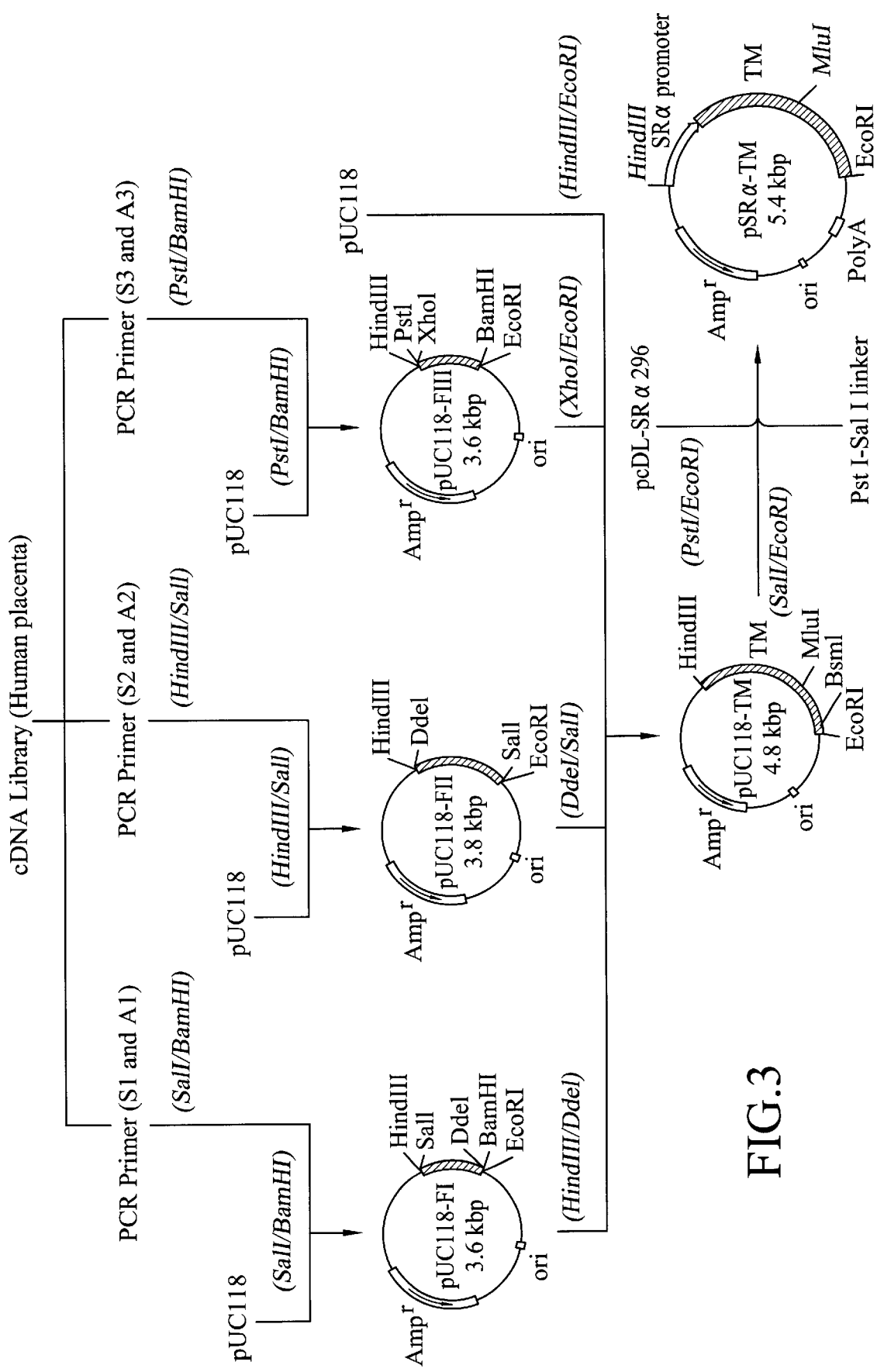
FIG. 3 is a diagram showing the process of cloning human TM cDNA and constructing a human TM expressing vector.

On the pages that follow, the present invention will be described in detail.

The "phospholipid" as used in the present invention is a desired phospholipid that is intended for targeting a biological substance to a specified site and which is contained in the constituent components of the lipid bilayers forming the surface layers of cells such that the proportion of its content in the outer part of each lipid bilayer will increase when the cells are not normal, for example, in the case where they are damaged, denatured or activated. More specifically, the phospholipid is such that its content increases in such cases as where a blood coagulation is in progress, the so-called immune response reactions of cells such as their activation, impairment and/or apotosis due to inflammation or immunocytes are in progress, a cell impairing reaction due to active oxygen is in progress or where a cell activating and/or impairing reaction due to proteases is in progress. As typical examples of such phospholipid, phosphatidylserine and phosphatidylethanolamine (Alan J. Schroit et al., Biochim. Biophys. Acta, Vol. 1071, 313 (1991)) may be mentioned, and phosphatidylserine is preferred.

The term "having affinity" as used in the present invention refers to the performance of a certain interaction. The term "interaction" includes mutual binding, formation of a complex, mutual recognition of molecules, tendency to move and/or aggregate in a specified direction, causing the shape of molecules to change, and mutual reaction. In the case of mutual binding, the mode of binding is in no way limited and it may be non-covalent bonding typified by electrostatic bonding and hydrophobic bonding or covalent bonds typified by a disulfide bond, an ester bond, an ether bond and a peptide bond.

Thus, the first aspect of the present invention is a substance or a composition, preferably a drug, that contain both a substance having affinity for a phospholipid and a biologically active substance, and which are characterized in that their action and efficacy are enhanced under such a condition that a specified phospholipid is present.

The term "under such a condition that a phospholipid is present" as used herein includes not only artificially created environments but also natural environments. Artificially created environments include the state where phospholipids, blood, cells, living tissues and their disrupted products are contained in vitro or within containers such as test tube whereas natural environments include all in vivo parts such as blood vessels, brain and other organs.

It should also be noted that the "peptide" as used in the present invention is in no way limited in the length of its amino acid sequence and covers the range from so-called dipeptides consisting of two amino acids to polypeptides consisting of 1,000 or more amino acids.

The substance having affinity for a phospholipid as used in the present invention is in no way limited in the molecules it is composed of or its shape as long as it has affinity for a specified phospholipid. Preferably, it is a peptide, more preferably a peptide consisting of the following amino acid sequence:

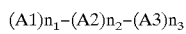

$(A1)n_1-(A2)n_2-(A3)n_3$ where A1 is the amino acid sequence denoted by SEQ ID NO:1 or 10, and A2 and A3 are the amino acid sequences denoted by SEQ ID NOS:2 and 3, respectively. It should be noted that A1 may contain all or part of the amino acid sequence denoted by SEQ ID NO:1. For example, A1 may contain the amino acid sequence denoted by SEQ ID NO:10 but it preferably contains all of the amino acid sequence of SEQ ID NO:1. Symbol Xaa in SEQ ID NO:2 is Thr or Leu. It should also be noted that A3 may contain part or all of the amino acid sequence of SEQ ID NO:3. Referring to $n_1$, $n_2$ and $n_3$, they are any numbers representing the repeating numbers of the amino acid sequence A1, A2 and A3, respectively; $n_1$ is preferably 5 or less, more preferably 0 or 1, $n_2$ is preferably at least 1, more preferably 1, 2 or 3, and $n_3$ is preferably 5 or less, more preferably, 0 or 1.

The method of combining the sequences set forth above is not limited in any way as long as the stated peptide has affinity for a specified phospholipid. Advantageous examples to be combined include the sequences denoted by SEQ ID NOS:5–9 and 22.

It should, however, be noted that the aforementioned amino acid sequences are illustrative only and the peptide having affinity for a specified phospholipid according to the present invention is in no way limited in its amino acid sequence as long as it has affinity for a specified phospholipid and depending on the need, the aforementioned amino acid sequences may be subjected to substitution, deletion, insertion, addition and so forth. Further, they may be modified as required. Alternatively, peptides having affinity for phosphatidylserine that consist of entirely different amino acid sequences from the aforementioned ones may be substituted, for example, a peptide derived from a Gla region (characterized by γ-carboxyglutamic acid residue) which has affinity for the phosphatidylserine contained in a coagulation-related factor such as factor Xa (Mann K. G. et al., Blood, Vol. 76, 1 (1990)), a peptide having affinity for the phosphatidylserine derived from factor V [Thomas L. O. et al., J. Biol. Chem., Vol. 267, 4189 (1992)], a peptide having affinity for the phosphatidylserine derived from Annexin V (M. A. Swairjo et al., Nature Struct. Biol., Vol. 2, 968 (1995)), and so forth or derivatives thereof.

The "biologically active substance" in the drug of the present invention may be of any substance that exhibits a pharmacological action in vivo and it may include a peptide having a biological activity, a chemical substance exhibiting a pharmacological action, as well as their aggregates, encapsulations and so forth, a peptide with being preferred. The "peptide having biological activity" mentioned herein may be any peptide that is involved in in vivo reactions and it may be modified, as required. Preferably, the biologically active substance is a peptide which inherently makes a certain mutual interaction with cell membranes by itself or a peptide that interacts with substances that occur within cells, on cell membranes, in the surface layers of cells or their surroundings; modified versions, variants and derivatives of such peptides are also included. If the biologically active substance is an inherently non-water-soluble peptide, as exemplified by some membrane proteins, it may optionally be modified to a water-soluble form. Advantageous examples of such peptides include a factor involved in a blood coagulation system, a factor involved in a fibrinolytic system, a factor involved in immune response, a factor suppressing cytopathy, a factor inhibiting the activity of proteases and so forth, more preferably, a factor suppressing a blood coagulation system, a factor enhancing a fibrinolytic system, a factor suppressing a complement activating reaction, a factor suppressing the cytopathy due to active hydrogen, a factor inhibiting the activity or proteases and so forth. To illustrate in greater detail, examples of the factor involved in a blood coagulation system and/or the factor suppressing a blood coagulation system include TM, the second region of UTI, antithrombin III (ATIII), a tissue factor pathway inhibitor (TFPI) and so forth, as well as modified versions, variants and derivatives of these factors. Examples of the factor involved in a fibrinolytic system and/or the factor enhancing a fibrinolytic system include tPA, urokinase (UK) and so forth, as well as modified versions, variants and derivatives of these factors. Examples of the factor involved in immune response reactions include complement regulatory proteins such as MCP and a decay-accelerating factor (DAF) which are factors that suppress a complement activating reaction, UTI which inhibits immunocyte-derived proteases and the second region of UTI, as well as modified versions, variants and derivatives of these factors. Examples of the factor suppressing the cytopathy due to active oxygen and/or the factor inhibiting the activity of proteases include UTI, the second region of UTI, elafin, a secretory leukoprotease inhibitor (SLPI) and so forth, as well as modified versions, variants and derivatives of these factors. Other examples of the factor suppressing the cytopathy due to active oxygen include SOD, catalase and so forth, as well as their modified versions, variants and derivatives (i.e., factors having an active oxygen scavenging action). Among these advantageous examples, TM, the second region of UTI, MCP and UTI, as well as their modified versions, variants and derivatives are preferred, and those peptides which are represented by SEQ ID NOS:4 and 23–25 are particularly preferred. These are illustrative only and will in no way limit the biologically active substance to be used in the present invention.

In the drug according to the first aspect of the present invention, the "chemical substance exhibiting a pharmacological action" is a substance selected from among all substances that exhibit pharmacological actions but which exclude peptides having biological activity and as long as it exhibits a pharmacological action in vivo, it will in no way be limited by the molecular formula with which it is denoted. Specifically, examples include artificially synthesized compounds, chemical substances obtained by separation from natural products and microorganism-produced substances, nucleic acids, saccharides, lipids and so forth, as well as their modified versions. To illustrate in greater detail, cyclophosphamide which is an immunosuppressive substance, actinomycin D which is an anti-cancer agent, an antisense oligonucleotide, hyaluronic acid and lecithin may be mentioned; it should be noted that these are merely intended for illustrative purposes and will in no way limit the biologically active substance to be used in the present invention.

The term "aggregate" of the substance having biological activity or the compound exhibiting a pharmacological action covers the substance having biological activity or the compound exhibiting a pharmacological action which have been assembled in a quantity greater than a specified level due, for example, to chemical bonding or physical adhesion, and the term "encapsulation" of the substance having biological activity or the compound exhibiting a pharmacological action covers the substance having biological activity or the chemical compound exhibiting a pharmacological action which are incorporated within liposomes, microcapsules or high-molecular weight matrices and so forth.

The mode in which both the substance having affinity for a phospholipid and the biologically active substance are contained according to the first aspect of the present invention is not limited in any particular way. A preferred mode is such that the substance having affinity for a phospholipid is substantially integral with the biologically active substance to form the drug of the present invention without causing a complete compromise in the affinity for a specified phospholipid which is possessed by the substance having affinity for a phospholipid or in the activity of the biologically active substance. As long as the substance having affinity for a phospholipid is substantially integral with the biologically active substance to form the drug of the present invention without causing a complete compromise in the affinity for a specified phospholipid which is possessed by the substance having affinity for a phospholipid or in the activity of the biologically active substance, all possible modes such as a mixture, a composition, a complex, a bound form and so forth are included. Thus, the two substances may be simply mixed with each other or they may be contained in a composition or, alternatively, they may perform interaction with each other. The term "interaction" covers mutual binding, formation of a complex, mutual recognition of molecules, tendency to move and/or aggregate in a specified direction, causing the state of molecules to change and mutual reaction, with direct or indirect bonding in either of these forms being preferred. In the case of mutual binding, the mode of binding is in no way limited and it may be non-covalent bonding typified by electrostatic bonding and hydrophobic bonding or covalent bonding typified by a disulfide bond, an ester bond, an ether bond and a peptide bond. Depending on the need, a suitable linker and an adapter such as a peptide having any amino acid sequence or any compound may be interposed, as exemplified by a biotin-avidin bond, an antibody-antigen bond or a bond formed by a receptor and its ligand; further, modifications may be applied as required. If at least one of the biologically active substance and the substance having affinity for a phospholipid is a peptide, examples of the binding site in the peptide include an amino group, a carboxyl group and a thiol group in a cysteine residue that are present at the N terminus, C terminus or inside chains, with the N- or C terminus being preferred. In a particular case where both the biologically active substance and the substance having affinity for a phospholipid are peptides, it is preferred to contain a bond established by a peptide bond and a more preferred mode is such that the N terminus of either one of the biologically active substance and the substance having affinity for a phospholipid is bound to the C terminus of the other peptide via a peptide bond. Thus, chimeric proteins and fused proteins may be mentioned as typical examples. Among these cases, the one in which the N terminus of the substance having affinity for a phospholipid is linked to the C terminus of the biologically active substance via a peptide bond is particularly preferred. To give a specific preferred example, a drug according to the present invention may be mentioned that contains a peptide composed of an amino acid sequence in which an amino acid sequence selected from among SEQ ID NOS:5–9 and 22 is linked to the C terminus of an amino acid sequence selected from among SEQ ID NOS:4 and 23–25.

The present invention also provides a novel peptide having affinity for phosphatidylserine which consists of or contains the amino acid sequences denoted by SEQ ID NOS:6, 7 and 22, as well as a pharmaceutical that contains said peptide as a component. Said pharmaceutical includes one in which the novel peptide having affinity for phosphatidylserine according to the present invention is mixed with or bound to a biologically active substance or its aggregate or encapsulation. The biologically active substance with or to which the novel peptide having affinity for phosphatidylserine has mixed or bound, or the aggregate or encapsulation of the substance has such a nature that it will be delivered selectively on the surface of cells that are not normal, as exemplified by damaged, denatured or activated cells. States more specifically, a biologically active substance to which the novel peptide having affinity for phosphatidylserine according to the present invention has bound, optionally via a suitable linker, has such a nature that it will be delivered selectively on the surface of cells that are not normal, as exemplified by damaged, denatured or activated cells. The novel peptide having affinity for phosphatidylserine according to the present invention may be modified with a substance having affinity for the constituent components of the skeleton of an encapsulation of a biologically active substance and subsequently mixed or reacted with the encapsulation of the biologically active substance to produce an encapsulation containing the biologically active substance to the surface of which the novel peptide having affinity for phosphatidylserine has bound and this encapsulation similarly has such a nature that it will be delivered selectively on the surface of cells that are not normal, as exemplified by damaged, denatured or activated cells. To illustrate, if the biologically active substance is contained in liposomes, the novel peptide having affinity for phosphatidylserine according to the present invention is modified with a suitable phospholipid such as phosphatidylethanolamine and thereafter mixed with liposomes to produce a drug in which the novel peptide having affinity for phosphatidylserine according to the present invention has bound to the surface layers of the liposomes and the drug has such a nature that it will be delivered selectively on the surface of cells that are not normal, as exemplified by damaged, denatured or activated cells.

The novel peptide having affinity for phosphatidylserine according to the present invention can also be used as a drug with which a biologically active factor that is involved in the progress of a blood coagulation is inhibited from binding to the target site of action by a competitive reaction.

The DNA of the present invention may be of any kind as long as it has, in effect, a DNA sequence coding for the peptides of the substance having affinity for a phospholipid and/or the biologically active substance which compose the drug of the present invention. More specifically, the present invention provides DNA which contains, preferably consists of, the following sequences:

$$(J1)-(D1)_m-(D2)_{m_2}-(D3)_{m_3}-(J1)$$

where J1 is a DNA sequence coding for the amino acid sequence of a peptide having biological activity and at least either one of 5'- or 3' terminus will be sufficient; D1, D2 and D3 are DNA sequences coding for the peptides represented by A1, A2 and A3, respectively, with D1 being the DNA sequence denoted by SEQ ID NO:11 or 12, D2 the DNA sequence denoted by SEQ ID NO:13 or 14, and D3 the DNA sequence denoted by SEQ ID NO:15. It should be noted that D1 may contain all or part of the DNA sequence of SEQ ID NO:11 to such an extent that there will be no change in its translational frame. For instance, D1 may contain the DNA sequence of SEQ ID NO:12 and it preferably contains all of the DNA sequence of SEQ ID NO:11. Symbol M in SEQ ID NOS:13 and 14 signifies A or C. It should also be noted that D3 may contain part or all of the DNA sequence of SEQ ID NO:15 to such an extent that there will be no change in its translational frame. Symbols ml, $m_2$ and $m_3$ are any numbers that represent the repeating numbers of the DNA sequences, D1, D2 and D3, respectively; $m_1$ is preferably 5 or less, more preferably 0 to 1, $m_2$ is preferably at least 1, more preferably 1, 2 or 3, and $m_3$ is preferably 5 or less, more preferably 0 to 1. The method of combining the stated sequences is in no way limited as long as the peptides composed of the amino acid sequences translated from the stated DNA provide the drug of the present invention. To give advantageous examples, J1 may be DNA coding for a factor involved in a blood coagulation, a factor involved in a fibrinolytic system, a factor involved in immune response, a factor suppressing cytopathy, a factor inhibiting the activity of proteases and so forth, more preferably, a factor suppressing a blood clotting reaction, a factor enhancing a fibrinolytic system, a factor suppressing a complement activating reaction, a factor suppressing the cytopathy due to active oxygen, a factor inhibiting the activity of proteases and so forth. To illustrate in greater detail, examples of the factor involved in a coagulation system reaction and/or the factor suppressing a blood coagulation include TM, the second region of UTI, ATIII, TFPI and so forth, as well as modified versions, variants and derivatives of these factors. Examples of the factor involved in a fibrinolytic system and/or the factor enhancing a fibrinolytic system include tPA, UK and so forth, as well as modified versions, variants and derivatives of these factors. Examples of the factor involved in an immune response reactions include complement regulatory proteins such as MCP and DAF which are factors suppressing a complement activating reaction, UTI which inhibits immunocyte-derived proteases and the second region of UTI, as well as modified versions, variants and derivatives of these factors. Examples of the factor suppressing the cytopathy due to active oxygen and/or the factor inhibiting the activity of proteases include UTI, the second region of UTI, SLPI and so forth, as well as modified versions, variants and derivatives of these factors. Other examples of the factor suppressing the cytopathy due to active oxygen include SOD, catalase and so forth, as well as their modified versions, variants and derivatives (i.e., factors act as active oxygen scavenger). A typical example of a more preferred combination of sequences may be a DNA sequence consisting of nucleotide sequences such that a nucleotide sequence of SEQ ID NOS:16–20 or No. 26 is linked to the 3' end of a nucleotide sequence of SEQ ID NO:21 and SEQ ID NOS:27–29.

Advantageous examples of the DNA according to the fourth aspect of the present invention which codes for the amino acid of the novel peptide having affinity for phosphatidylserine are the DNA sequences of SEQ ID NOS:17, 18 and 26 (which code for the peptides of SEQ ID NO:6, 7 and 22, respectively).

The present invention also provides a recombinant DNA, such as a plasmid or expression vector, that contains the DNA of the invention.

As is well known in the art, in accordance with the degeneracy of genetic codes, at least one base in the DNA gene sequence which encodes polypeptide can be replaced by another base without changing its amino acid sequence. Hence, the DNA of the present invention may have base sequences having one or more base replacements based on the degeneracy of genetic codes. Particularly in the case of producing the peptide of the present invention by genetic engineering techniques, the DNA may have sequences having one or more base replacements in order to provide codons that will be used with high frequency in specified host cells. It should be noted that in the present invention, the sequence of DNA is described starting from the 5' terminal end. In the present invention, A, G, C and T stand for deoxyadenylic acid, deoxyguanylic acid, deoxycytidylic acid and thymidylic acid, respectively.

The drug of the present invention can be obtained by a process in which the substance having affinity for a specified phospholipid and the biologically active substance are prepared individually and then mixed or bound to each other. Herein, the substance having affinity for a specified phospholipid may be mixed with or bound to the biologically active substance by any method as long as the substance having affinity for a specified phospholipid is substantially integral with the biologically active substance to form the drug of the present invention without causing a complete compromise in the affinity for a specified phospholipid which is possessed by the substance having affinity for a specified phospholipid or in the activity of the biologically active substance.

The substance having affinity for a specified phospholipid according to the present invention is preferably a peptide and can be produced by a process characterized in that at least one of the following steps is performed:

a) the step of obtaining said peptide by chemical synthesis;
b) the step of obtaining DNA having a sequence coding for the amino acid sequence of said peptide;
c) the step of incorporating said DNA into a vector so as to give a replicable recombinant DNA containing said DNA;
d) the step of transforming a host cell with said recombinant DNA to give a transformant capable of expressing said peptide; and
e) the step of culturing said transformant such as to produce said peptide and recovering said peptide from the culture mixture.

The chemical synthesis method for producing a peptide having a specified amino acid sequence according to the present invention may typically be implemented by using an automatic peptide synthesizer.

The DNA having a sequence coding for the peptide of the present invention may typically be prepared in the following manner. Unless otherwise expressly stated, general genetic engineering techniques can be implemented on the basis of the procedures described in literature (such as "Molecular Cloning, A LABORATORY MANUAL", Second Edition, T. Maniatis et al., Cold Spring Harbor Laboratory Press (1989)). To begin with, cDNA prepared on the basis of mRNA extracted from human cells or organs or, alternatively, a commercially available human cDNA library or human chromosomal DNA is used as template DNA. Then, by referring to the known DNA sequence (e.g., the sequence of human factor VIII) and using a DNA probe chemically synthesized with an automatic DNA synthesizer, the template DNA is screened to obtain DNA coding for the desired polypeptide.

The DNA coding for a polypeptide having affinity for a specified phospholipid can also be obtained solely by chemical synthesis using an automatic DNA synthesizer. Another preferred method for obtaining the DNA coding for a peptide having affinity for a specified phospholipid is one utilizing a polymerase chain reaction (hereinafter designated as PCR). Briefly, by referring to the known DNA sequence (e.g., the sequence of human factor VIII), a DNA primer is chemically synthesized with optional base sequences and restriction enzyme recognizing sites being attached as required and PCR is performed using the above-mentioned cDNA as a template DNA such that the desired DNA is obtained. It should be noted that PCR can be performed by making reference to literature (e.g., "PCR Protocols, A Guide to Methods and Applications", Michael A. I. et al., Academic Press (1990)).

The step of incorporating the DNA of interest into a vector can be implemented in accordance with the general genetic engineering techniques described in the stated literature. Briefly, cloning sites in the vector are digested with suitable restriction enzymes and the DNA of interest, optionally after digestion with restriction enzymes, is inserted between the digested cloning sites, optionally with linkers and so forth. The vector to be used herein may be of any kind as long as it is capable of replication within the host to be used but it is preferred to select a vector that contains a promoter, a ribosome binding site, sequence of a signal peptide and/or a poly(A)$^+$ signal, all being necessary for expressing the peptide of interest within a host, and which is replicable within the host to be used. As the promoter, ribosome binding site, sequence of signal peptide and poly(A)$^+$ signal that are to be used, all promoters, ribosome binding sites, sequence of signal peptide and poly(A)$^+$ signals that will function within the host to be used are applicable and these can be synthesized chemically or are available from any cells, host to be used, virus, plasmid or phage and so forth.

The step of introducing the resulting recombinant DNA into a host cell can be implemented in accordance with the methods customary in the art concerned and which are described in literature (e.g. "Shin Saibo Kogaku Jikken Purotokol", edited by Department of Oncology, Institute of Medical Science, The University of Tokyo, published by Shujunsha, 1991), as exemplified by a competent cell procedure, a calcium phosphate procedure, a DEAE dextran procedure or electroporation and so forth. The host cell into which the resulting recombinant DNA is to be introduced may be eukaryotic as typified by Hela cell, COS cell, CHO cell, yeasts and insect cells or prokaryotic as typified by *Escherichia coli* and *Bacillus subtilis* and any cell that is suitable for expressing the peptide of the present invention may be selected as appropriate and subsequently used. It should also be noted that the host cell and the vector are advantageously used in such a combination that they are mutually functional to be capable of expressing DNA coding for the peptide of interest. Examples of the preferred vector-host combination include the combination of COS cell or CHO cell with a vector containing the early promoter of simian virus 40 (SV40), a vector containing EF-1α promoter (EF promoter) or a vector containing SRα promoter and so forth, the combination of yeast *Saccharomyces cerevisiae* with a vector containing the promoter of a 3-phosphoglycerate kinase gene and so forth, as well as the combination of *E. coli* HB101 with a vector containing tryptophan promoter derived *E. Coli.*

The host transformed with the expression vector can be cultured using nutrient media in accordance with known general methods for culturing microorganisms, animal cells or insect cells. The peptide of interest produced by the transformed host can be purified, isolated and recovered from the culture broth by making reference to many articles and literature (e.g., "Shin Seikagaku Jikken Koza 1. Tanpakushitsu I", edited by The Japanese Biochemical Society, published by Tokyo Kagaku Dojin, 1990)). Briefly, the peptide of interest can be obtained in a pure form using at least one method selected from among desalting, concentration, salting out, ultrafiltration, ion-exchange chromatography, reverse-phase chromatography, isoelectric chromatography, affinity chromatography, and gel filtration.

A peptide having biological activity can be obtained by the same procedures as those described above for obtaining the peptide having affinity for a specified phospholipid. Briefly, human TM, for instance, can be obtained by chemical synthesis or using genetic engineering or by the combination of both.

A chemical substance exhibiting a pharmacological action can be obtained by chemical synthesis. If it is difficult to obtain by chemical synthesis or if the cost for chemical synthesis is exorbitant, it may be extracted, separated or purified from natural products or it may be separated and purified from the supernatant of the culture broth of a microorganism.

If the drug of the present invention is such that both the biologically active substance and the substance having affinity for a phospholipid are peptides and that the N terminus of either one of the peptides and the C terminus of the other are joined linearly by a peptide bond, with a peptide of a given length being optionally interposed as a linker, the drug can be directly obtained by a process characterized in that at least one of the following steps is performed:

a) the step of obtaining a peptide having the amino acid sequence of the drug of interest by chemical synthesis;
b) the step of obtaining DNA having a sequence coding for the amino acid sequence of the drug of interest;
c) the step of incorporating said DNA into a vector so as to give a replicable recombinant DNA containing said DNA;
d) the step of transforming a host cell with said recombinant DNA to give a transformant capable of expressing the peptide of interest;
e) the step of culturing said transformant to produce the peptide of interest and recovering said peptide from the culture broth.

The peptide having the amino acid sequence of the drug of interest can be obtained by chemical synthesis, typically using an automatic peptide synthesizer.

The DNA having a sequence coding for the amino acid sequence of the drug of interest may typically be prepared in the following manner. Unless otherwise expressly stated, general genetic engineering techniques can be implemented on the basis of the procedures described in literature (such as "Molecular Cloning, A LABORATORY MANUAL", Second Edition, T. Maniatis et al., Cold Spring Harbor Laboratory Press (1989)). To begin with, cDNA prepared on the basis of mRNA extracted from human cells or organs, a commercially available human cDNA library or human chromosomal DNA is used as template DNA. Then, by referring to the known DNA sequence of a peptide having biological activity (e.g. human TM DNA), the template DNA is screened using a DNA probe chemically synthesized with an automatic DNA synthesizer to obtain DNA (I) that codes for part or all of the peptide having biological activity. DNA (I) can also be obtained by chemical synthesis alone using an automatic DNA synthesizer. Similarly, DNA (II) can be produced that codes for a peptide having affinity for a specified phospholipid (e.g. the C-terminal region of human factor VIII). Another preferred method for obtaining DNA (I) and DNA (II) is one utilizing PCR. Briefly, by referring to the known DNA sequence (e.g., human TM DNA or human factor VIII DNA), a DNA primer is chemically synthesized with optional sequences and restriction enzyme recognizing sites being attached as required, and PCR is performed using the above-mentioned cDNA as a template DNA such that the desired DNA is obtained. It should be noted that PCR can be performed by making reference to literature (e.g., "PCR Protocols, A Guide to Methods and Applications", Michael A. I. et al., Academic Press (1990)). The thus obtained DNA (I) and DNA (II) are optionally digested with restriction enzymes and bound together, with a chemically synthesized DNA linker being optionally interposed, thereby yielding a DNA fragment containing the DNA coding for the drug of the present invention.

The step of incorporating the stated DNA into a vector so as to give a replicable recombinant DNA containing said DNA, the step of transforming a host cell with said recombinant DNA to give a transformant capable of expressing the drug of interest, and the step of culturing said transformant to produce the drug of interest and recovering said drug from the culture broth can be implemented by the same procedures as those described above for obtaining the peptide having affinity for a specified phospholipid.

If the novel peptide having affinity for phosphatidylserine according to the present invention is bound to a biologically active substance or its aggregate or encapsulation, there is provided a means of enabling the biologically active substance or its aggregate or encapsulation to be delivered selectively on the surface of cells that are not normal, as exemplified by damaged, denatured or activated cells. Take, for example, the case where the biologically active substance is contained within encapsulations, the substance having affinity for a specified phospholipid is modified with a substance having affinity for the components making up the skeleton of the encapsulations and thereafter mixed with the encapsulations containing the biologically active substance, whereby said substance having affinity for a specified phospholipid is bound to the surfaces of the encapsulations to yield the drug of the present invention. To give a preferred example for the case where the biologically active substance is contained within liposomes, the substance having affinity for a specified phospholipid is modified with a suitable phospholipid such as phosphatidylethanolamine and thereafter mixed with the liposomes, whereby the substance having affinity for a specified phospholipid is bound to the surface layer of each liposome to yield the drug of the present invention.

The substances or drug of the present invention, for example, the substances to be described in the Examples were not found to have any significant toxicity.

In addition, the drug of the present invention may appropriately be combined with pharmaceutical carriers and media such as sterilized water, biological saline, vegetable oils, mineral oils, higher alcohols, higher fatty acids and innocuous organic solvents, etc. and further with optional excipients, coloring agents, emulsifiers, suspending agents, surfactants, solubilizers, anti-adsorbents, stabilizers, preservatives, humectants, antioxidants, buffering agents, isotonic solutions, palliatives, etc. so as to take the form of pharmaceutical compositions (e.g., injections and oral drugs) or kits. The drug of the present invention can be administered systemically or topically and either rapidly or in a sustained manner, preferably by peroral routes, for example, by intravenous injection, intracoronary injection, intramuscular injection, intraperitoneal injection or subcutaneous injection, etc. However, the use of the drug of the present invention is by no means limited to these methods of administration. In addition, it may be used in combination with other drugs.

The dose of administration of the drug of the present invention can be adjusted as appropriate for the biologically active substance contained in said drug and depending upon the severity of the disease the patient is suffering from.

The present invention also provides a novel method for delivery of the biologically active substance in a site-selective manner so as to enhance its action and efficacy by a marked degree. Stated more specifically, the present invention provides a method by which the substance having affinity for a specified phospholipid is bound to the desired biologically active substance so that the latter is delivered on the surface layer of cells to exhibit an enhanced action and efficacy. Herein, the phospholipid which serves as targeted molecules to deliver the biologically active substance consists of molecules that compose cell membranes which are possessed by all cells without exception and, in this respect, it is totally different from the aforementioned specific antigens as the specific receptors, molecules and so forth which are composed of polypeptides. Therefore, all cells, as well as all tissues and organs that are composed of cells can potentially provide sites where the activity of the biologically active substance in the drug of the present invention will increase. In addition, if the affinity conferred on the biologically active substance is for a specified phospholipid, the activity of the biologically active substance can be selectively increased in certain of the cells and in certain of the tissues and organs that are composed of the cells. Thus, the present invention provides a drug delivery method or system based on the entirely new concept that the action and efficacy of a biologically active substance is enhanced by its selective delivery on the surface layers of cells, tissues and organs that are not normal. As will be described in the Examples, the present inventors prepared substances having affinity for a phospholipid, in which a peptide having affinity for a phospholipid was bound to TM, UTI, the second region of UTI or MCP. As it turned out, the TM having affinity for a phospholipid, the UTI having affinity for a phospholipid and the second region of UTI having affinity for a phospholipid were sufficiently increased in their activity and ability of being localized on phospholipid to exhibit an enhanced action and efficacy. The increase in activity and ability of being localized on phospholipid can also be verified for the MCP having affinity for a phospholipid by measuring its action in suppressing complement-dependent hemolysis as described in a literature ("Hotaigaku", Inai M. et al., published by Ishiyaku Shuppan Kabushiki Kaisha, 1982). The Examples provide illustrations of a drug delivery method or system that are based on the aforementioned entirely new concept that the action and efficacy of a biologically active substance is enhanced by selective aggregation of said substance on the surface layers of cells, tissues and organs at various sites such as a site where a blood coagulation is in progress, a site where the so-called immune response reactions of cells such as their activation and impairment due to inflammation or immunocytes are in progress, and a site impaired by active oxygen, and a site where a cell activation and impairing reaction is in progress due to active proteases. In summary, the present invention provides a drug and a novel peptide that are useful as preventives and therapeutics of diseases involving coagulopathy, inflammations and immune response reactions, as well as DNA necessary for producing them and a process for producing said drug. It should be noted that the drug of the present invention is by no means limited to pharmaceuticals and may be used as clinical or research reagents and the like.

The present invention will now be described below more specifically by means of working examples, which are given herein for the mere purpose of illustrating the practice of the invention and are in no way intended to limit the same. The abbreviations used in the following description are based on those which are conventional in the art concerned.

Unless otherwise noted, genetic engineering technology was implemented adopting the protocols described in books such as "Molecular Cloning, A LABORATORY MANUAL", Second Edition, T. Maniatis et al., Cold Spring Harbor Laboratory Press (1989), "A Practical Guide to Molecular Cloning", 2nd Edition, Bernard Perb et al., John Wiley & Sons (1988), "PCR Protocols, A Guide to Methods and Applications", Michael A. I. et al., Academic Press (1990), "Shin Saibo Kogaku Jikken Purotokol", edited by Department of Oncology, Institute of Medical Science, University of Tokyo, published by Shujunsha, 1991, and "Idenshi Kogaku Handobukku", edited by Muramatsu M. et al., published by Yodosha, 1991, as well as the protocols attached to the reagents or equipment used.

The *E. coli* strains bearing pM1354 and pM1357, respectively, which were expression plasmids for the rsT-MTd and rsTMC2 disclosed in the Examples were deposited with the National Institute of Bioscience and Human-Technology, Agency of Industrial Science and Technology, 1–3, Higashi 1 chome, Tsukuba-shi, Ibaraki-ken, JAPAN under date of Dec. 16, 1996 (under respective Accession Numbers P-16008 and P-16009) and a transfer from the original deposit to an international deposit was effected under date of Dec. 8, 1997 (under respective Accession Numbers FERM BP-6194 and FERM BP-6195). The *E. coli* strain bearing pM851 which was an expression plasmid for human MCP was deposited with the National Institute of Bioscience and Human-Technology, Agency of Industrial Science and Technology, 1–3, Higashi 1 chome, Tsukuba-shi, Ibaraki-ken, JAPAN under date of Jan. 22, 1992 (under Accession Number P-12715) and a transfer from the original deposit to an international deposit was effected under date of Feb. 18, 1993 (under Accession Number FERM BP-4195).

EXAMPLE 1

Chemical Synthesis of Peptides Having Affinity for Phosphatidylserine

Peptides having the amino acid sequence of SEQ ID NOS:5, 6 and 22 were synthesized by a solid-phase method using an automatic peptide synthesizer (Model 432A, product of Applied Biosystems). Unless otherwise expressly stated, the operating methods were in accordance with the attached operating manual. Following cleavage, deprotection and precipitation in ether, peptides were obtained by removing the ether and the resulting residues were freeze-dried. The freeze-dried peptides were dissolved in 10% acetonitrile with 0.1% trifluoroacetic acid, and using a C18 column (CAPCELLPACC18AG120, product of Shiseido Co., Ltd.) and high-performance liquid chromatography (625LC System, product of Waters), the peptides were purified by a 10%–60% acetonitrile with 0.1% trifluoroacetic acid linear density gradient.

The yields of the respective peptides were 10 mg, 6 mg and 12 mg.

EXAMPLE 2

Cloning of Human TM cDNA and Preparation of Human TM Expressing Plasmids

Total RNA was isolated from about 20 g of human placenta by a guanidium isothiocyanate method. A portion (10 mg) of the resulting RNA was passed twice through a oligo(dT)-cellulose column (type 7, product of Pharmacia) to recover about 90 $\mu$g of poly(A)$^+$ RNA. Then, using the resulting poly(A)$^+$ RNA as a starting material, single-stranded cDNA was synthesized. Briefly, single-stranded cDNA was synthesized by means of a reverse transcriptase using 10 $\mu$g of the poly(A)$^+$ RNA as a template and an oligo(dT) as a primer in the usual manner.

In a separate step, by referring to a known sequence of human TM DNA (K. Suzuki et al., EMBO J., Vol. 6, 1891 (1987) and R. W. Jackman et al., Proc. Natl. Acad. Sci. USA, Vol. 84, 6425 (1987)), six DNA primers (S1–S3 and A1–A3; see FIGS. 1 and 2), each corresponding to a portion of the DNA sequence of the human TM gene and containing a suitable restriction enzyme recognition site at 5' end, were synthesized with a chemical synthesizer (Model 381, product of Applied Biosystems). As for S3, a restriction enzyme XhoI recognition site was introduced by silent mutation. Speaking of A3, it contained a DNA sequence corresponding to a termination codon. The synthesized DNA primers were purified on an OPC column (product of Applied Biosystems).

Then, using the aforementioned single-stranded cDNA as template DNA, PCR was performed using the chemically synthesized DNA primers in accordance with the reaction solution's recipe shown in Table 1, and the human TM cDNA was amplified in three divided portions (for the correspondence between the DNA primers used and the DNA to be amplified, see Table 2). DNA amplification was performed with a thermal cycler (Model PJ1000, product of Perkin-Elmer Cetus) by repeating 30 reaction cycles, each consisting of 94° C.×1 min, 55° C.×2 min and 72° C.×3 min; after the end of the reaction, a portion of the reaction solution was sampled and subjected to agarose gel electrophoresis, which verified the amplification of the intended sizes of DNA.

TABLE 1

| PCR Reaction Solution's Recipe | |
| --- | --- |
| Distilled water | 77 $\mu$L |
| Buffer*) | 10 $\mu$L |
| dNTPs mixed solution (2.5 mM) | 8 $\mu$L |
| Sense primer (1 $\mu$g/$\mu$L) | 1 $\mu$L |
| Antisense primer (1 $\mu$g/$\mu$L) | 1 $\mu$L |
| Template DNA (ca. 20 ng/$\mu$L) | 2.5 $\mu$L |
| Heat-resistant DNA polymerase (5 units/$\mu$L) | 0.5 $\mu$L |
| Total | 100 $\mu$L |

*)Buffer:
0.1 M Tris-HCl (pH = 8.3)
0.5 M KCl
15 mM MgCl$_2$

TABLE 2

| Combinations of Sense and Antisense Primers vs Amplified Genes | | | |
| --- | --- | --- | --- |
| | Sense primer | Antisense primer | Amplified DNA |
| Combination I | S1 | A1 | Fragment I |
| Combination II | S2 | A2 | Fragment II |
| Combination III | S3 | A3 | Fragment III |

The amplified DNA (Fragments I–III) were purified and recovered from the reaction solution by a phenol/chloroform treatment and ethanol precipitation. Fragments I, II and III were digested with restriction enzyme pairs SalI/BamHI, HindIII/SalI and PstI/BamHI, respectively, and thereafter subcloned into a cloning vector pUC118 in the usual manner to give pUC118-FI, pUC118-FII and pUC118-FIII. Subsequently, pUC118-FI was digested with a restriction enzyme pair HindIII/DdeI, pUC118-FII with DdeI/SalI and pUC118-FIII with XhoI/EcoRI and subjected to agarose gel electrophoresis in the usual manner, whereby DNA fragments of ca. 450 bp, ca. 650 bp and ca. 650 bp were separated and recovered. The three recovered DNA fragments and the product of digestion of pUC118 with a restriction enzyme pair HindIII/EcoRI were ligated in the usual manner to prepare a plasmid pUC118-TM bearing a full length of human TM cDNA containing a signal peptide (the process of construction of the plasmid is shown in FIG. 3). In the usual manner, the sequence determination of the cDNA obtained was carried out with a DNA sequencer (370A, product of Applied Biosystems), whereupon it was verified to be human TM cDNA.

In the next step, pUC118-TM was digested with restriction enzymes SalI and EcoRI and subjected to agarose gel electrophoresis in the usual manner, thereby separating a DNA fragment in pure form having a length of about 1.7 kbp. The fragment was inserted between cloning sites, PstI and EcoRI, in a mammalian cell expression vector pcDL-SRα 296 (Y. Takebe et al., Mol. Cell. Biol., Vol. 8, 466 (1988)) together with PstI-SalI linker (5'-TCGATGCA-3') that had been synthesized with a chemical synthesizer (supra) and purified on an OPC column (supra), thereby constructing a human TM expressing vector pSRα-TM (the process of its construction is shown in FIG. 3).

EXAMPLE 3
Preparation of Plasmids Expressing Soluble Human TM Having Affinity of Phosphatidylserine
(1) Preparing pM1350

Figure 6:
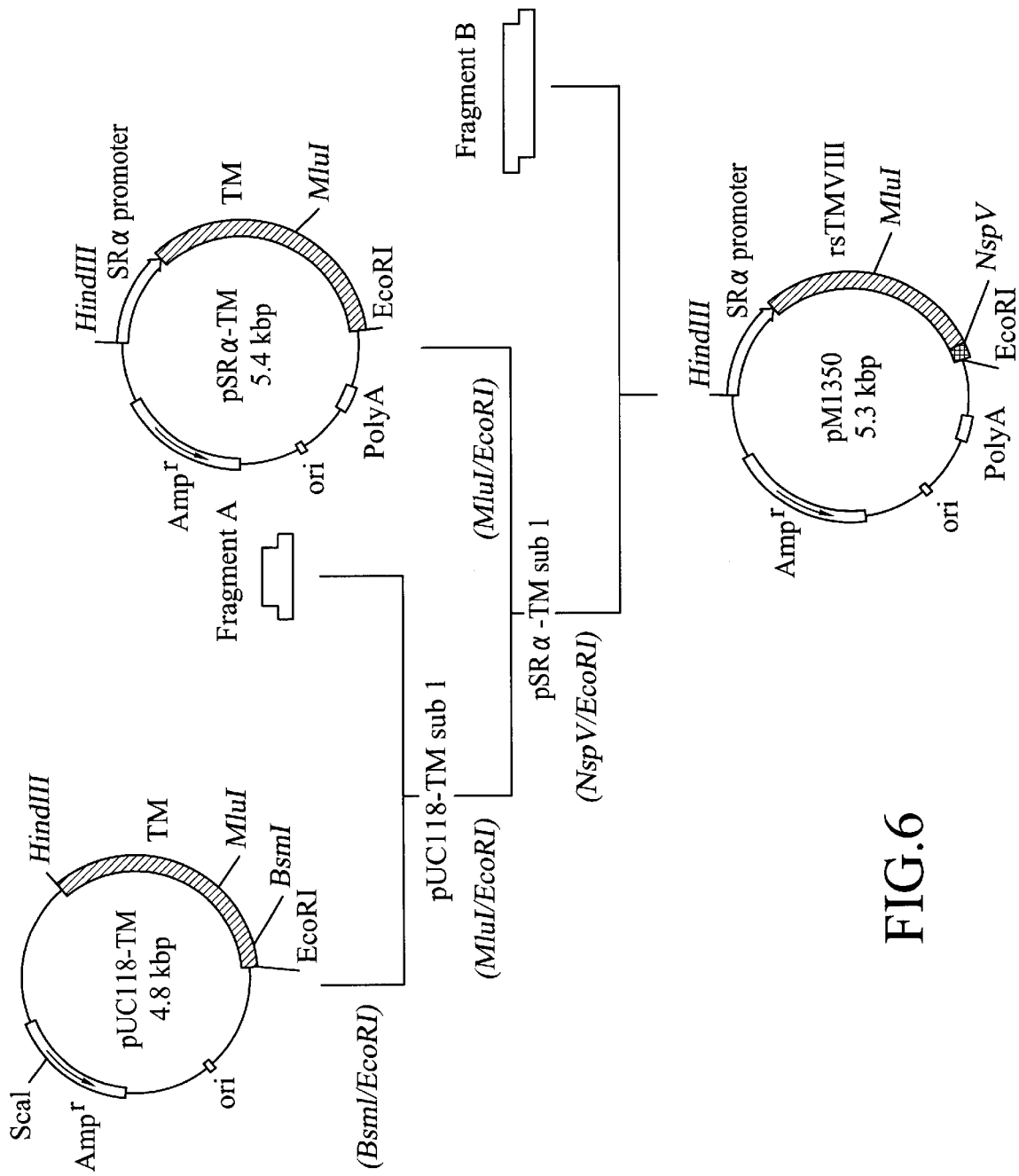
FIG. 6 is a diagram showing the process of constructing an expression vector pM1350 according to the present invention.

Four species of single-stranded DNA (F1–F4; see FIG. 4) were synthesized with a chemical synthesizer (supra) and F1 and F2 were annealed in the usual manner and so were F3 and F4, thereby yielding DNA fragment A which was ca. 30 bp in length and which has a BsmI cleaved surface at 5' end and an EcoRI cleaved surface at 3' end, as well as DNA fragment B which was ca. 90 bp in length and which had an NspV cleaved surface at 5' end and an EcoRI cleaved surface at 3' end. Then, the pUC118-TM prepared in Example 2 was digested with restriction enzymes BsmI and EcoRI and subjected to agarose gel electrophoresis, thereby separating and recovering a DNA fragment of ca. 4.6 kbp. This DNA fragment was ligated with fragment A in the usual manner to yield pUC118-TM sub1. Subsequently, the pUC118-TM sub1 was digested with restriction enzymes MluI and EcoRI and subjected to agarose gel electrophoresis, thereby separating and recovering a DNA fragment of ca. 0.8 kbp. In a separate step, the pSRα-TM prepared in Example 2 was digested with restriction enzymes MluI and EcoRI and subjected to agarose gel electrophoresis, thereby separating and recovering a DNA fragment of ca. 4.4 kbp. The two DNA fragments of ca. 0.8 kbp and ca. 4,4 kbp in length were ligated in the usual manner to yield pSRα-TM sub1. Further, the pSRα-TM sub1 was digested with restriction enzymes NspV and EcoRI and subjected to agarose gel electrophoresis, thereby separating and recovering a DNA fragment of ca. 5.2 kbp. This DNA fragment was ligated with fragment B in the usual manner to yield pM1350 (the process of its construction is shown in FIG. 6). This plasmid contained DNA consisting of a nucleotide sequence in which the nucleotide sequence of SEQ ID NO:16 was linked to the 3' side of the nucleotide sequence of SEQ ID NO:21; using this plasmid, one can produce soluble human TM having affinity for phosphatidylserine which is a peptide consisting of an amino acid sequence in which the amino acid sequence of SEQ ID NO:5 is linked to the C terminus of the amino acid sequence of SEQ ID NO:4 (said soluble human TM is hereinafter designated as rsTMVIII).

(2) Preparing pM1357

By referring to a known DNA sequence of human factor VIII [William I. Wood et al., Nature, Vol. 312, 330 (1984)], a total of four DNA primers, two of them corresponding to a portion of the DNA sequence of the human factor VIII (S4 and A4; see FIGS. 1 and 2 and two others (S5 and A5; see FIGS. 1 and 2) which corresponded to another portion of the DNA sequence of the human factor VIII and which contained a suitable restriction enzyme recognition site at 5' end, were synthesized with a chemical synthesizer (supra).

It should be added that A5 contained a DNA sequence corresponding to a termination codon. The synthesized DNA primers were purified on an OPC column (supra).

Then, using the single-stranded cDNA synthesized using the human placental poly(A)$^+$ RNA in Example 2 as template DNA, cDNA coding for a region including the C2 region of human factor VIII was amplified by PCR using chemically synthesized DNA primers S4 (as sense primer) and A4 (as antisense primer) by means of the same reaction solution as identified in Table 1. DNA amplification was performed with a thermal cycler (supra) by repeating 40 reaction cycles, each consisting of 94° C.×1 min, 55° C.×2 min and 72° C.×3 min; after the end of the reaction, a portion of the reaction solution was sampled and subjected to agarose gel electrophoresis, which at least verified the amplification of the intended size of DNA.

Subsequently, using the resulting DNA fragment produced by PCR as template DNA, PCR was performed using chemically synthesized DNA primers S5 (as sense primer) and A5 (as antisense primer) by means of the same reaction solution as identified in Table 1, thereby selectively amplifying cDNA coding for the C2 region of human factor VIII. DNA amplification was performed with the thermal cycler (supra) by repeating 30 reaction cycles, each consisting of 94° C.×1 min, 55° C.×2 min and 72° C.×3 min; after the end of the reaction, a portion of the reaction solution was sampled and subjected to agarose gel electrophoresis, which verified the amplification of the intended size of DNA.

Figure 7:
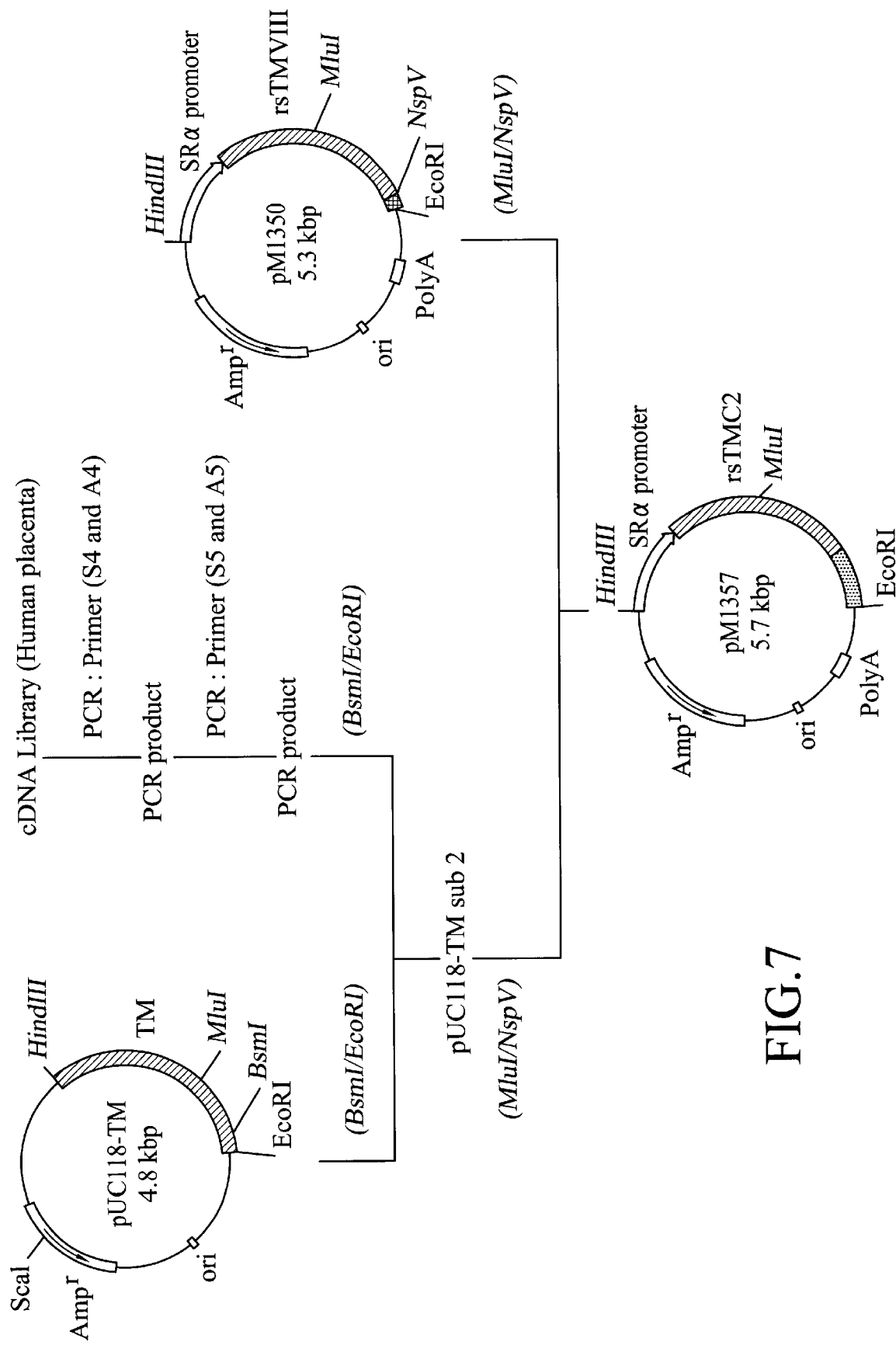
FIG. 7 is a diagram showing the process of constructing an expression vector pM1357 according to the present invention.

The amplified DNA was purified and recovered from the reaction solution by a phenol/chloroform treatment and ethanol precipitation; the recovered DNA was digested with restriction enzymes BsmI and EcoRI to yield a DNA fragment ca. 0.5 kbp in length which had a BsmI cleaved surface at 5' end and an EcoRI cleaved surface at 3' end. Then, the pUC118-TM prepared in Example 2 was digested with restriction enzymes BsmI and EcoRI and subjected to agarose gel electrophoresis, thereby separating and recovering a DNA fragment of ca. 4.6 kbp. This DNA fragment was ligated with the previously obtained DNA fragment ca. 0.5 kbp in length in the usual manner to yield pUC118-TM sub2. Subsequently, the pUC118-TM sub2 was digested with restriction enzymes MluI and NspV and subjected to agarose gel electrophoresis, thereby separating and recovering a DNA fragment of ca. 1.2 kbp. In a separate step, the pM1350 prepared in Example 3(1) was digested with restriction enzymes MluI and NspV and subjected to agarose gel electrophoresis, thereby separating and recovering a DNA fragment of ca. 4.5 kbp. The two DNA fragments ca 1.2 kbp and ca. 4.5 kbp in length were ligated in the usual manner to yield pM1357 (the process of its construction is shown in FIG. 7). This plasmid contained DNA consisting of a nucleotide sequence in which the nucleotide sequence of SEQ ID NO:20 was linked to the 3' side of the nucleotide sequence of SEQ ID NO:21; using this plasmid, one can produce soluble human TM having affinity for phosphatidylserine which is a peptide consisting of an amino acid sequence in which the amino acid sequence of SEQ ID NO:9 is linked to the C terminus of the amino acid sequence of SEQ ID NO:4 (said soluble human TM is hereinafter designated as rsTMC2).

(3) Preparing pM1356

By referring to known DNA sequence of human factor VIII (supra), one DNA primer (S6. see FIG. 1) which corresponded to a portion of the DNA sequence of human factor VIII and which contained a suitable restriction enzyme recognition site at 5' end was synthesized with a chemical synthesizer (supra). The synthesized DNA primer was purified on an OPC column (supra).

Then, using the DNA fragment which coded for a region including the C2 region of human factor Viii that was amplified by PCR using DNA primer S4 and A4 in Example 3(2) as template DNA, PCR was performed with the same reaction solution as identified in Table 1 using chemically synthesized DNA primer S6 (as sense primer) and DNA primer A5 (as antisense primer) synthesized in Example 3(2), thereby selectively amplifying a DNA fragment coding for 60 amino acids at the C terminus of the C2 region of human factor VIII. DNA amplification was performed with a thermal cycler (supra) by repeating 30reaction cycles, each consisting of 94° C.×1 min, 55° C.×2 min and 72° C.×3 min; after the end of the reaction, a portion of the reaction solution was sampled and subjected to agarose gel electrophoresis, which verified the amplification of the intended size of DNA.

Figure 8:
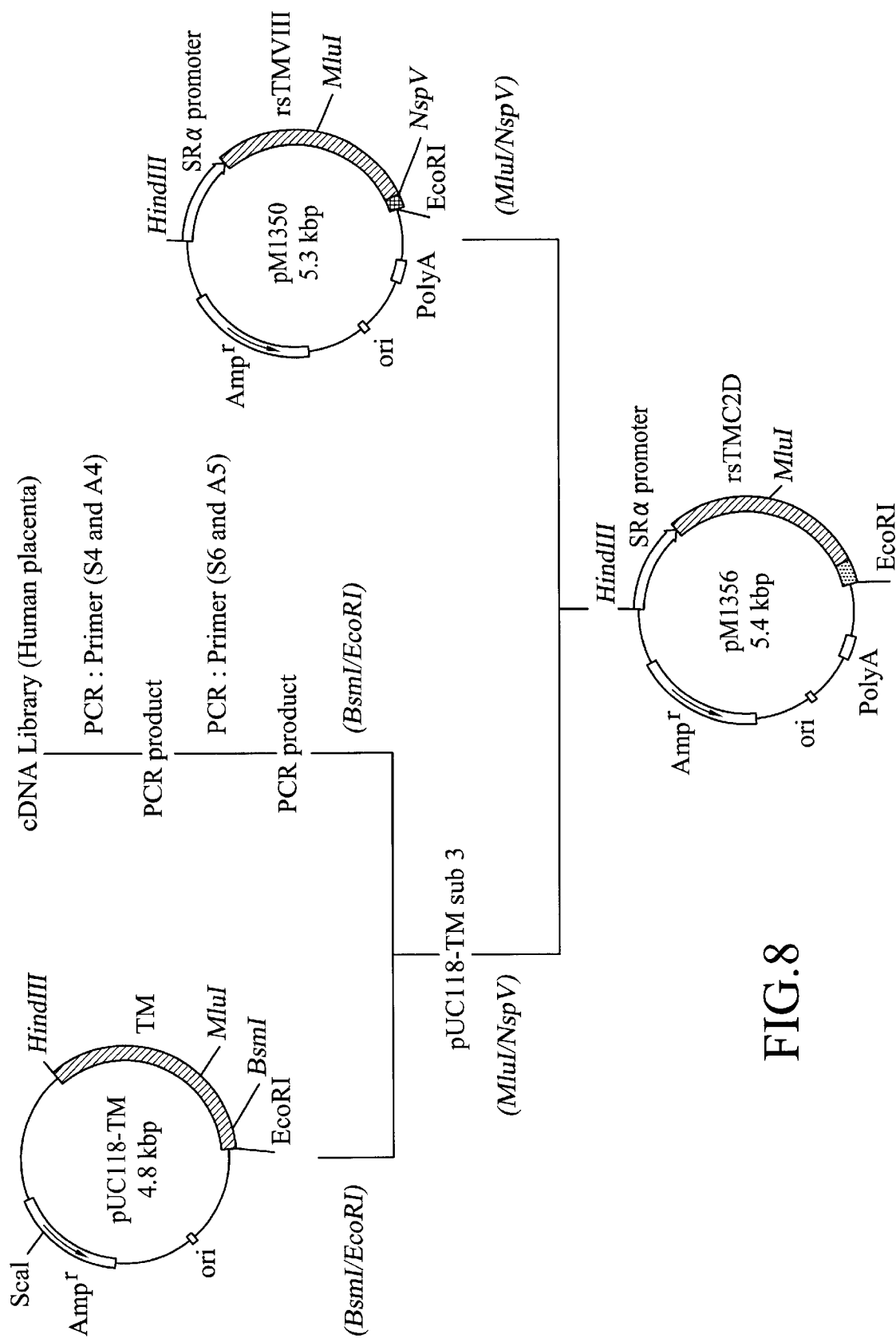
FIG. 8 is a diagram showing the process of constructing an expression vector pM1356 according to the present invention.

The amplified DNA was purified and recovered from the reaction solution by a phenol/chloroform treatment and ethanol precipitation; the recovered gene was digested with restriction enzymes BsmI and EcoRI to yield a DNA fragment ca. 0.2 kbp in length which had a BsmI cleaved surface at 5' end and an EcoRI leaved surface at 3' end. Then, the pUC118-TM prepared in Example 2 was digested with restriction enzymes BsmI and EcoRI and subjected to agarose gel electrophoresis, thereby separating and recovering a DNA fragment of ca. 4.6 kbp. This DNA fragment was ligated with the previously prepared DNA fragment about 0.2 kbp in length in the usual manner to yield pUC118-TM sub3. Subsequently, the pUC118-TM sub3 was digested with restriction enzymes MluI and NspV and subjected to agarose gel electrophoresis, thereby separating and recovering a DNA fragment of ca. 0.9 kbp. In a separate step, the pM1350 prepared in Example 3(1) was digested with restriction enzymes MluI and NspV and subjected to agarose gel electrophoresis, thereby separating and recovering a DNA fragment of ca. 4.5 kbp. The two DNA fragments of ca. 0.9 and ca. 4.5 kbp in length were ligated in the usual manner to yield pM1356 (the process of its construction is shown in FIG. 8). This plasmid contained DNA consisting of a nucleotide sequence in which the nucleotide sequence of SEQ ID NO:19 was linked to the 3' side of the nucleotide sequence of SEQ ID NO:21; using this plasmid, one can produce soluble human TM having affinity for phosphatidylserine which is a peptide consisting of an amino acid sequence in which the amino acid sequence of SEQ ID NO:8 is linked to the C terminus of the amino acid sequence of SEQ ID NO:4 (said soluble human TM is hereinafter designated as rsTMC2D).

(4) Preparing pM1354

Figure 9:
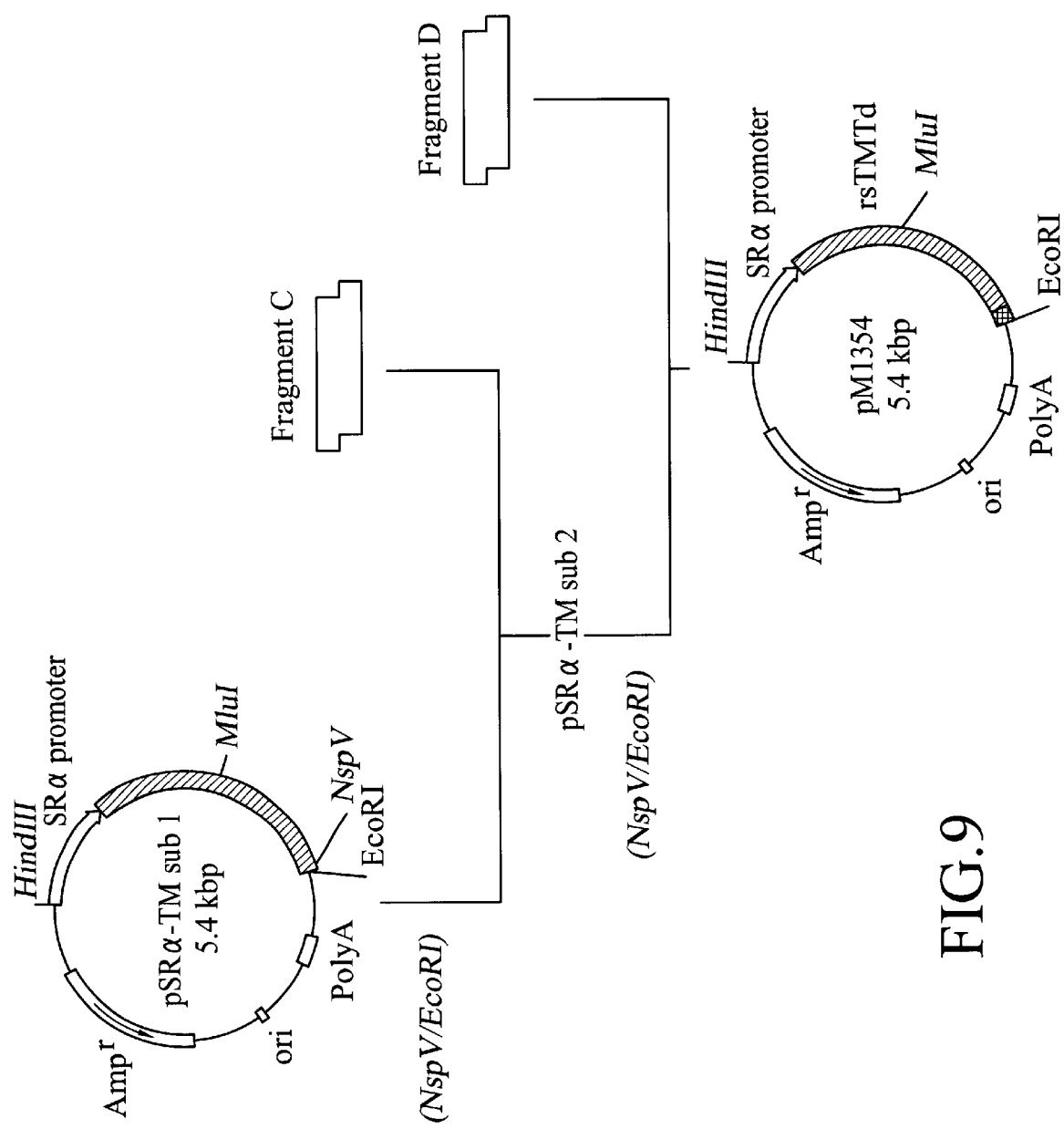
FIG. 9 is a diagram showing the process of constructing a vector pM1354 according to the present invention.

Four species of single-stranded DNA (F5–F8; see FIG. 4) were synthesized with a chemical synthesizer (supra) and F5 and F6 were annealed in the usual manner and so were F7 and F8, thereby yielding DNA fragment C which was ca. 60 bp in length and which had an NspV cleaved surface at 5' end and an EcoRI cleaved surface at 3' end, as well as DNA fragment D which was ca. 90 bp in length and which had an NspV cleaved surface at 5' end and an EcoRI cleaved surface at 3' end. Then, the pSRα-TM sub1 prepared in Example 3(1) was digested with restriction enzymes NspV and EcoRI and subjected to agarose gel electrophoresis, thereby separating and recovering a DNA fragment of ca. 5.2 kbp. This fragment was ligated with fragment C in the usual manner to yield pSRα-TM sub2. Subsequently, the pSRα-TM sub2 was digested with restriction enzymes NspV and EcoRI and subjected to agarose gel electrophoresis, thereby separating and recovering a DNA fragment of ca. 5.3 kbp. This fragment was ligated with fragment D in the usual manner to yield pM1354 (the process of its construction is shown in FIG. 9). This plasmid contained DNA consisting of a nucleotide sequence in which the nucleotide sequence of SEQ ID NO:17 was linked to the 3' side of the nucleotide sequence of SEQ ID NO:21; using this plasmid, one can produce soluble human TM having affinity for phosphatidylserine which is a peptide consisting of an amino acid sequence in which the amino acid sequence of SEQ ID NO:6 is linked to the C terminus of the amino acid sequence of SEQ ID NO:4 (said soluble human TM is hereinafter designated as rsTMTd).

(5) Preparing pM1355

Figure 10:
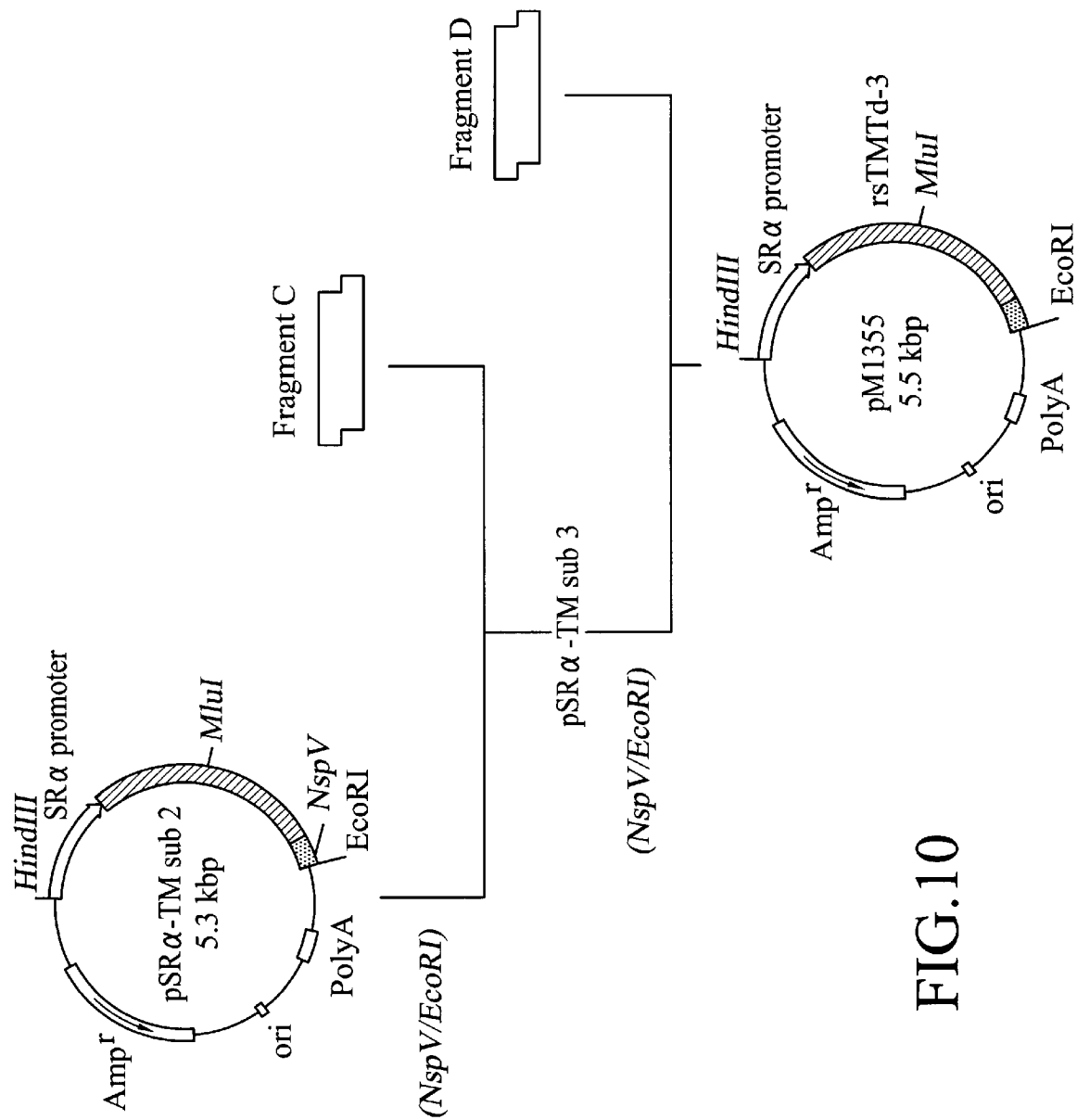
FIG. 10 is a diagram showing the process of constructing an expression vector pM1355 according to the present invention.

The pSRα-TM sub2 prepared in Example 3(4) was digested with restriction enzymes NspV and EcoRI and subjected to agarose gel electrophoresis, thereby separating and recovering a DNA fragment of ca. 5.3 kbp. This DNA fragment and fragment C prepared in Example 3(4) were ligated in the usual manner to thereby yield pSRα-TM sub3. Subsequently, the pSRα-TM sub3 was digested with restriction enzymes NspV and EcoRI and subjected to agarose gel electrophoresis, thereby separating and recovering a DNA fragment of about 5.4 kbp. This fragment and the fragment D prepared in Example 3(4) were ligated in the usual manner to yield pM1355 (the process of its construction is shown in FIG. 10). This plasmid contained DNA consisting of a nucleotide sequence in which the nucleotide sequence of SEQ ID NO:18 was linked to the 3' side of the nucleotide sequence of SEQ ID NO:21; using this plasmid, one can produce soluble human TM having affinity for phosphatidylserine which is a peptide consisting of an amino acid sequence in which the amino acid sequence of SEQ ID NO:7 is linked to the C terminus of the amino acid sequence of SEQ ID NO:4 (said soluble human TM is hereinafter designated as rsTMTd-3).

(6) Preparing pM1358

Figure 14:
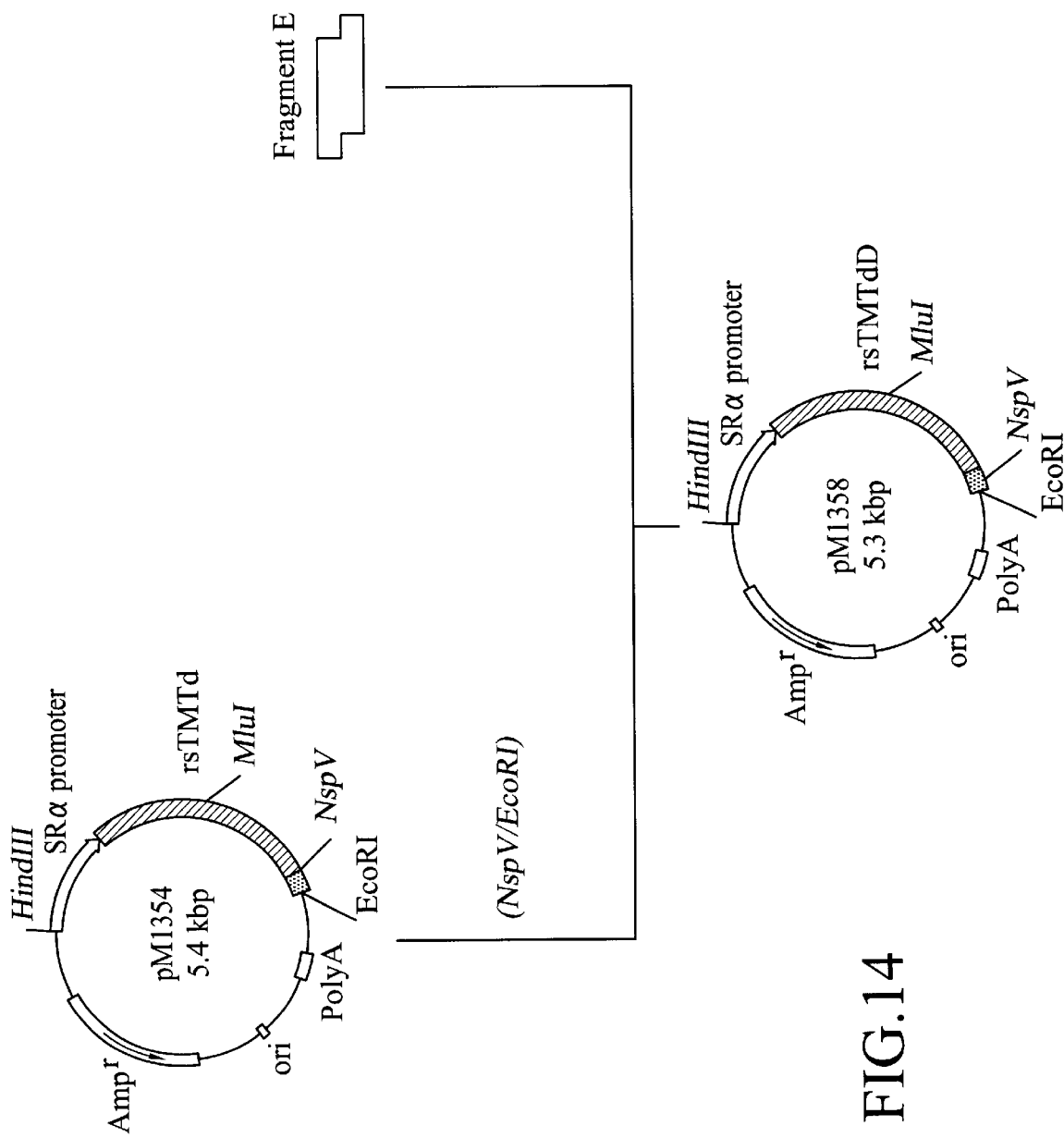
FIG. 14 is a diagram showing the process of constructing an expression vector pM1358 according to the present invention.

Two species of single-stranded DNA (F9 and F10; see FIG. 4) were synthesized with a chemical synthesizer (supra) and F9 and F10 were annealed in the usual manner to yield DNA fragment E ca. 60 bp in length which had an NspV cleaved surface at 5' end and an EcoRI cleaved surface at 3' end. Then, the pM1354 prepared in Example 3(4) was digested with restriction enzymes NspV and EcoRI and subjected to agarose gel electrophoresis, thereby separating and recovering a DNA fragment of ca. 5.3 kbp. This fragment was ligated with fragment E in the usual manner to yield pM1358 (the process of its construction is shown in FIG. 14). This plasmid contained DNA consisting of a nucleotide sequence in which the nucleotide sequence of SEQ ID NO:26 was linked to the 3' side of the nucleotide sequence of SEQ ID NO:21; using this plasmid, one can produce soluble human TM having affinity for phosphatidylserine which is a peptide consisting of an amino acid sequence of SEQ ID NO:22 is linked to the C terminus of the amino acid sequence of SEQ ID NO:4 (said soluble human TM is hereinafter designated as rsTMTdD.

EXAMPLE 4
Preparing Unmodified Soluble TM Expressing Plasmid

Two species of single-stranded DNA (F11 and F12; see FIG. 5) were synthesized with a chemical synthesizer (supra) and both were annealed in the usual manner to yield DNA fragment F ca. 20 bp in length which had a BsmI cleaved surface at 5' end and an EcoRI cleaved surface at 3' end. Then, the pUC118-TM prepared in Example 2 was digested with restriction enzymes BsmI and EcoRI and subjected to agarose gel electrophoresis, thereby separating and recovering a DNA fragment of ca. 4.6 kbp. This fragment was ligated with fragment F in the usual manner to yield pUC118-sTM. Subsequently, the pUC118-sTM was digested with restriction enzymes MluI and EcoRI and subjected to agarose gel electrophoresis, thereby separating and recovering a DNA fragment of ca. 0.8 kbp. In a separate step, the pSRα-TM prepared in Example 2 was digested with restriction enzymes MluI and EcoRI and subjected to agarose gel electrophoresis, thereby separating and recovering a DNA fragment of ca. 4.4 kbp. The two DNA fragments of ca. 0.8 kbp and ca. 4.4 kbp in length were ligated in the usual manner to yield pM1399. This plasmid contained DNA having the base sequence of SEQ ID NO:21; using this plasmid, one can produce unmodified soluble human TM of SEQ ID NO:4 (which is hereinafter designated as rsTM).

EXAMPLE 5
Expressing rsTMVIII, rsTMC2, rsTMC2D, rsTMTd, rsTMTd-3, rsTMTdD and rsTM Each of the plasmids prepared in Examples 3 and 4, i.e., pM1350, pM1357, pM1356, pM1354, pM1355, pM1358 and pM1399, was transfected into COS-1 cells (ATCCCRL-1650) by a DEAE dextran method (adapted from the method described in Lauren M. Sompayrac et al., Proc. Natl. Acad. Sci. USA, Vol. 78, 7575 (1981)), thereby expressing soluble human TM having affinity for phosphatidylserine and unmodified soluble human TM. Stated more specifically, ca. $3 \times 10^5$ cells/9 $cm^2$ were inoculated in plastic tissue culture plate and cultivated at 37° C. for one day in 2 mL of a Dulbecco modified Eagle's medium (hereinafter abbreviated as DMEM) containing 10% fetal calf serum. After washing three times with 2 mL of DMEM, culture medium was replaced by 0.7 mL of DMEM containing 1 μg of each of the plasmids, 50 mM Tris-HCl (pH 7.4), 0.2 mg/mL of DEAE dextran and 150 μM chloroquine. After cultivation at 37° C. for 4 h, the culture solution was removed by suction; after washing once with 2 mL of DMEM and once with DMEM containing 10% fetal calf serum, 2 mL of DMEM containing 10% fetal calf serum was added and cultivation was continued at 37° C. for 24 h. Thereafter, the culture medium was replaced by DMEM containing 0.1% BSA and cultivation was continued at 37° C. for an additional 72 h, and the supernatant of the culture solution was collected. It was found that collected culture solution contained various types of soluble human TM having affinity for phosphatidylserine (rsTMVIII, rsTMC2, rsTMC2D, rsTMTd, rsTMTd-3 and rsTMTdD) and unmodified human soluble TM (rsTM) in amounts of 1–5 μg/mL.

The collected culture solution was desalted and concentrated using an ultrafiltration membrane having a molecular weight cutoff value of $3 \times 10^4$. After pH was adjusted to 7.5, the concentrate was passed through a DIP-thrombin-agarose column preconditioned with 0.02 Tris-HCl buffer containing 0.1 M NaCl, 1 mM benzamidine hydrochloride, 0.5 mM $CaCl_2$ and 0.5% Triton X-100, whereby active fractions were adsorbed on the column. Then, after washing with the same buffer as used for preconditioning, the active fractions were eluted by a 0.1–1 M NaCl linear density gradient using 0.02 M Tris-HCl buffer containing 0.1 mM EDTA, 1 mM benzamidine hydrochloride and 0.5% Triton X-100; thus, various types of soluble human TM having affinity for phosphatidylserine (i.e., rsTMVIII, rsTMC2, rsTMC2D, rsTMTd, rsTMTd-3 and rsTMTdD) and unmodified soluble human TM (rsTM) were obtained in pure form.

EXAMPLE 6
Preparing Liposomes

Liposomes were prepared from different phospholipids in accordance with the method of Kaneda, Y [Jikken Igaku, Vol. 12, 184 (1994)]. Stated more specifically, 10 mg of phosphatidylserine (derived from bovine brain and product of Sigma), 10 mg of phosphatidylcholine (derived from egg yolk and product of Sigma), 10 mg of phosphatidylethanolamine (from bovine brain and product of Sigma) or 10 mg of phosphatidic acid (derived from egg yolk and product of Sigma), each being dissolved in chloroform, was charged into an egg plant type flask either individually or in admixture. After drying under nitrogen gas, 50 μL of 10 mM potassium phosphate solution and 450 μL of tetrahydrofuran were added and the pospholipid was redissolved in the same egg plant type flask. The flask was fitted on a rotary evaporator (Model REN-1, product of Iwaki Glass Co., Ltd.) and dried under the vacuum as it was whirled in a water bath at 45° C., whereupon thin phospholipid films formed on the inner glass surface of the flask. Following the addition of 200 μL of 30 mM Tris-imidazole buffer (pH 8.4) containing 20 mM $CaCl_2$ and 0.22 M NaCl (the buffer is hereinafter abbreviated as TIBS), the flask was shaken vigorously for 30 seconds with a vortex mixer and left to stand at 37° C. in a constant temperature bath for 30 seconds; the process of vigorous shaking and subsequent standing was repeated 8 times. The flask was then placed in a water tank in an ultrasonic cleaner (Model UT-53, product of Sharp Corp.) and sonicated for 5 seconds; thereafter, the flask was shaken vigorously for 30 seconds with the vortex mixer and 300 μL of TIBS (supra) was added, followed by 30-min shaking in a constant temperature bath equipped with a shaker to prepare a liposome solution. The solution contained 20 mg/mL of a phospholipid of interest in the form of liposomes.

EXAMPLE 7
Measuring the Ability to Accelerate the Activation of Protein C

Measurements of the ability to accelerate the activation of protein C in the absence of phospholipids were conducted in accordance with the method of Takahashi et al. [Thrombosis and Haemostasis, Vol. 73, 805 (1995)]. Stated more specifically, 75 μL of TIBS (supra) and 25 μL of TIBS containing 40 U/mL of bovine thrombin (product of Mochida Pharmaceutical Co., Ltd.) were mixed either with 25 μL of the supernatant of the culture of COS-1 cells in which each of the soluble human TM species having affinity for phosphatidylserine which are described in Example 5 was expressed, optionally after dilution with the supernatant of the culture of COS-1 cells, or with 25 μL of the supernatant of the culture of COS-1 cells in which unmodified soluble human TM was expressed, optionally after dilution with the supernatant of the culture of COS-1 cells, and the mixture was heated at 37° C. for 10 minutes. Then, 25 μL of TIBS containing 12 U/mL of human protein C (product of American Diagnostica) was added and reaction was performed at 37° C. for 10 minutes followed by the addition of 100 μL of TIBS containing 0.15 U/mL of antithrombin III (product of The Green Cross Corp.) and 15 U/mL of heparin (product of Mochida Pharmaceutical Co., Ltd.) to terminate the protein C activation reaction. The termination reaction was continued at 37° C. for 10 minutes; thereafter, 250 μL of TIBS containing 3.2 mM of synthetic substrate S-2366 (product of Daiichi Pure Chemicals Co., Ltd.) was added and reaction was performed at 37° C. for 5 minutes. Subsequently, 1.5 mL of 50% aqueous acetic acid was added so that all reactions would terminate and the concentration of the synthetic substrate cleaved with the activated protein C was measured with a spectrophotometer (DU640, product of Beckman) at a wavelength of 405 nm.

Figure 11:
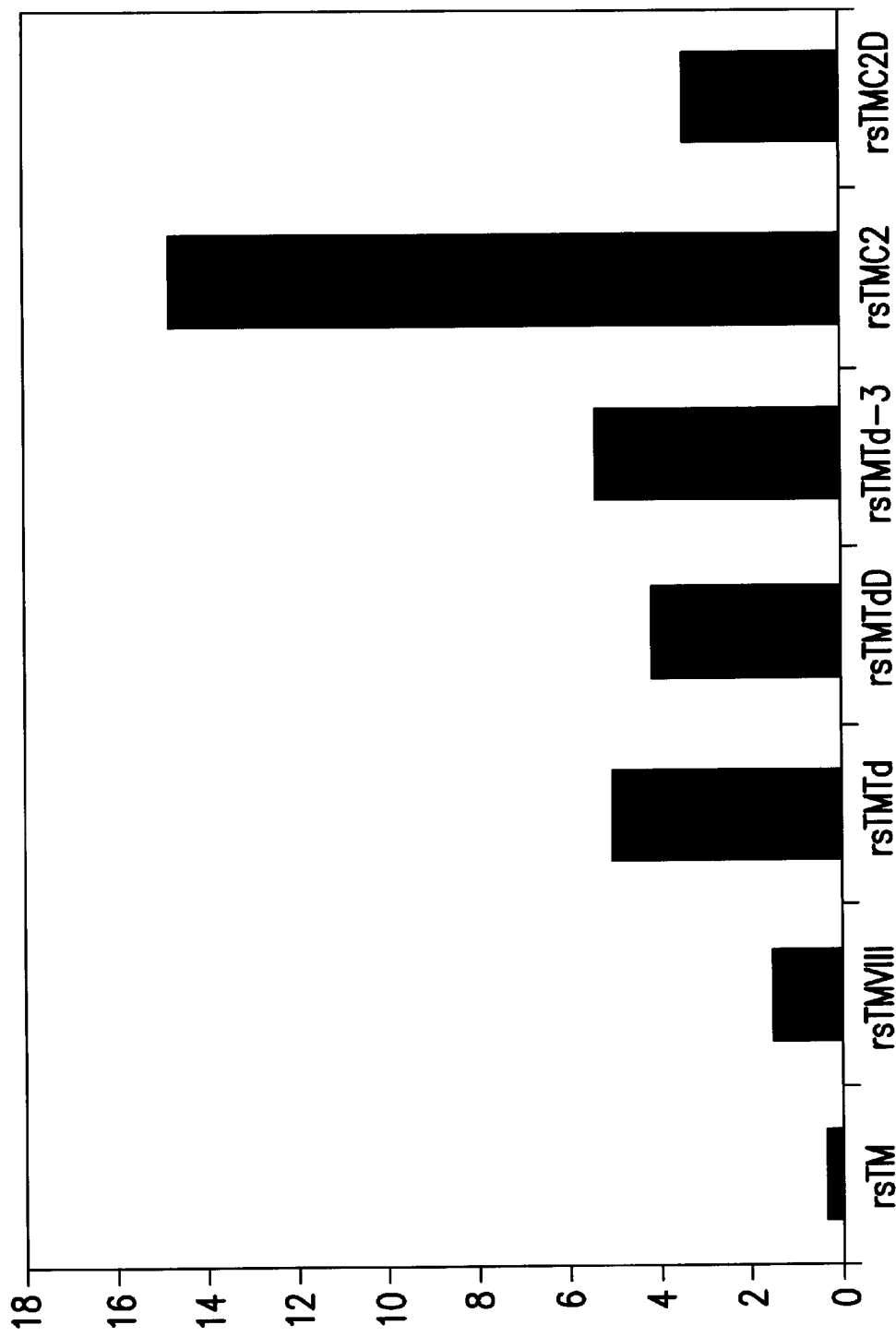
FIG. 11 is a graph showing the result of comparison of various kinds of soluble human TM having affinity for phosphatidylserine according to the present invention with unmodified soluble human TM in terms of the ability to accelerate protein C activation, in which the vertical axis plots the relative activity of action in accelerating the protein C activation.

The above-described method was partially modified to measure the ability to accelerate the activation of protein C in the presence of a phospholipid. Stated more specifically, 75 μL of TIBS (supra) containing 6 mg/mL of the phosphatidylserine liposomes prepared in Example 6 and 2% BSA was heated at 37° C. for 1 h in order to block the nonspecific adsorption of polypeptides on the liposomes. Then, 25 μL of the supernatant of the culture of COS-1 cells in which each of the soluble human TM species having affinity for phosphatidylserine which are described in Example 5 was expressed in such an amount as to provide the same value of action in accelerating the activation of protein C as measured in the absence of phospholipids by the above-described method was added, optionally after dilution with the supernatant of the culture of COS-1 cells or, alternatively, 25 μL of the supernatant of the culture of COS-1 cells in which unmodified soluble human TM was expressed was added, optionally after dilution with the supernatant of the culture of COS-1 cells, and the mixture was subjected to reaction at 37° C. for 2 h; subsequently, 25 μL of TIBS containing 40 U/mL of bovine thrombin was added and reaction was performed at 37° C. for 10 minutes. Then, 25 μL of TIBS containing 12 U/mL of human protein C was added and reaction was performed at 37° C. for 10 minutes; in the subsequent stage, the same procedure as in the above-described method was followed to measure the ability to accelerate the activation of protein C. It should be noted that the concentration of the synthetic substrate cleaved with the activated protein C was measured on the reaction solution from which the liposomes had been removed by centrifugation at 40,000 rpm for 15 minutes. The result is shown in FIG. 11, from which it was clear that the soluble human TM species having affinity for phosphatidylserine according to the present invention were significantly enhanced in their ability to accelerate the activation of protein C in the presence of phospholipids; the degree of improvement over rsTM was by a factor of about 5 in rsTMVIII, a factor of about 10 in rsTMC2D, factors of about 16–18 in rsTMTd, rsTMTdD and rsTMTd-3 and a factor of about 50 in rsTMC2. (The magnitude of the ability to accelerate the activation of protein C in the presence of the phosphatidylserine liposomes was indicated in terms of relative values, with the magnitude of the action in accelerating the activation of protein C in the absence of liposomes being taken as unity.)

EXAMPLE 8
Specificity for a Specified Phospholipid (1)

Figure 12:
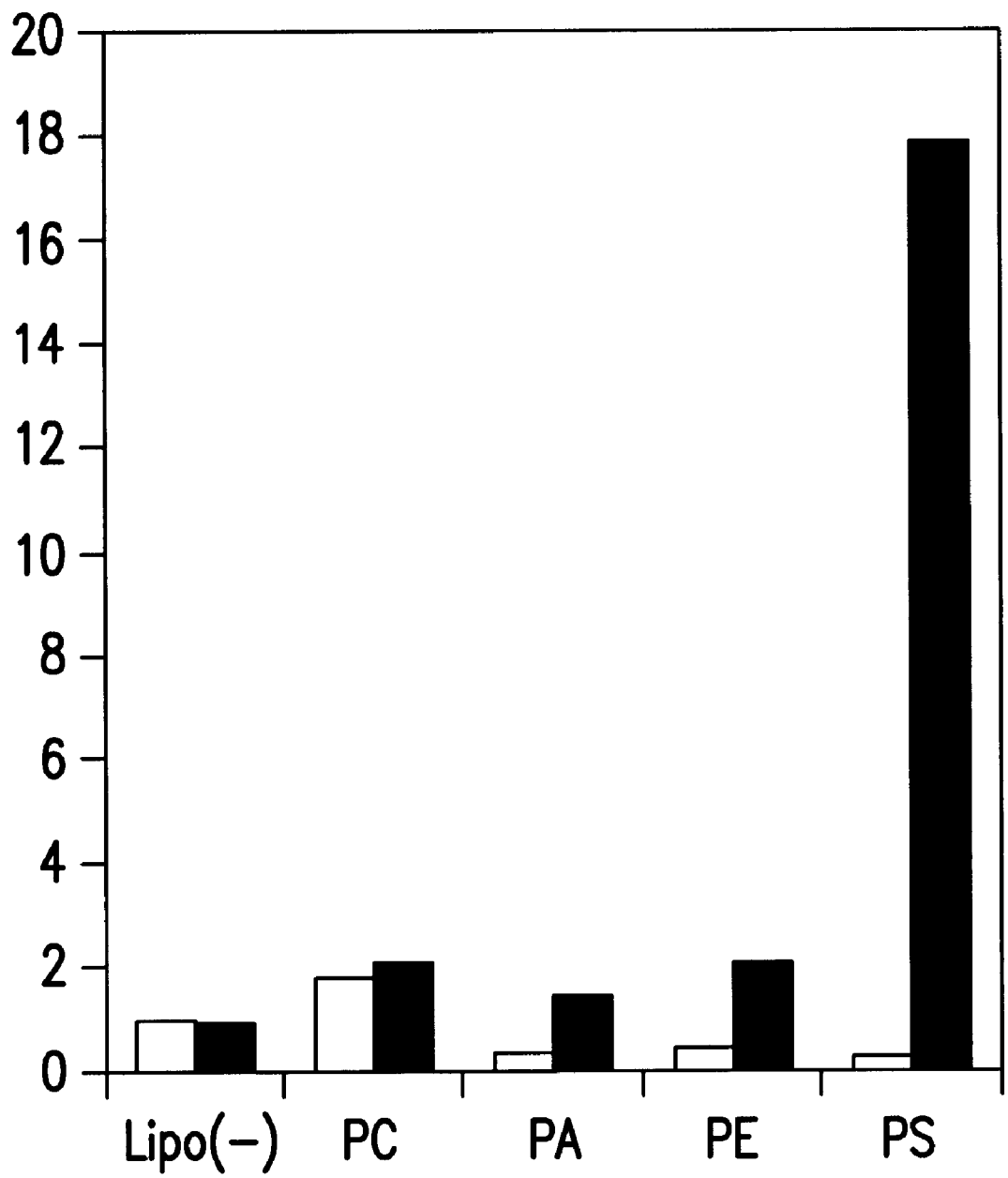
FIG. 12 is a graph showing that a soluble human TM (rsTMC2) having affinity for phosphatidylserine according to the present invention is capable of accelerating protein C activation in a phosphatidylserine specific manner, with the open columns referring to unmodified soluble human TM (rsTM) and the black columns to the soluble human TM (rsTMC2) having affinity for phosphatidylserine, in which PC, PA, PE and PS on the horizontal axis signify the components of liposomes and represent phosphatidylcholine, phosphatidic acid, phosphatidylethanolamine and phosphatidylserine, respectively, and Lipo(-) signifies the absence of liposomes, whereas the vertical axis plots the relative activity of the action in accelerating protein C activation.

In Example 6, liposomes were also prepared from phospholipids other than phosphatidylserine. Using those liposomes, a soluble human TM species having affinity for phosphatidylserine (rsTMC2) and the unmodified soluble human TM (rsTM) were measured for their ability to accelerate the activation of protein C in accordance with the methods described in Example 7. The result is shown in FIG. 12, from which it was clear that the ability of accelerate the activation of protein C of the soluble human TM of the present invention having affinity for phosphatidylserine was selective in that it increased markedly only in the presence of the phosphatidylserine liposomes. (The magnitude of the action in accelerating the activation of protein C in the presence of different kinds of liposomes was indicated in terms of relative values, with the magnitude of the action in accelerating the activation of protein C in the absence of liposomes being taken as unity.)

EXAMPLE 9
Evaluation of the Ability to Bind to Phospholipids

Figure 13:
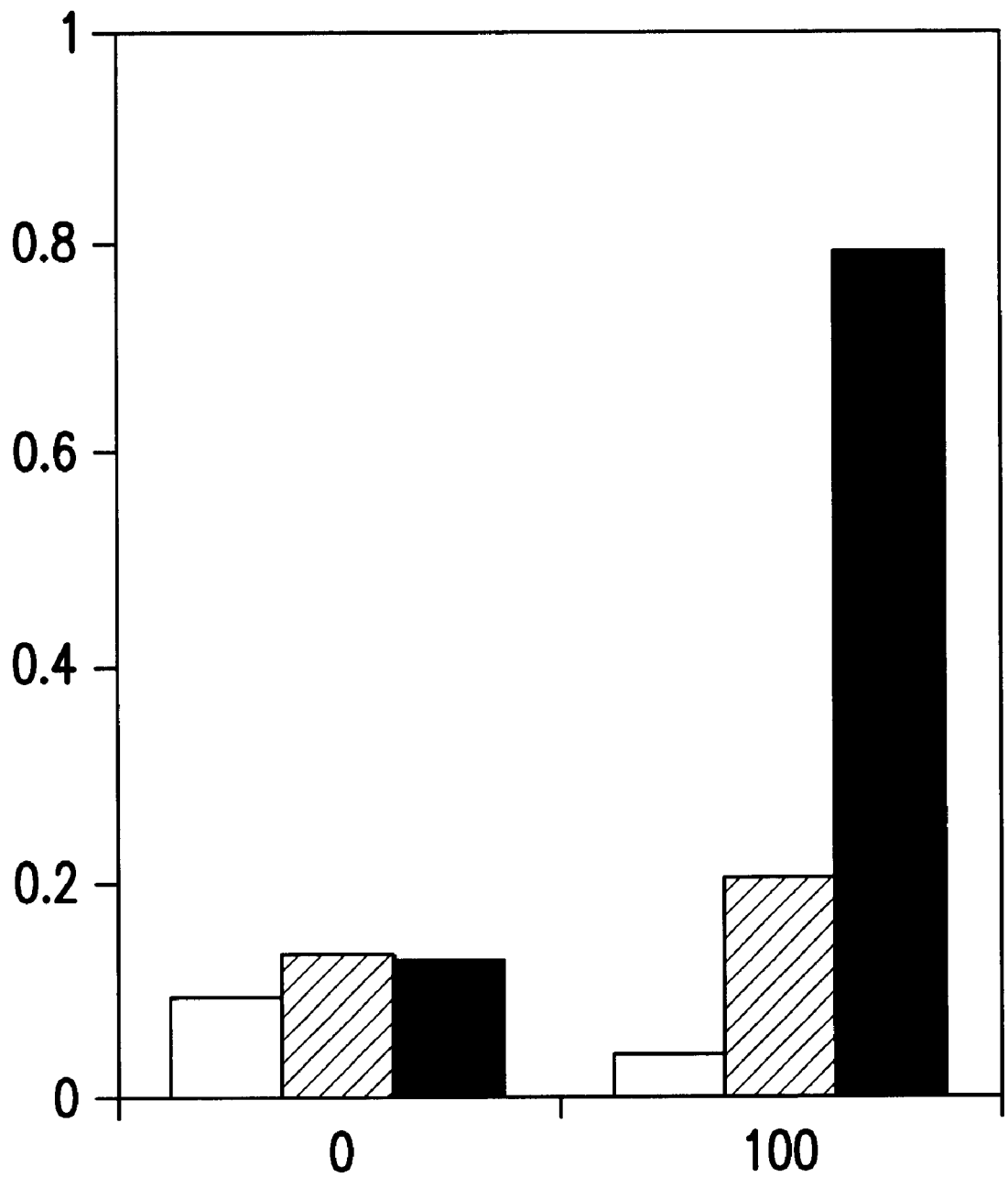
FIG. 13 is a graph showing that soluble human TMs having affinity for phosphatidylserine according to the present invention bind to phospholipid in a phosphatidylserine specific manner, in which the open columns refer to unmodified soluble human TM (rsTM) whereas the hatched and black columns refer to the soluble human TMs having affinity for phosphatidylserine (which are respectively rsTMTd and rsTMC2), and the horizontal axis of the graph plots the content of phosphatidylserine in liposomes composed of phosphatidylcholine and phosphatidylserine whereas the vertical axis plots the amount of binding (absorbance).

A 96-well microtiter plate (Immulon I, product of Dynatec) was treated with 100 μL of ethanol having either phosphatidylserine or phosphatidylcholine dissolved therein; the plate was air-dried to make a solid phase of each phospholipid in an amount of 1 μg per well. Then, there was added 200 μL of 10 mM Tris-HCl buffer (pH 7.4) containing 1% BSA and 0.15 M NaCl, and blocking was performed at 37° C. for 2 h. After removing the blocking solution, 100 μL of the supernatant of the culture of COS-1 cells that contained genetically expressed rsTMC2 (see Example 5) to which 20% aqueous BSA was added to provide a final BSA concentration of 1% were added, or 100 μL of a similarly prepared supernatant of the culture of COS-1 cells that contained either genetically expressed rsTMTd or rsTM and 1% BSA, and the mixture was subjected to reaction at 4° C. for 16 h. After the end of the reaction, each of the phospholipid-bound soluble human TM species having affinity for phosphatidylserine and the unmodified soluble human TM were quantitated by enzyme immunoassay (EIA) in accordance with the common method described in a literature ("Koso Meneki Sokuteiho (3rd Ed.)", authored by Ishikawa E. et al., published by Igaku Shoin, 1987). Stated more specifically, using an anti-human TM monoclonal antibody (24FM, product of Celbio) as a primary antibody and a horseradish peroxidase labelled anti-mouse IgG antibody (P0260, product of Daco) as a secondary antibody, and with tetramethylbenzidine as a color forming substrate, absorbance were measured with a spectrophotometer (Model NJ-2100, product of Intermed) at a wavelength of 450 nm. The result is shown in FIG. 13, from which it is clear that the soluble human TM species having affinity for phosphatidylserine have ability to bind only to phosphatidylserine and that the intensity of the binding is correlated with the magnitude of the ability to accelerate the activation of protein C in the presence of phospholipids (see FIG. 11).

EXAMPLE 10
Cloning of UTI cDNA and Preparing UTI Expressing Plasmids

By referring to a known DNA sequence coding for human α-microglobulin [Kaumeyer, J. F. et al., Nucl. Acids Res., Vol. 14, 7839 (1986)], a DNA primer (S7, see FIG. 1) that corresponded to a portion of the DNA sequence of a human α-microglobulin signal peptide and which contained a suitable restriction enzyme recognition site at 5' end was synthesized with a chemical synthesizer (supra). In addition, by referring to a known DNA sequence of human UTI (Kaumeyer, J. F. et al., Nucl. Acids Res., Vol. 14, 7839 (1986)), a DNA primer (A6, see FIG. 2) that corresponded to a portion of the DNA sequence of human UTI and which contained a suitable restriction enzyme recognition site at 5' end was synthesized with the chemical synthesizer (supra).

It should be noted that A6 contained a DNA sequence corresponding to a termination codon. The synthesized DNA primers were purified on an OPC column (supra).

Then, using a commercially available human liver derived cDNA (product of CLONTECH) as template DNA, PCR was performed using chemically synthesized DNA primers S7 and A6 in accordance with the reaction solution's recipe shown in Table 1 (supra), thereby amplifying a human α-microglobulin cDNA and a human UTI cDNA flanking on its 3' side. DNA amplification was performed with a thermal cycler (supra) by repeating 40 reaction cycles, each consisting of 94° C.×45 sec, 60° C.×45 sec and 72° C.×2 min and 30 sec; after the end of the reaction, a portion of the reaction solution was sampled and subjected to agarose gel electrophoresis, which verified the amplification of the desired size of DNA.

Figure 15:
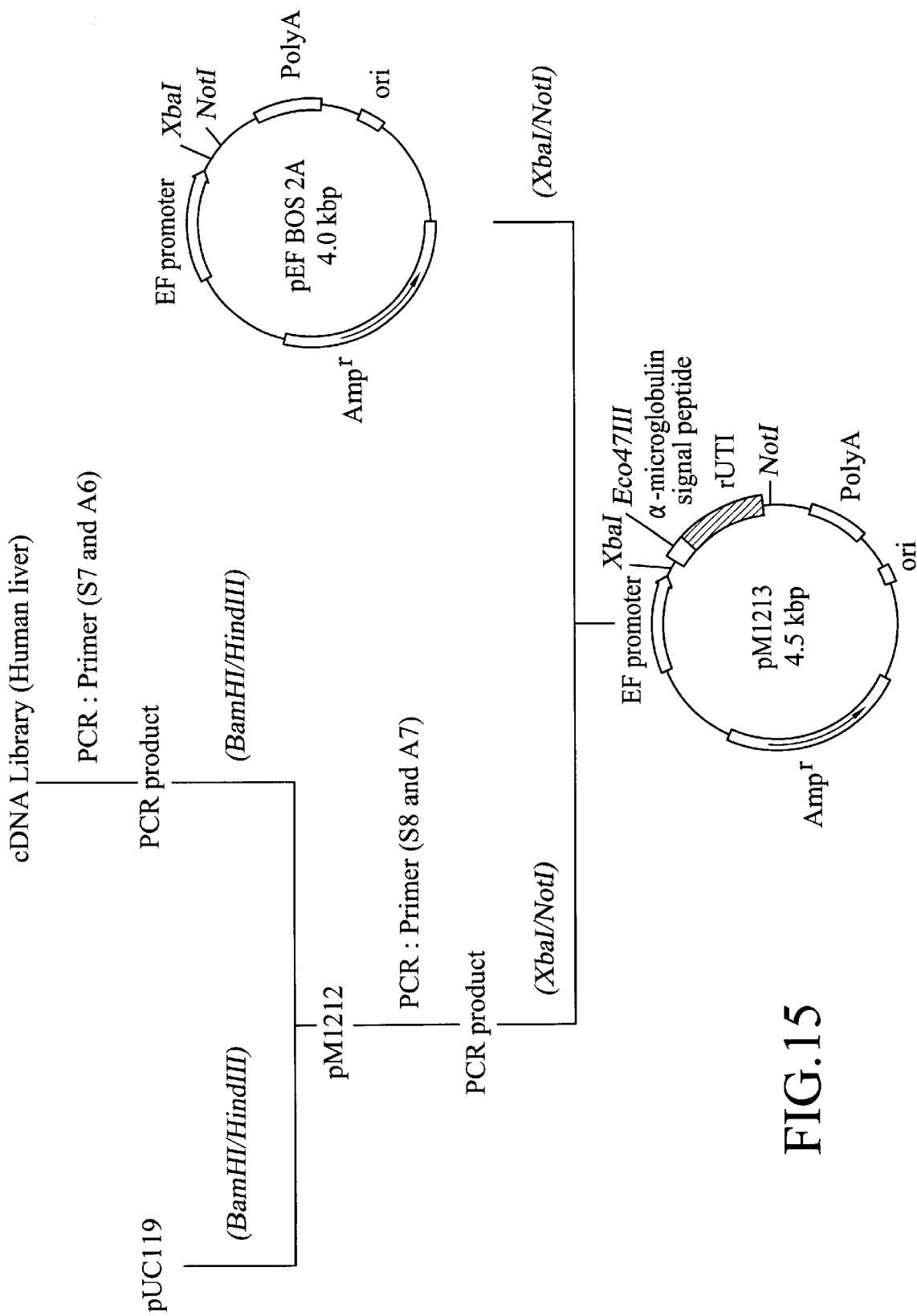
FIG. 15 is a diagram showing the process of constructing an expression vector pM1213 according to the present invention.

The amplified DNA was purified and recovered from the reaction solution by a phenol/chloroform treatment and ethanol precipitation; the recovered DNA was digested with a restriction enzyme pair BamHI/HindIII and thereafter subcloned into a cloning vector pUC119 in the usual manner to yield pM1212 (the process of its construction is shown in FIG. 15). In addition, the base sequences of the cDNA portions were determined with a DNA sequencer (supra) to verify that they consisted of a human α-microglobulin cDNA and a human UTI cDNA flanking on its 3' side.

Then, a DNA primer (S8, see FIG. 1) that contained a portion of a known DNA sequence of human α-microglobulin signal peptide and a portion of the known DNA sequence of human UTI and which also contained a suitable restriction enzyme recognition site at 5' end, and a DNA primer (A7, see FIG. 2) that contained a portion of the known DNA sequence of human UTI and which also contained a suitable restriction enzyme recognition site at 5' end were synthesized with the chemical synthesizer (supra). It should be noted that A7 contained a DNA sequence corresponding to a termination codon. The synthesized DNA primers were purified on the OPC column (supra).

Subsequently, using the thus prepared DNA primers, PCR was performed using the aforementioned pM1212 as template DNA in accordance with the reaction solution's recipe shown in Table 1 (supra), thereby amplifying human UTI cDNA having a human α-microglobulin signal peptide. DNA amplification was performed with the thermal cycler (supra) by repeating 25 reaction cycles, each consisting of 94° C.×30 sec., 55° C.×30 sec, and 72° C.×1 min. After the end of the reaction, a portion of the reaction solution was sampled and subjected to agarose gel electrophoresis, which verified the amplification of the intended size of DNA.

The amplified DNA was purified and recovered from the reaction solution by a phenol/chloroform treatment and ethanol precipitation; the recovered DNA was digested with a restriction enzyme pair XbaI/NotI and subjected to agarose gel electrophoresis, thereby separating and recovering a DNA fragment ca. 0.5 kbp in length in the usual manner. The fragment was inserted between cloning sites, XbaI and NotI, in pEF-BOS2A which was an improved expression vector of a known mammalian cell expression vector pEF-BOS (S. Mizushima et al., Nucleic Acids Res., Vol. 18, 5322 (1990)) and a human UTI expressing vector pM1213 was constructed (the process of its construction is shown in FIG. 15). The improved expression vector pEF-BOS2A has the promoter region of a human polypeptide chain extension factor 1α and the poly(A)⁺ signal sequence of SV40. The plasmid pM1213 contains DNA having the DNA sequence of SEQ ID NO:28 and using this, one can produce unmodified UTI of SEQ ID NO:24 (which is hereinafter designated as rUTI).

EXAMPLE 11
Preparing Plasmid Expressing UTI Having Affinity for Phosphatidylserine Two species of single-stranded DNA (F13 and F14; see FIG. 5) were synthesized with a chemical synthesizer (supra) and F13 and F14 were annealed in the usual manner to yield DNA fragment G ca. 70 bp in length which had an EcoRI cleaved surface at 5' end and a HindIII cleaved surface at 3' end. Then, fragment G was subcloned into a cloning vector pUC119 between cloning sites EcoRI and HindIII, thereby yielding pUC119-Multi. Subsequently, the pUC119-Multi was digested with restriction enzymes Eco47III and NotI and subjected to agarose gel electrophoresis, thereby yielding a DNA fragment of ca. 3.2 kbp. In a separate step, pM1213 prepared in Example 10 was digested with restriction enzymes Eco47III and NotI and also subjected to agarose gel electrophoresis, thereby yielding a DNA fragment of ca. 0.5 kbp. The two fragments of ca. 3.2 kbp and 0.5 kbp in length were ligated in the usual manner to yield pUC119-UTI-sub1.

In a separate step, by referring to a known DNA sequence of human UTI (supra) and a known DNA sequence of human factor VIII (supra), a DNA primer (S9; see FIG. 1) corresponding to a portion of the DNA sequence of a human UTI and a portion of the DNA sequence of a human factor VIII, and a DNA primer (A8; see FIG. 2) that corresponded to a portion of the DNA sequence of the human factor VIII and which also contained a suitable restriction enzyme recognition site at 5' end were synthesized with the chemical synthesizer (supra). It should be noted that A8 contained a DNA sequence corresponding to a termination codon. The synthesized DNA primers were purified on an OPC column (supra).

Figure 16:
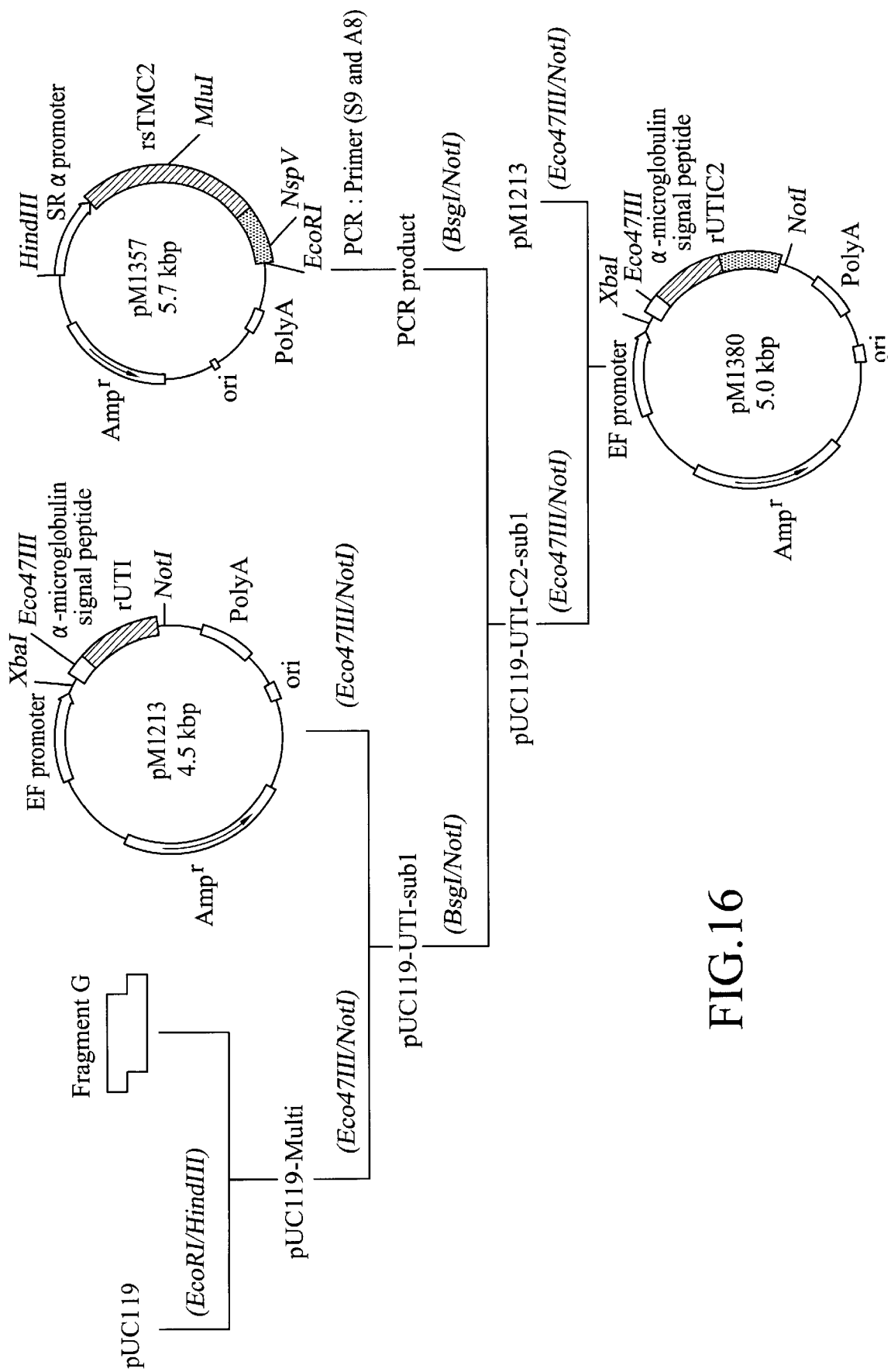
FIG. 16 is a diagram showing the process of constructing an expression vector pM1380 according to the present invention.

Then, using those DNA primers, PCR was performed using the pM1357 synthesized in Example 3(2) as template DNA and in accordance with the reaction solution's recipe shown in Table 1 (supra), thereby amplifying a DNA fragment of ca. 0.6 kbp that contained the C2 region of human factor VIII and which had a region corresponding to a portion of the DNA sequence of the human UTI at 5' end. DNA amplification was performed using thermal cycler (supra) by repeating 30 reaction cycles, each consisting of 94° C.×1 min, 55° C.×2 min, and 72° C.×3 min; after the end of the reaction, a portion of the reaction solution was sampled and subjected to agarose gel electrophoresis, which verified the amplification of the intended size of DNA. The amplified DNA was purified and recovered from the reaction solution by a phenol/chloroform treatment and ethanol precipitation, and then, the recovered DNA was digested with restriction enzymes BsgI and NotI. In a separate step, the aforementioned pUC119-UTI-sub1 was digested with restriction enzymes BsgI and NotI and subjected to agarose gel electrophoresis, thereby separating and recovering a DNA fragment of ca. 3.1 kbp. This fragment and the previously digested DNA were ligated in the usual manner to yield pUC119-UTI-C2-sub1. Subsequently, the pUC119-UTI-C2-sub1 was digested with restriction enzymes Eco47III and NotI and subjected to agarose gel electrophoresis, thereby separating and recovering a DNA fragment of ca. 1.0 kbp. In a separate step, the pM1213 prepared in Example 10 was digested with restriction enzymes Eco47III and NotI, thereby separating and recovering a DNA fragment of ca. 4.0 kbp. The two fragments ca. 1.0 kbp and ca. 4.0 kbp in length were ligated in the usual manner to yield pM1380 (the process of its construction is shown in FIG. 16). This plasmid contained DNA consisting of a nucleotide sequence in which the DNA sequence of SEQ ID NO:20 was linked to the 3' side of the nucleotide sequence of SEQ ID NO:28; using the plasmid, one can produce human UTI having affinity for phosphatidylserine which is a peptide consisting of an amino acid sequence in which the amino acid sequence of SEQ ID NO:9 is linked to the C terminus of the amino acid sequence of SEQ ID NO:24 (said human UTI is hereinafter referred to as rUTIC2).

EXAMPLE 12
Expression and Purification of rUTI and rUTIC2

The plasmids pM1380 and pM1213 prepared in Examples 11 and 10 were each transfected into COS-1 cells (supra) by a DEAE dextran method (supra), thereby expressing human UTI having affinity for phosphatidylserine and unmodified human UTI. Stated more specifically, ca. $3 \times 10^5$ cells/9 $cm^2$ were inoculated in each plastic tissue culture plate and cultivated at 37° C. for one day in 2 mL of a Dulbecco modified Eagle's medium (supra) containing 10% fetal bovine serum. After washing three times with 2 mL of DMEM, culture medium was replaced by 0.7 mL of DMEM containing 1 µg of each of the plasmids, 50 mM Tris-HCl (pH 7.4), 0.2 mg/mL of DEAE dextran and 150 µM chloroquine. After cultivation at 37° C. for 4 h, the culture solution was removed by suction; after washing once with 2 mL of DMEM and once with DMEM containing 10% fetal bovine serum, 2 mL of DMEM containing 10% fetal bovine serum was added and cultivation was continued at 37° C. for 24 h. Thereafter, the culture medium was replaced by DMEM containing 0.1% BSA and cultivation was continued at 37° C. for an additional 72 h, and the supernatant of the culture was collected. It was found that collected supernatant of the culture contained human UTI having affinity for phosphatidylserine (rUTIC2) and unmodified human UTI (rUTI) in amounts of 1–5 µg/mL.

The collected culture solution was desalted and concentrated using an ultrafiltration membrane having a molecular weight cutoff value of $10^4$. The concentrate was passed through an anti-UTI antibody-Sepharose column preliminarily equilibrated with 10 mM phosphate buffer (pH 7.5), whereby active fractions were adsorbed on the column. Then, after washing with 10 mM phosphate buffer (pH 7.5) containing 0.5 M NaCl, the active fractions were eluted with 0.1 M citric acid (pH 2.0) and 0.1 M citric acid containing 3 M potassium thiocyanate. The eluted active fractions were dialyzed against 10 mM phosphate buffer (pH 7.5) to obtain pure forms of human UTI having affinity for phosphatidylserine (rUTIC2)and unmodified human UTI (rUTI).

EXAMPLE 13
Preparing Plasmid Expressing the Second Region of UTI

Figure 17:
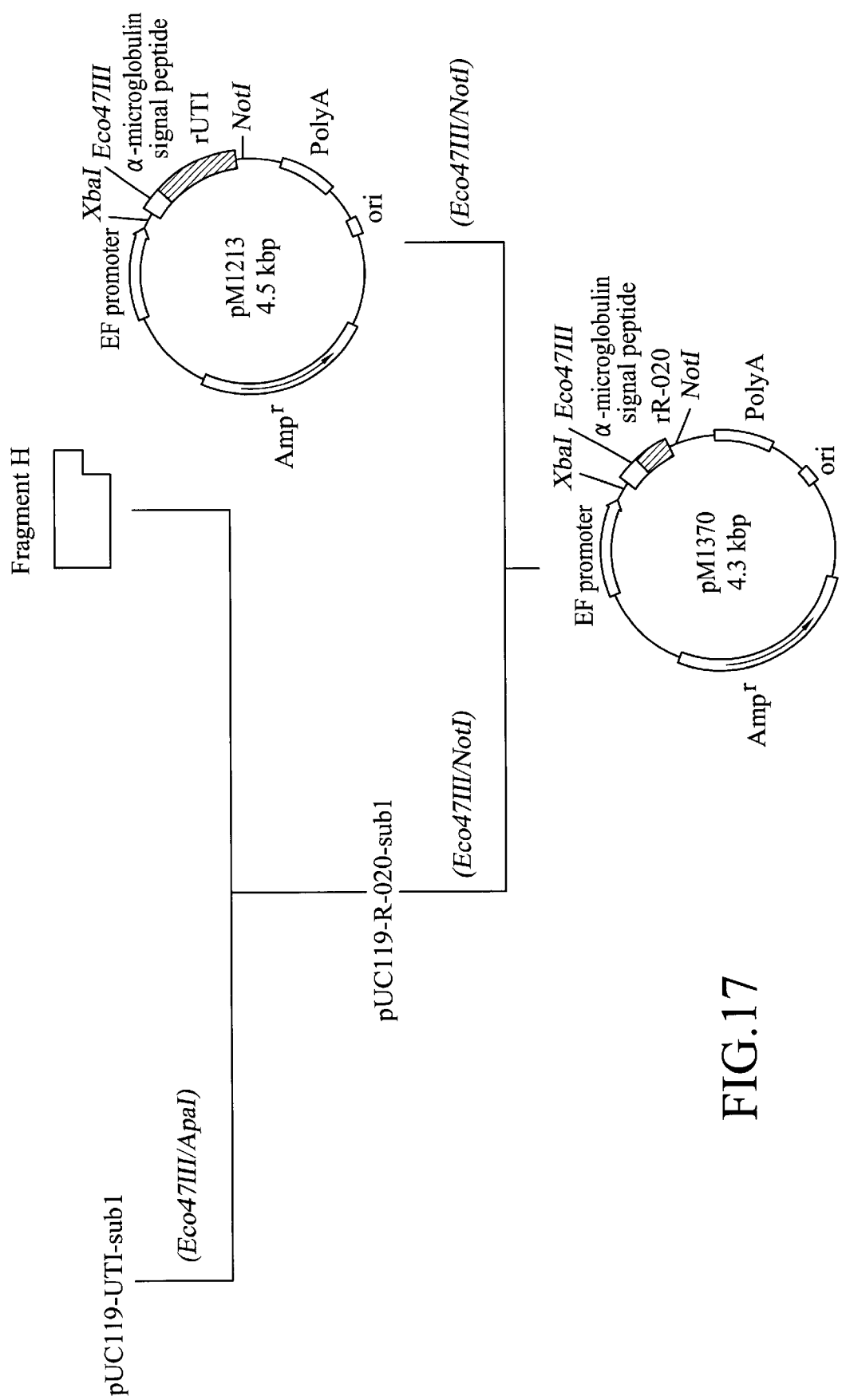
FIG. 17 is a diagram showing the process of constructing an expression vector pM1370 according to the present invention.

Two species of single-stranded DNA (F15 and F16; see FIG. 5) were synthesized with a chemical synthesizer (supra) and both were annealed in the usual manner to yield DNA fragment H ca. 70 bp in length which had an Eco47III cleaved surface at 5' end and an ApaI cleaved surface at 3' end. Then, the pUC119-UTI-sub1 prepared in Example 11 was digested with restriction enzymes Eco47III and ApaI and subjected to agarose gel electrophoresis, thereby yielding a DNA fragment of ca. 3.4 kbp. This fragment was ligated with fragment H in the usual manner to yield pUC119-R-020-sub1. Subsequently, the pUC119-R-020-sub1 was digested with restriction enzymes Eco47III and NotI and subjected to agarose gel electrophoresis, thereby separating and recovering a DNA fragment of ca. 0.2 kbp. In a separate step, the pM1213 prepared in Example 10 was digested with restriction enzymes Eco47III and NotI and subjected to agarose gel electrophoresis, thereby separating and recovering a DNA fragment of ca. 4.0 kbp. This fragment and the previously obtained fragment of ca. 0.2 kbp were ligated in the usual manner to yield pM1370 (the process of its construction is shown in FIG. 17). The plasmid pM1370 contains DNA having the sequence of SEQ ID NO:27 and using this, one can produce a polypeptide in which 11 amino acids (Ala-Val-Leu-Pro-Gln-Glu-Glu-Glu-Gly-Asp-Gly (SEQ ID NO:67)) is attached to the N terminus of the second region of unmodified human UTI represented by SEQ ID NO:23 (said human UTI is hereinafter referred to as Rr-020).

Figure 18:
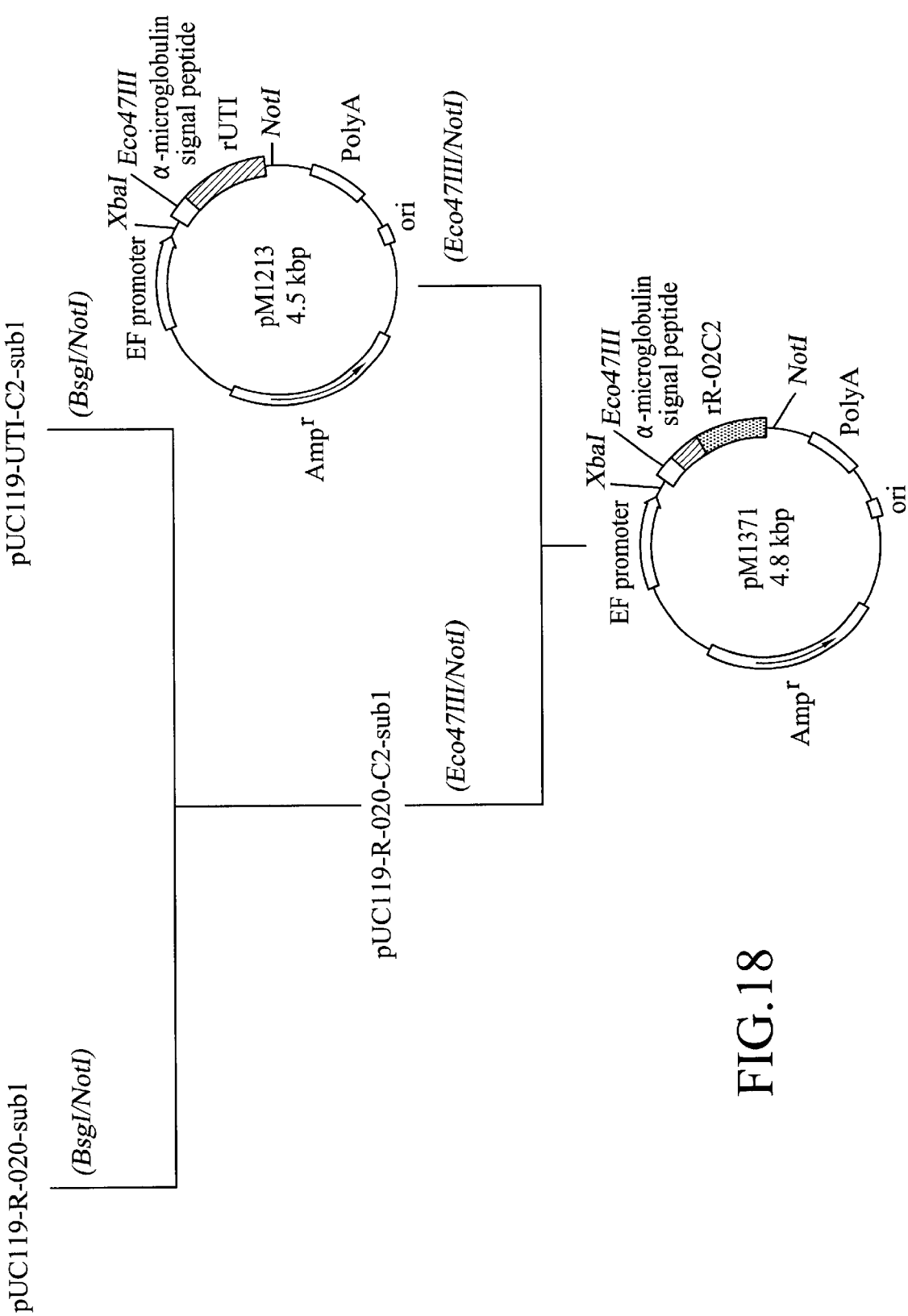
FIG. 18 is a diagram showing the process of constructing an expression vector pM1371 according to the present invention.

EXAMPLE 14
Preparing Plasmid Expressing the Second Region of UTI Having Affinity for Phosphatidylserine The pUC119-R-020-sub1 prepared in Example 13 was digested with restriction enzymes BsgI and NotI and subjected to agarose gel electrophoresis, thereby yielding a DNA fragment of ca. 3.3 kbp. In a separate step, the pUC119-UTI-C2-sub1 prepared in Example 11 was digested with restriction enzymes BsgI and NotI and subjected to agarose gel electrophoresis, thereby yielding a DNA fragment of ca. 0.5 kbp. The two fragments ca. 3.3 kbp and ca. 0.5 kbp in length were ligated in the usual manner to yield pUC119-R-020-C2-sub1. Subsequently, the pUC119-R-020-C2-sub1 was digested with restriction enzymes Eco47III and NotI and subjected to agarose gel electrophoresis, thereby separating and recovering a DNA fragment of ca. 0.8 kbp. In a separate step, the pM1213 prepared in Example 10 was digested with restriction enzymes Eco47III and NotI and also subjected to agarose gel electrophoresis, thereby separating and recovering a DNA fragment of ca. 4.0 kbp. The two fragments ca. 0.8 kbp and ca. 4.0 kbp in length were ligated in the usual manner to yield pM1317 (the process of its construction is shown in FIG. 18). This plasmid contains DNA made up of a nucleotide sequence in which the nucleotide sequence of SEQ ID NO:20 is linked to the 3' side of the nucleotide sequence of SEQ ID NO:27; using this, one can produce the second region of human UTI having affinity for phosphatidylserine which is a peptide consisting of an amino acid sequence in which the sequence of 11 amino acids (Ala-Val-Leu-Pro-Gln-Glu-Glu-Glu-Gly-Asp-Gly (SEQ ID NO:67)) is linked to the N terminus of the amino acid sequence of SEQ ID NO:23 whereas the amino acid sequence of SEQ ID NO:9 is linked to the C terminus (said second region of human UTI is hereinafter designated rR-020C2).

EXAMPLE 15
Expression and Purification of rR-020 and rR-020C2

The plasmids pM1371 and pM1370 prepared in Examples 14 and 13 were each transfected into COS-1 cells (supra) by a DEAE dextran method (supra), thereby expressing the second region of human UTI having affinity for phosphatidylserine and the second region of unmodified human UTI. Stated more specifically, ca. $3 \times 10^5$ cells/9 $cm^2$ were inoculated in each plastic tissue culture plate and cultivated at 37° C. for one day in 2 mL of a Dulbecco modified Eagle's medium (supra) containing 10% fetal bovine serum. After washing three times with 2 mL of DMEM, culture medium was replaced by 0.7 mL of DMEM containing 1 µg of each of the plasmids, 50 mM Tris-HCl (pH 7.4), 0.2 mg/mL of DEAE dextran and 150 µM chloroquine. After cultivation at 37° C. for 4 h, the culture solution was removed by suction; after washing once with 2 mL of DMEM and once with DMEM containing 10% fetal bovine serum, 2 mL of DMEM containing 10% fetal bovine serum was added and cultivation was continued at 37° C. for 24 h. Thereafter, the culture medium was replaced by DMEM containing 0.1% BSA and cultivation was continued at 37° C. for an additional 72 h, and the supernatant of the culture was collected. It was found that the collected culture medium contained the secondary region of human UTI having affinity for phosphatidylserine (rR-020C2) and the second region of unmodified human UTI (rR-020) in amounts of 1–5 µg/mL.

The collected culture solution was desalted and concentrated using an ultrafiltration membrane having a molecular weight cutoff value of $3 \times 10^3$. The concentrate was passed through an anti-UTI antibody-Sepharose column preliminarily equilibrated with 10 mM phosphate buffer (pH 7.5), whereby active fractions were adsorbed on the column. Then, after washing with 10 mM phosphate buffer (pH 7.5) containing 0.5 M NaCl, the active fractions were eluted with 0.1 M citric acid (pH 2.0) and 0.1 M citric acid containing 3 M potassium thiocyanate. The eluted active fractions were dialyzed against 10 mM phosphate buffer (pH 7.5) to obtain pure forms of the second region of human UTI having affinity for phosphatidylserine (rR-020C2) and the second region of unmodified human UTI (rR-020).

EXAMPLE 16
Measuring Trypsin Inhibitory Activity

Each of the human UTI (rUTI), the second region of human UTI (rR-020), the human UTI having affinity for phosphatidylserine (rUTIC2) and the second region of human UTI having affinity for phosphatidylserine (rR-020C2), which are described in Examples 12 and 15, were expressed by COS-1 cells. To 100 µL of the supernatant of each culture medium, bovine trypsin (200 BAEEU/mL; product of Sigma) diluted with 0.2 M Tris-HCl buffer (pH 7.8) containing 0.1% BSA (said buffer is hereinafter designed as Buffer A) was added in an amount of 100 µL and reaction was performed at 25° C. for 10 minutes; thereafter, 100 µL of a substrate solution containing 2 mg/mL of a synthetic substrate L-BAPA (product of Peptide Research Laboratory) dissolved in distilled water was added and reaction was performed at 25° C. for 12 minutes. Subsequently, 100 µL of 50% aqueous acetic acid was added to terminate all reactions and the concentration of the synthetic substrate cleaved with the remaining trypsin was measured with a spectrophotometer (supra) at a wavelength of 405 nm. In the experiment, the second region of human UTI that was made up of the amino acid sequence of SEQ ID NO:23 and which had been expressed in *E. coli* and subsequently purified was used as a control. (see Japanese Patent Public Disclosure KOKAI 84083/1993)

EXAMPLE 17
Measuring the Efficacy in Suppressing the Production of Active Oxygen The amount of active oxygen produced from leukocytes was measured by a cytochrome C reduction method in accordance with the method of Kato et al. (Kato K. et al., Igaku To Yakugaku, Vol. 34, 499 (1995)). Stated more specifically, leukocytes obtained from the peritoneal cavity of a rabbit were suspended in the physiological saline (pH 7.4) containing 2 mM glucose and 5 mM HEPES to give a concentration of $1 \times 10^6$ cells/mL; to 0.49 mL of the suspension, 0.5 mL of biological saline (pH 7.4) containing 132 µM cytochrome C, 2 mM glucose, 2 mM $CaCl_2$, 5 mM HEPES and the supernatant of the culture of COS-1 cells having expressed therein the human UTI having affinity for phosphatidylserine (rUTIC2) or unmodified human UTI (rUTI), both being described in Example 12, was added and reacted at 37° C. for 3 minutes. Then, 5 µL each of cytochalasin E (1 mg/mL) and concanavalin A (10 ng/mL) was added and the rate of increase in absorbance at a wavelength of 550 nm was measured with a spectrophotometer (supra).

Figure 19:
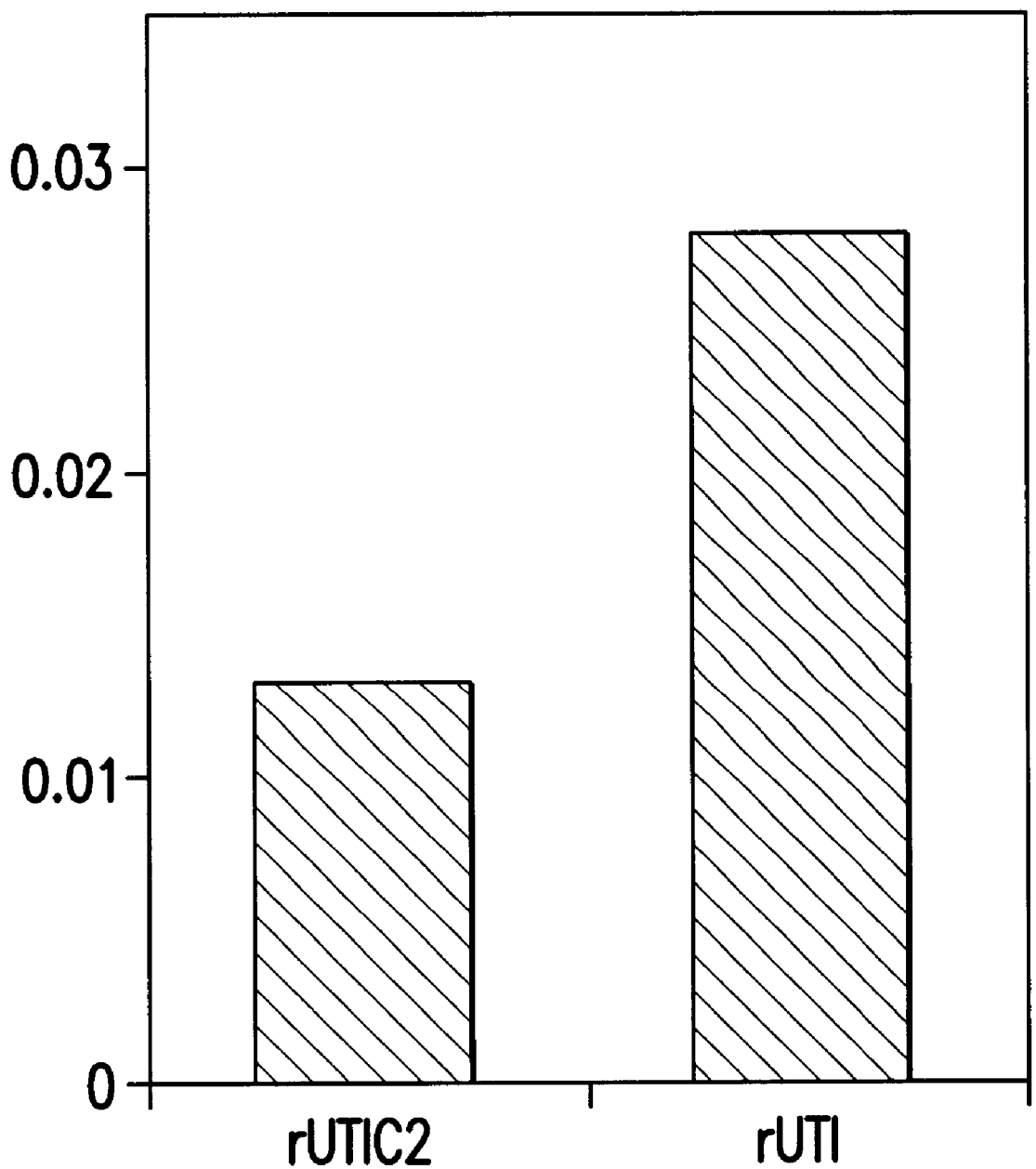
FIG. 19 is a diagram showing the result of comparison of human UTI having affinity for phosphatidylserine according to the present invention with unmodified human UTI in terms of the ability to suppress active oxygen production, in which the vertical axis plots the amount of production of active oxygen (the rate of change in absorbance per unit time).

The result is shown in FIG. 19, from which it was clear that the human UTI having affinity for phosphatidylserine (rUTIC2) according to the present invention was more effective than the unmodified human UTI (rUTI) in suppressing the production of active oxygen.

EXAMPLE 18
Measuring the Effect on Prothrombinase Inhibition

Figure 20:
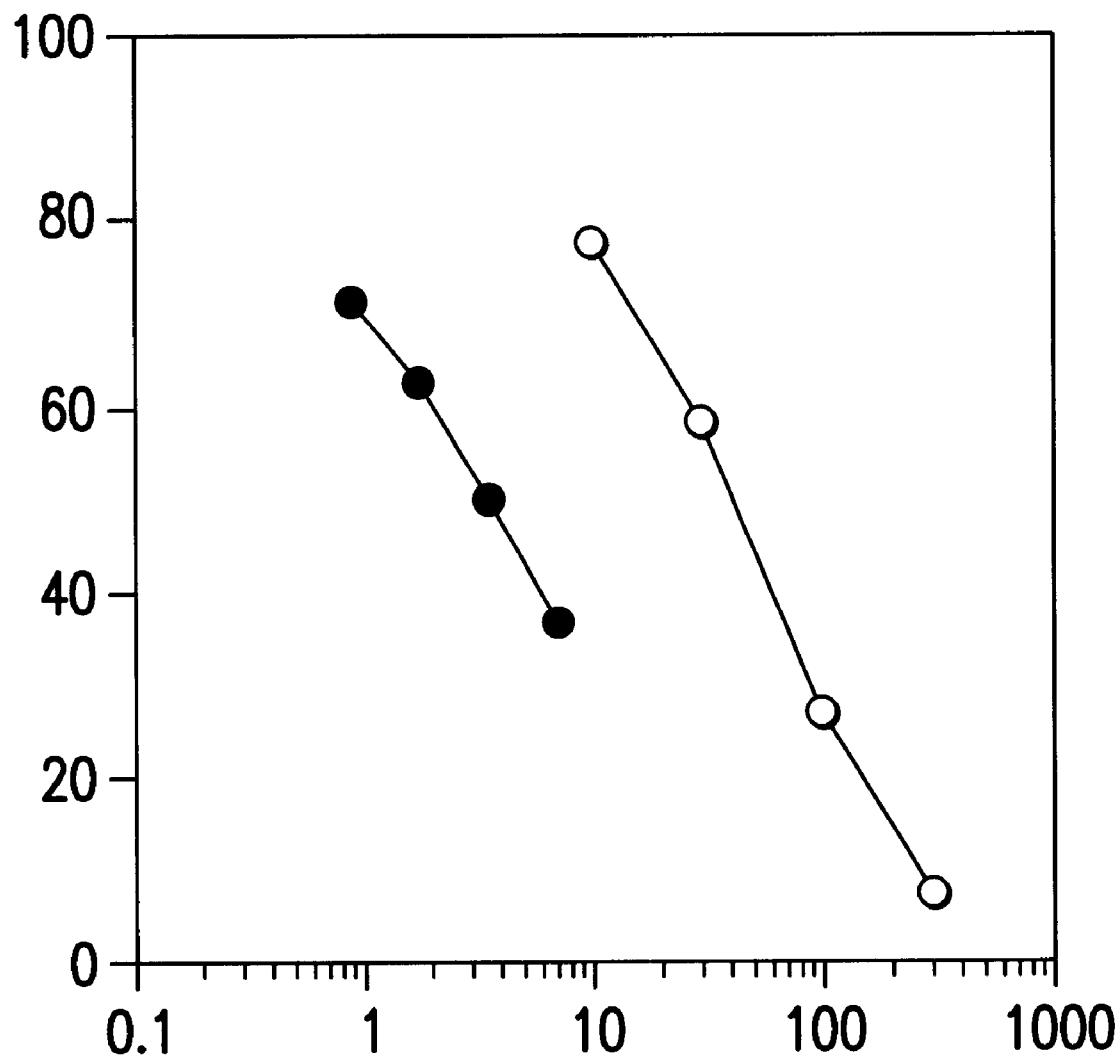
FIG. 20 is a graph showing the result of comparison of the second region of human UTI having affinity for phosphatidylserine according to the present invention (rR-020C2, indicated by ● in the graph) with the second region of human UTI expressed in E. coli (indicated by ○ in the graph) in terms of the ability to inhibit the activity of prothrombinase, in which the horizontal axis plots the concentrations of rR-020C2 and the second region of E. coli expressed human UTI in terms of trypsin inhibiting activity whereas the vertical axis plots the percent residual activity of prothrombinase.

Measurement of prothrombinase activity was measured by a procedure adapted from the method of Nesheim, M. E. (The Journal of Biological Chemistry, Vol. 254, 10952 (1979)). State more specifically, 50 mM Tris-HCl buffer (pH 7.4) containing 6 µM factor Xa (product of American Diagnostica), 6 µM factor Va (product of Haematological Technology), 0.15 M NaCl, 2 mM $CaCl_2$ and 0.1% BSA was provided (said buffer is hereinafter designated as Buffer B); to 100 µL of Buffer B, 25 µL of Buffer B containing lyposomes by the content of 36 mg/mL in terms of phospholipid that were prepared by the same procedure as in Example 6 and which consisted of 25% phosphatidylserine and 75% phosphatidylcholine (except that TIBS was replaced by BSA-free Buffer B for the preparation of the lyposomes) was added, and the mixture was heated at 37° C. for 10 minutes. Then, the supernatant of the culture of COS-1 cells having expressed therein the second region of human UTI having affinity for phosphatidylserine (rR-020C2) as described in Example 15 or the second region of human UTI (supra) that was made up of the amino acid sequence of SEQ ID NO:23 and that was expressed in *E. coli* and subsequently purified was added optionally after dilution with the supernatant of the culture of COS-1 cells in an amount of 125 µL, and the resulting mixture was heated at 37° C. for 10 minutes. Then, 50 µL of Buffer B containing 60 µM of prothrombin (product of Enzyme Research Laboratory) was added and reaction was performed at 37° C. for 30 minutes; thereafter, 300 µL of buffer B containing 10 mM of EDTA was added to terminate the thrombin producing reaction. Subsequently, 100 µL of the solution obtained by the aforementioned thrombin producing reaction which was no longer in progress was heated at 37° C. for 10 minutes; thereafter, 100 µL of 50 mL Tris-HCl buffer (pH 7.4) containing 1.5 mM synthetic substrate S-2238 (product of Daiichi Pure Chemicals Co., Ltd.), 0.15 M NaCl, 10 mM EDTA and 0.1% BSA was added and reaction was performed at 37° C. for 10 minutes; thereafter, 100 µL of 50% aqueous acetic acid was added to terminate all reactions and the concentration of the synthetic substrate cleaved with the produced thrombin was measured with a spectrophotometer (supra) at a wavelength of 405 nm. As it turned out, the second region of human UTI having affinity for phosphatidylserine (rR-020C2) according to the present invention was about 10 times more effective in inhibiting prothrombinase activity than the second region of human UTI made up of the amino acid Sequence of SEQ ID NO:23 (supra) that was expressed in *E. coli* and subsequently purified (see FIG. 20). It should be noted that there were no visible differences in activity between the second region of human UTI made up of the amino acid sequence of SEQ ID NO:23 that was expressed in *E. coli* and subsequently purified (supra) and the second region of the unmodified human UTI (rR-020) that was expressed in COS-1 cells.

EXAMPLE 19
Specificity for A Specified Phospholipid, (2)

Figure 21:
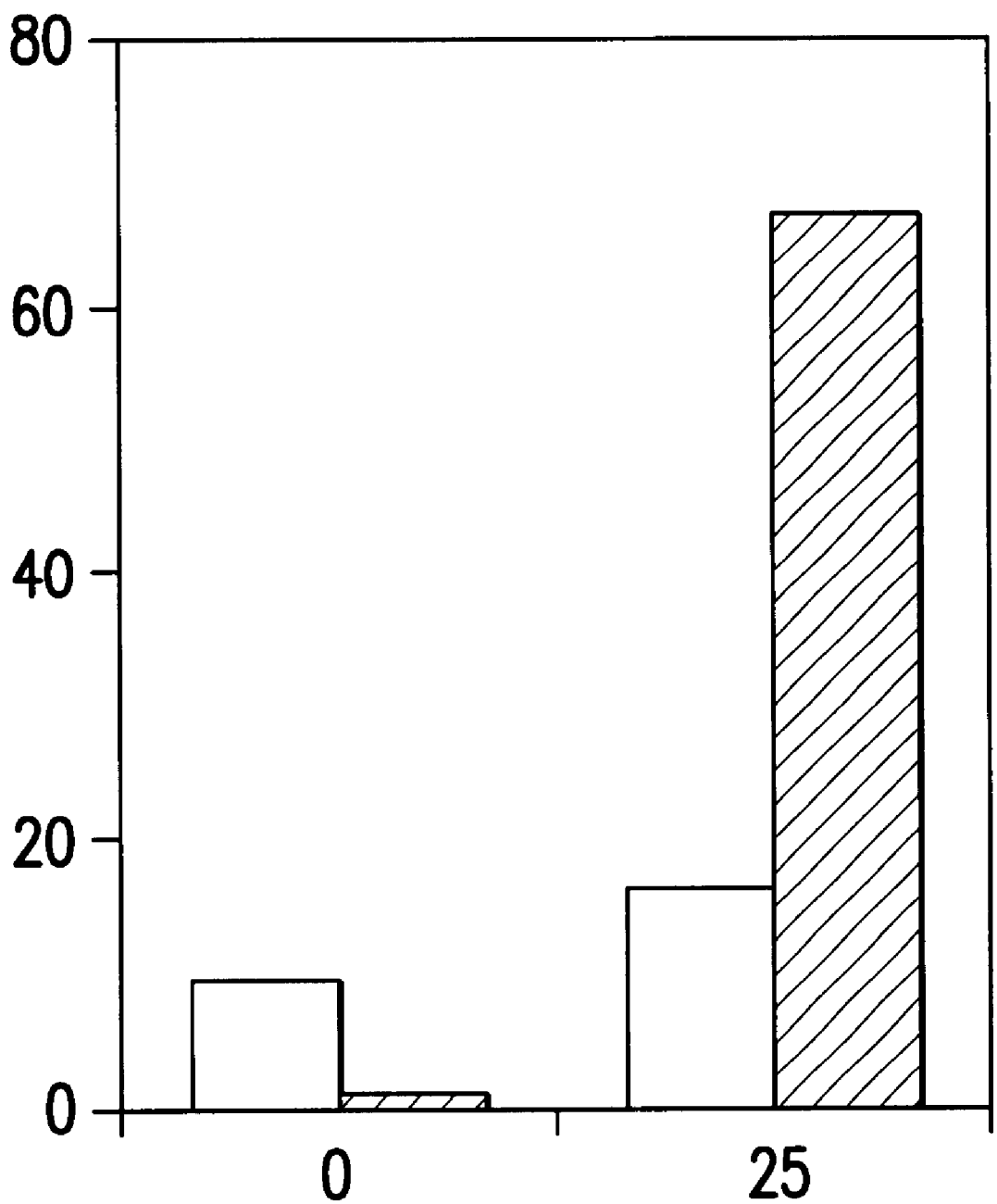
FIG. 21 is a graph showing that the second region of human UTI (rR-020C2) having affinity for phosphatidylserine according to the present invention has the ability to inhibit the activity of prothrombinase in a phosphatidylserine specific manner, with the open columns referring to rR-020 and the hatched columns R-020C2, and the horizontal axis of the graph plotting the content of phosphatidylserine in liposomes composed of phosphatidylcholine and phosphatidylserine whereas the vertical axis plots the percent inhibition of the activity of prothrombinase.

Lyposomes were prepared by the same procedure as in Example 6 and using those lyposomes, the second region of human UTI having affinity for phosphatidylserine (rR-020C2) and the second region of the unmodified human UTI (rR-020) were measured for their prothrombinase inhibitory activity in accordance with the method described in Example 18. The result is shown in FIG. 21, from which it was clear that the second region of human UTI having affinity for phosphatidylserine (rR-020C2) according to the present invention had its prothrombinase inhibitory activity accelerated in a manner specific for phosphatidylserine.

Figure 22:
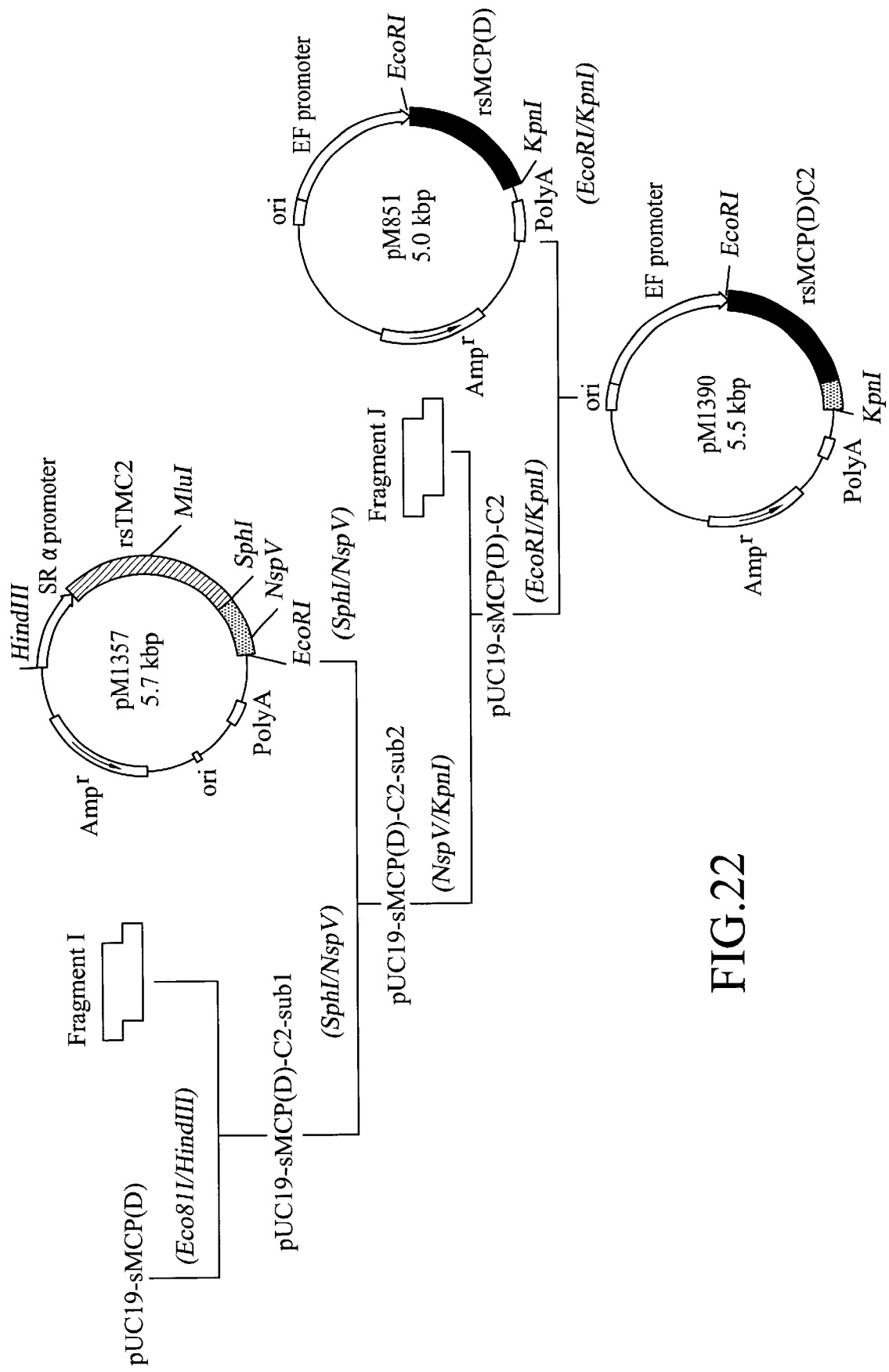
FIG. 22 is a diagram showing the process of constructing an expression vector pM1390 according to the present invention.

EXAMPLE 20
Preparation of Plasmid Expressing Soluble Human MCP Having Affinity for Phosphatidylserine Four species of single-stranded DNA (F17, F18, F19 and F20; see FIG. 5) were synthesized with a chemical synthesizer (supra) and F17 and F18 were annealed in the usual manner and so were F19 and F20, thereby yielding DNA fragment I which was ca. 60 bp in length and which had an Eco8II cleaved surface at 5' end and a HindIII cleaved surface at 3' end, as well as DNA fragment J which was ca. 90 bp in length and which had an NspV cleaved surface at 5' end and a KpnI cleaved surface at 3' end. Subsequently, the pUC19-sMCP (D) described in International Patent Publication WO/93/17122 was digested with restriction enzymes Eco81I and HindIII and subjected to agarose gel electrophoresis, thereby yielding a DNA fragment of ca. 3.6 kbp. This DNA fragment was ligated with fragment I in the usual manner to yield pUC19-sMCP(D)-C2-sub1. Subsequently, the pUC19-sMCP(D)-C2-sub11 was digested with restriction enzymes SphI and NspV and subjected to agarose gel electrophoresis, thereby separating and recovering a DNA fragment of ca. 3.7 kbp. In a separate step, the pM1357 prepared in Example 3(2) was digested with restriction enzymes SphI and NspV and subjected to agarose gel electrophoresis, thereby separating and recovering a DNA fragment of ca. 0.4 kbp. The two DNA fragments of ca. 3.7 kbp and ca. 0.4 kbp in length were ligated in the usual manner to yield pUC19-sMCP(D)-C2-sub2. Subsequently, the pUC19-sMCP(D)-C2-sub2 was digested with restriction enzymes NspV and KpnI and subjected to agarose gel electrophoresis, thereby separating and recovering a DNA fragment of ca. 4.0 kbp. This DNA fragment was ligated with fragment J in the usual manner to yield pUC19-sMCP(D)-C2. Further, the pUC19-sMCP(D)-C2 was digested with restriction enzymes EcoRI and KpnI and subjected to agarose gel electrophoresis, thereby separating and recovering a DNA fragment of ca. 1.5 kbp. In a separate step, the pM851 described in International Patent Publication WO/93/17122 was digested with restriction enzymes EcoRI and KpnI and subjected to agarose gel electrophoresis, thereby separating and recovering a DNA fragment of ca. 4.0 kbp. The two DNA fragments ca. 1.5 kbp and ca. 4.0 kbp in length were ligated in the usual manner to yield pM1390 (the process of its construction is shown in FIG. 22). This plasmid contained DNA consisting of a nucleotide sequence in which the nucleotide sequence of SEQ ID NO:20 was linked to the 3' side of the nucleotide sequence of SEQ ID NO:29; using this plasmid, one can produce soluble human MCP having affinity for phosphatidylserine which is a peptide consisting of an amino acid sequence in which the amino acid sequence of SEQ ID NO:9 is linked to the C terminus of the amino acid sequence of SEQ ID NO:25 (said soluble human MCP is hereinafter designated as rsMCP(D) C2).

EXAMPLE 21
Expression of rsMCP(D) and rsMCP(D)C2

The plasmid pM1390 prepared in Example 20 and the pM851 described in International Patent Publication WO/93/17122 were each transfected into COS-1 cells (supra) by a DEAE dextran method (supra), thereby expressing soluble human MCP having affinity for phosphatidylserine (rsMCP(D)C2) and unmodified soluble human MCP (rsMCP(D)). Stated more specifically, ca. $3 \times 10^5$ cells/9 $cm^2$ were inoculated in each plastic tissue culture plate and cultivated at 37° C. for one day in 2 mL of a Dulbecco modified Eagle's medium (supra) containing 10% fetal bovine serum. After washing three times with 2 mL of DMEM, the culture medium was replaced by 0.7 mL of DMEM containing 1 μg of each of the plasmids, 50 mM Tris-HCl (pH 7.4), 0.2 mg/mL of DEAE dextran and 150 μM chloroquine. After cultivation at 37° C. for 4 h, the culture solution was removed by suction; after washing once with 2 mL of DMEM and once with DMEM containing 10% fetal bovine serum, 2 mL of DMEM containing 10% fetal bovine serum was added and cultivation was continued at 37° C. for 24 h. Thereafter, the culture medium was replaced by DMEM containing 0.1% BSA and cultivation was continued at 37° C. for an additional 72 h, and the supernatant of the culture was collected. It was found that the collected culture medium contained soluble human MCP having affinity for phosphatidylserine (rsMCP(D)C2) and unmodified soluble human MCP (rsMCP(D)) in amounts of 1–5 μg/mL.

The collected culture solution was purified in accordance with the method described in International Patent Publication WO/93/17122 to yield in pure form of the soluble human MCP having affinity for phosphatidylserine (rsMCP (D)C2) and the unmodified soluble human MCP (rsMCP (D)).

INDUSTRIAL APPLICABILITY

According to the present invention, there are provided a drug and a novel peptide that are useful as preventives and therapeutics of diseases involving coagulopathy, inflammations and immune response, as well as DNA necessary for producing them and a process for producing said drug.

What is claimed is:

1. A peptide comprising an amino acid sequence represented by the general formula selected from the group consisting of:

$(A2)n_2-(A3)_1$ and $(A2)n_2$, wherein A2 is the amino acid sequence denoted by SEQ ID NO:2, A3 is the amino acid sequence denoted by SEQ ID NO:3, and $n_2$ is 2 or 3.

2. The peptide according to claim 1, wherein said amino acid sequence has a sequence represented by the general formula selected from the group consisting of:

$(A2)_2-(A3)_1$, $(A2)_3-(A3)_1$, and $(A2)_2$.

* * * * *